(12) United States Patent
Chang et al.

(10) Patent No.: US 10,894,091 B2
(45) Date of Patent: Jan. 19, 2021

(54) LINKER UNITS AND MOLECULAR CONSTRUCTS COMPRISING THE SAME

(71) Applicant: Immunwork Inc., Taipei (TW)

(72) Inventors: Tse-Wen Chang, Taipei (TW); Hsing-Mao Chu, Taipei (TW)

(73) Assignee: IMMUNWORK INC., Taipei (TW)

( * ) Notice: Subject to any disclaimer, the term of this patent is extended or adjusted under 35 U.S.C. 154(b) by 194 days.

(21) Appl. No.: 15/922,935

(22) Filed: Mar. 16, 2018

(65) Prior Publication Data

US 2018/0264133 A1 Sep. 20, 2018

Related U.S. Application Data

(60) Provisional application No. 62/472,011, filed on Mar. 16, 2017, provisional application No. 62/613,401, filed on Jan. 3, 2018.

(51) Int. Cl.
| | |
|---|---|
| A61K 47/68 | (2017.01) |
| A61K 47/64 | (2017.01) |
| A61K 47/65 | (2017.01) |
| A61K 47/60 | (2017.01) |
| C07K 16/30 | (2006.01) |
| C07K 16/28 | (2006.01) |

(52) U.S. Cl.
CPC .......... *A61K 47/6889* (2017.08); *A61K 47/60* (2017.08); *A61K 47/64* (2017.08); *A61K 47/65* (2017.08); *A61K 47/6817* (2017.08); *A61K 47/6849* (2017.08); *A61K 47/6859* (2017.08); *C07K 16/303* (2013.01); *C07K 16/2809* (2013.01); *C07K 2317/622* (2013.01)

(58) Field of Classification Search
CPC .......... A61K 47/65; A61K 47/60; A61K 47/56
See application file for complete search history.

(56) References Cited

U.S. PATENT DOCUMENTS

2004/0229260 A1* 11/2004 Wallach ................ C12N 9/80
435/6.14

FOREIGN PATENT DOCUMENTS

| WO | WO-2015054658 A1 * | 4/2015 | ......... A61K 47/6803 |
| WO | WO-2016184426 A1 * | 11/2016 | ........... C07K 16/283 |
| WO | WO-2017144620 A1 * | 8/2017 | ......... G01N 33/5008 |

OTHER PUBLICATIONS

Topp et al (Journal of Clinical Oncology, 2011, vol. 29, pp. 2493-2498) (Year: 2011).*

* cited by examiner

*Primary Examiner* — Karen A. Canella

(57) ABSTRACT

The present disclosure provides various linker units and molecular constructs, each of which has a targeting element and an effector element linked therewith. Methods for treating various diseases using such linker units and molecular constructs are also disclosed.

23 Claims, 27 Drawing Sheets

Specification includes a Sequence Listing.

```
                        SEQUENCE LISTING

<160> NUMBER OF SEQ ID NOS: 24

<210> SEQ ID NO 1
<211> LENGTH: 18
<212> TYPE: PRT
<213> ORGANISM: Artificial Sequence
<220> FEATURE:
<223> OTHER INFORMATION: synthesized

<400> SEQUENCE: 1

Gly Gly Ser Gly Gly Ser Gly Gly Ser Lys Gly Ser Gly Ser Lys Gly
1               5                   10                  15

Ser Lys

<210> SEQ ID NO 2
<211> LENGTH: 19
<212> TYPE: PRT
<213> ORGANISM: Artificial Sequence
<220> FEATURE:
<223> OTHER INFORMATION: synthesized

<400> SEQUENCE: 2

Gly Gly Ser Gly Gly Ser Lys Gly Ser Lys Gly Ser Lys Gly Ser Lys
1               5                   10                  15

Gly Ser Lys

<210> SEQ ID NO 3
<211> LENGTH: 23
<212> TYPE: PRT
<213> ORGANISM: Artificial Sequence
<220> FEATURE:
<223> OTHER INFORMATION: synthesized

<400> SEQUENCE: 3

Gly Ser Ser Gly Ser Ser Lys Gly Ser Gly Lys Gly Ser Gly Lys Gly
1               5                   10                  15

Ser Gly Lys Gly Ser Gly Lys
            20

<210> SEQ ID NO 4
<211> LENGTH: 22
<212> TYPE: PRT
<213> ORGANISM: Artificial Sequence
<220> FEATURE:
<223> OTHER INFORMATION: synthesized

<400> SEQUENCE: 4

Gly Ser Ser Gly Ser Ser Gly Ser Ser Gly Ser Lys Gly Ser Gly Ser
1               5                   10                  15

Lys Gly Ser Gly Ser Lys
            20

<210> SEQ ID NO 5
<211> LENGTH: 10
<212> TYPE: PRT
<213> ORGANISM: Artificial Sequence
<220> FEATURE:
<221> NAME/KEY: MOD_RES
<222> LOCATION: 1,3,5,7,9
```

```
<223> OTHER INFORMATION: Xaa is PEGylated amino acid with four EG units
<220> FEATURE:
<223> OTHER INFORMATION: synthesized

<400> SEQUENCE: 5

Xaa Lys Xaa Lys Xaa Lys Xaa Lys Xaa Lys
1               5                   10

<210> SEQ ID NO 6
<211> LENGTH: 6
<212> TYPE: PRT
<213> ORGANISM: Artificial Sequence
<220> FEATURE:
<223> OTHER INFORMATION: synthesized

<400> SEQUENCE: 6

Ser Lys Ser Lys Ser Lys
1               5

<210> SEQ ID NO 7
<211> LENGTH: 5
<212> TYPE: PRT
<213> ORGANISM: Artificial Sequence
<220> FEATURE:
<223> OTHER INFORMATION: synthesized

<400> SEQUENCE: 7

Lys Ser Lys Gly Lys
1               5

<210> SEQ ID NO 8
<211> LENGTH: 18
<212> TYPE: PRT
<213> ORGANISM: Artificial Sequence
<220> FEATURE:
<223> OTHER INFORMATION: synthesized

<400> SEQUENCE: 8

Gly Gly Ser Gly Gly Ser Lys Gly Ser Ser Gly Lys Gly Gly Ser Gly
1               5                   10                  15

Gly Ser

<210> SEQ ID NO 9
<211> LENGTH: 14
<212> TYPE: PRT
<213> ORGANISM: Artificial Sequence
<220> FEATURE:
<223> OTHER INFORMATION: synthesized

<400> SEQUENCE: 9

Cys Gly Gly Gly Gly Ser Asp Tyr Met Gly Trp Met Asp Phe
1               5                   10

<210> SEQ ID NO 10
<211> LENGTH: 6
<212> TYPE: PRT
<213> ORGANISM: Artificial Sequence
<220> FEATURE:
<223> OTHER INFORMATION: synthesized

<400> SEQUENCE: 10

Cys Gly Gly Gly Gly Ser
1               5

<210> SEQ ID NO 11
<211> LENGTH: 16
```

```
<212> TYPE: PRT
<213> ORGANISM: Artificial Sequence
<220> FEATURE:
<223> OTHER INFORMATION: synthesized

<400> SEQUENCE: 11

Gly Ser Ser Gly Ser Ser Gly Ser Ser Gly Lys Gly Ser Gly Lys
1               5                   10                  15

<210> SEQ ID NO 12
<211> LENGTH: 6
<212> TYPE: PRT
<213> ORGANISM: Artificial Sequence
<220> FEATURE:
<223> OTHER INFORMATION: synthesized

<400> SEQUENCE: 12

Arg Ser Gly Ser Ser Gly
1               5

<210> SEQ ID NO 13
<211> LENGTH: 20
<212> TYPE: PRT
<213> ORGANISM: Artificial Sequence
<220> FEATURE:
<223> OTHER INFORMATION: synthesized

<400> SEQUENCE: 13

Gly Gly Ser Gly Gly Ser Gly Gly Ser Lys Gly Ser Ser Gly Lys Gly
1               5                   10                  15

Ser Ser Gly Lys
            20

<210> SEQ ID NO 14
<211> LENGTH: 8
<212> TYPE: PRT
<213> ORGANISM: Artificial Sequence
<220> FEATURE:
<223> OTHER INFORMATION: synthesized

<400> SEQUENCE: 14

Ser Gly Ser Ser Gly Ser Ser Gly
1               5

<210> SEQ ID NO 15
<211> LENGTH: 25
<212> TYPE: PRT
<213> ORGANISM: Artificial Sequence
<220> FEATURE:
<223> OTHER INFORMATION: synthesized

<400> SEQUENCE: 15

Gly Gly Ser Gly Gly Ser Gly Gly Ser Lys Gly Ser Ser Gly Lys Gly
1               5                   10                  15

Ser Ser Gly Lys Gly Ser Ser Gly Lys
            20                  25

<210> SEQ ID NO 16
<211> LENGTH: 14
<212> TYPE: PRT
<213> ORGANISM: Artificial Sequence
<220> FEATURE:
<223> OTHER INFORMATION: synthesized

<400> SEQUENCE: 16

Glu Gly Gly Gly Gly Ser Asp Tyr Met Gly Trp Met Asp Phe
```

```
                     1               5                   10

<210> SEQ ID NO 17
<211> LENGTH: 6
<212> TYPE: PRT
<213> ORGANISM: Artificial Sequence
<220> FEATURE:
<223> OTHER INFORMATION: synthesized

<400> SEQUENCE: 17

Glu Gly Gly Gly Gly Ser
1               5

<210> SEQ ID NO 18
<211> LENGTH: 8
<212> TYPE: PRT
<213> ORGANISM: Artificial Sequence
<220> FEATURE:
<223> OTHER INFORMATION: synthesized

<400> SEQUENCE: 18

Asp Tyr Met Gly Trp Met Asp Phe
1               5

<210> SEQ ID NO 19
<211> LENGTH: 18
<212> TYPE: PRT
<213> ORGANISM: Artificial Sequence
<220> FEATURE:
<223> OTHER INFORMATION: synthesized

<400> SEQUENCE: 19

Gly Ser Thr Ser Gly Ser Gly Lys Pro Gly Ser Gly Glu Gly Ser Thr
1               5                   10                  15

Lys Gly

<210> SEQ ID NO 20
<211> LENGTH: 10
<212> TYPE: PRT
<213> ORGANISM: Artificial Sequence
<220> FEATURE:
<223> OTHER INFORMATION: synthesized

<400> SEQUENCE: 20

Gly Gly Gly Gly Ser Gly Gly Gly Gly Ser
1               5                   10

<210> SEQ ID NO 21
<211> LENGTH: 255
<212> TYPE: PRT
<213> ORGANISM: Artificial Sequence
<220> FEATURE:
<223> OTHER INFORMATION: synthesized

<400> SEQUENCE: 21

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
```

```
            65                  70                  75                  80
Leu Gln Met Asp Ser Leu Arg Pro Glu Asp Thr Gly Val Tyr Phe Cys
                    85                  90                  95

Ala Arg Tyr Tyr Asp Asp His Tyr Ser Leu Asp Tyr Trp Gly Gln Gly
                100                 105                 110

Thr Pro Val Thr Val Ser Ser Gly Ser Thr Ser Gly Ser Gly Lys Pro
                115                 120                 125

Gly Ser Gly Glu Gly Ser Thr Lys Gly Asp Ile Gln Met Thr Gln Ser
130                 135                 140

Pro Ser Ser Leu Ser Ala Ser Val Gly Asp Arg Val Thr Ile Thr Cys
145                 150                 155                 160

Ser Ala Ser Ser Val Ser Tyr Met Asn Trp Tyr Gln Gln Thr Pro
                165                 170                 175

Gly Lys Ala Pro Lys Arg Trp Ile Tyr Asp Thr Ser Lys Leu Ala Ser
                180                 185                 190

Gly Val Pro Ser Arg Phe Ser Gly Ser Gly Ser Gly Thr Asp Tyr Thr
                195                 200                 205

Phe Thr Ile Ser Ser Leu Gln Pro Glu Asp Ile Ala Thr Tyr Tyr Cys
                210                 215                 220

Gln Gln Trp Ser Ser Asn Pro Phe Thr Phe Gly Gln Gly Thr Lys Leu
225                 230                 235                 240

Gln Ile Thr Arg Gly Gly Gly Gly Ser Gly Gly Gly Ser Cys
                245                 250                 255

<210> SEQ ID NO 22
<211> LENGTH: 19
<212> TYPE: PRT
<213> ORGANISM: Artificial Sequence
<220> FEATURE:
<223> OTHER INFORMATION: synthesized

<400> SEQUENCE: 22

Cys Gly Gly Ser Gly Gly Ser Gly Gly Ser Lys Gly Ser Gly Ser Lys
1               5                   10                  15

Gly Ser Lys

<210> SEQ ID NO 23
<211> LENGTH: 8
<212> TYPE: PRT
<213> ORGANISM: Artificial Sequence
<220> FEATURE:
<223> OTHER INFORMATION: synthesized

<400> SEQUENCE: 23

Trp Ala Asp Trp Pro Gly Pro Pro
1               5

<210> SEQ ID NO 24
<211> LENGTH: 5
<212> TYPE: PRT
<213> ORGANISM: Artificial Sequence
<220> FEATURE:
<223> OTHER INFORMATION: synthesized

<400> SEQUENCE: 24

Gly Gly Gly Gly Ser
1               5
```

LINKER UNITS AND MOLECULAR CONSTRUCTS COMPRISING THE SAME

CROSS-REFERENCE TO RELATED APPLICATIONS

This application relates to and claims the benefit of U.S. Provisional Application Nos. 62/472,011 filed Mar. 16, 2017, and 62/613,401 filed Jan. 3, 2018; the content of the application is incorporated herein by reference in its entirety.

BACKGROUND OF THE INVENTION

1. Field of the Invention

The present disclosure relates to the field of pharmaceuticals; more particularly, to multi-functional molecular constructs, e.g., those having multiple functional properties, such as effector, targeting, and for pharmacokinetic improvement.

2. Description of the Related Art

The development of pharmaceuticals with both targeting and therapeutic effects has become a much sought-after research area. For example, the multi-arm linker units, as disclosed in International Patent Application No. WO2016112870 (A1), and its related applications represent major chemical entities for the construction of molecules with two or more functional parts. However, the WO2016112870 publication employs amino acids with build-in functional groups such as tetrazine, cyclooctene, and cyclooctyne, for click chemistry reaction; yet these amino acids are not available for incorporation in the peptide core during solid-phase peptide synthesis. Moreover, according to the WO2016112870 publication, the coupling arm with tetrazine, cyclooctene, or cyclooctyne group is built in via a reaction between the thiol group of a cysteine residue and a maleimide group of a heterobifunctional linker that comprises the maleimide group at one terminus and a tetrazine, cyclooctene, or cyclooctyne group at the other terminus. The product of thiol and maleimide reaction is known to be unstable, undergoing a reverse reaction or exchange reaction with adjacent thiol-group containing molecules, which might affect the stability of the conjugated linkers in storage. Furthermore, when the peptide core contains a cysteine residue, as taught in the WO2016112870 publication, it is not feasible to carry out the continual solid-phase synthesis (branching of the peptide) of linking arms with a functional group that may react with the thiol group on a peptide core. Additionally, the alpha-amine group at the N-terminal of the peptide core requires an extra step of blocking, thereby reducing yield and purity of the peptide core or the linker unit.

In view of the forgoing, there exists in the related art a need for a novel multi-arm linker unit, which may address at least one of the issues discussed above. For example, such novel multi-arm linker unit may be synthesized with continual solid-phase synthesis, and/or exhibit more desirable stability and/or conjugating efficacy to functional elements (e.g., targeting elements, effector elements and/or elements for improving pharmacokinetics).

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

<I> Multi-Arm Linker Units

In the first aspect, the present disclosure is directed to a novel peptide core-based multi-arm linker unit that has a plurality of linking arms for conjugating with functional elements.

According to embodiments of the present disclosure, the present core comprises a plurality of linking amino acid residues, one or more spacers, and one or two conjugating moieties. Each of the linking amino acid residues may be a natural or a non-natural amino acid residue that has a side chain amine group (e.g., the lysine (K) residue) or a carboxyl group (e.g., the aspartic acid (D) or glutamic acid (E) residue). In various embodiments, any two of the linking amino acid residues are adjacent to each other or are separated by one of the spacers.

Each of the spacers comprises, independently, (1) one or more non-K amino acid residues (i.e., the amino acid residues other than the K residue), or (2) a PEGylated amino acid having 2 to 12 repeats of ethylene glycol (EG) unit. According to some illustrative embodiments, the spacer may comprises one or more glycine (G) and/or serine (S) residues. In some examples, the spacer consists of 1 to 20 amino acid residues; preferably, 2 to 5 amino acid residues.

According to some embodiments of the present disclosure, one of the spacers is linked to the N-terminus of the first linking amino acid residue starting from the N-terminus, and accordingly, forms an N-terminal spacer. Additionally or alternatively, one of the spacers is linked to the C-terminus of the last linking amino acid residue starting from the N-terminus, thereby forming a C-terminal spacer.

The conjugating moiety has either a carboxyl group (i.e., —$CO_2H$ group) or an amine group (i.e., —$NH_2$ group) at one terminus, and a conjugating group at the other terminus. For example, the conjugating group is an azide, alkyne, tetrazine, cyclooctene or cyclooctyne group. Specifically, in the case where the spacer is linked to the N-terminus of the first linking amino acid residue (i.e., as an N-terminal spacer), the conjugating moiety has a carboxyl group so that it is bonded to the N-terminus of the N-terminal spacer via forming an amide bond with the alpha-amine group of the N-terminal spacer. Alternatively, when the spacer is linked to the C-terminus of the last linking amino acid residue (i.e., as a C-terminal spacer), the conjugating moiety has an amine group, and is bonded to the C-terminus of the C-terminal spacer via forming an amide bond with the carboxyl group of the C-terminal spacer. The thus-bonded conjugating moiety has a conjugating group at the free-terminus (i.e., the terminus not reacting to the N-/C-terminal spacer) thereof.

The linking arms are extended from linking amino acid residues in the peptide core. According to embodiments of the present disclosure, each linking arm has a reactive group at one terminus thereof and a functional group at the other terminus thereof. The reactive group may be a succinimidyl ester (SE; for example, hydroxysuccinimide-ester or N-hydroxysuccinimidyl (NETS) ester), tetrafluorophenyl (TFP) ester, carboxyl group, or hydroxyl group (i.e., —OH group), and the functional group is selected from the group consisting of amine, carboxyl, hydroxyl, tert-Butyldimethylsilyl (TBDMS), NETS, maleimide, vinyl sulfone, mono-sulfone, methyl sulfonyl benzothiazole, iodo, iodoacetamide, azide, alkyne, cyclooctyne, tetrazine, and cyclooctene groups.

Structurally, each linking arm is linked to one linking amino acid residue via forming an amide bond between the reactive group of the linking arm and the amine or carboxyl group of the linking amino acid reside. In some embodiments, when the present core comprises a plurality of K residues, then each linking arm has an amine-reactive group (such as a succinimidyl ester, TFP ester or carboxyl group). In this case, the linking arm may be linked to the K residues via forming an amide bond with the amine group of the K residue. Alternatively, when the present core comprises a plurality of D and/or E residues, then each linking arm has a carboxyl-reactive group (e.g., a hydroxyl group), and accordingly, the linking arm may be linked to the D and/or E residues via forming an amide bond with the carboxyl group of the D and/or E residue. After being linked to the present core, each linking arm has a functional group at the free-terminus (i.e., the terminus that is not attached to the present core) thereof.

When choosing the conjugating group and the functional group, it is desirable that the conjugating group of the conjugating moiety and the functional group of the linking arm cannot undergo a click chemistry reaction with each other. For example, when the conjugating group of the conjugating moiety is an azide, alkyne or cyclooctyne group, the functional group of the linking arm is a tetrazine or cyclooctene group; alternatively, when the conjugating group of the conjugating moiety is a tetrazine or cyclooctene group, the functional group of the linking arm is an azide, alkyne, or cyclooctyne group. The same design methodology is also applicable to the conditions where the linker unit comprises two conjugating moieties respectively linked to the N- and C-terminal spacers; that is, the functional group of the linking arm and the conjugating groups of the two conjugating moieties cannot undergo the click chemistry reaction with one another. Therefore, in such cases, the functional group of the linking arm may be a maleimide, vinyl sulfone, mono-sulfone, iodo or iodoacetamide group; the conjugating group of one conjugating moiety is an azide, alkyne, or cyclooctyne group; while the conjugating group of the other conjugating moiety is a tetrazine or cyclooctene group. As could be appreciated, in the situation where the two conjugating moieties are intended to conjugate with a single species of element, the conjugating group of the two conjugating moieties may be the same or may be subjected to the same click chemistry reaction.

According to some working examples of the present disclosure, each of the linking arms is a peptide comprising 2-12 non-K amino acid residues, or a polyethylene glycol (PEG) chain having 2-24 repeats of EG units. In one specific example, each of the linking arms is a peptide comprising 5-10 amino acid residues that are independently selected from the group consisting of G, S, E and arginine (R) residues. In an alternative example, each of the linking arms is a PEG chain having 6-12 repeats of EG units.

Depending on desired purposes, different functional elements (serving as the targeting or effector elements) may be respectively linked to the free-terminus of the linking arms and the conjugating group of the present linker unit. According to certain embodiments of the present disclosure, the present linker unit comprises a plurality of linking arms and one conjugating moiety, in which a plurality of first elements are linked to the plurality of linking arms via forming an amide bond or an ester bond therebetween, or via thiol-maleimide reaction, SN2 reaction, copper catalyzed azide-alkyne cycloaddition (CuAAC) reaction, strained-promoted azide-alkyne click chemistry (SPAAC) reaction, or inverse electron demand Diels-Alder (iEDDA) reaction; and a second element is linked to the conjugating group via CuAAC reaction, SPAAC reaction or iEDDA reaction. Alternatively, the present linker unit may comprise a plurality of linking arms and two conjugating moieties; accordingly, multiple elements may be respectively linked to the linking arms and the two conjugating moieties. Specifically, plurality of first elements are respectively linked to the linking arms via forming an amide bond or an ester bond therebetween, or via thiol-maleimide reaction or SN2 reaction; a second element is linked to the conjugating group of one conjugating moiety via SPAAC reaction or iEDDA reaction; and a third element is linked to the conjugating group of the other conjugating moiety via CuAAC reaction, SPAAC reaction or iEDDA reaction. As would be appreciated, said second and third elements may be the same or different. Since the first elements are conjugated with the linking amino acid residues (e.g., K residues) of the peptide core through the linking arms, it is feasible to adjust the number of first element carried by a linker unit by changing the number of the linking amino acid residue. Accordingly, the ratio of the number of the first element to the second (or to the second and third) can be altered as desired and needed.

According to optional embodiments of the present disclosure, the cyclooctene group is norbornene or trans-cyclooctene (TCO), or derivatives thereof. Illustrative examples of the cyclooctyne group include dibenzocyclooctyne (DIBO), difluorinated cyclooctyne (DIFO), bicyclononyne (BCN), and dibenzoazacyclooctyne (DIBAC or DBCO), and derivatives thereof. Examples of the tetrazine group include, but are not limited to, 1,2,3,4-tetrazine, 1,2,3,5-tetrazine and 1,2,4,5-tetrazine, and derivatives thereof.

<II> Molecular Constructs with Two or More Linker Units (Joint-Linkers)

In another aspect, the present disclosure is directed to a molecular construct comprising at least two linker units coupling to each other via the respective conjugating group thereon. Each linker unit is amenable to carrying one or more elements, such that when coupled with each other, the thus-obtained molecular construct may comprise elements with different functionalities (such as, targeting, therapeutic, or pharmacokinetic functions). In this case, the ratio of the numbers between different functional elements may be adjusted by changing the number of the linking amino acid residues of the peptide core of the respective linker unit.

According to certain embodiments of the present disclosure, the molecular construct comprises a first and a second linker units. The basic structure of the first or second linker unit is substantially the same as those described above in connection with the first aspect of the present disclosure. Specifically, the first linker unit comprises a first core, and a plurality of linking arms (hereinafter, the first linking arms) respectively linked to the first core, in which the first core comprises a conjugating moiety (hereinafter, the first conjugating moiety) linked to the N- or C-terminus thereof; the second linker unit comprises a second core, and a plurality linking arms (hereinafter, the second linking arms) respectively linked to the second core, in which the second core comprises a conjugating moiety (hereinafter, the second conjugating moiety) linked to the N- or C-terminus thereof. The first and second linker units are then coupled to each other via iEDDA, SPAAC, or CuAAC reaction occurred between the conjugating groups of the first and second conjugating moieties.

For the purpose of treatment, different functional elements (serving as the targeting and effector elements) may be respectively linked to the first and second linking arms via forming an amide bond or an ester bond therebetween, or via thiol-maleimide reaction, SN2 reaction, CuAAC reaction, SPAAC reaction, or iEDDA reaction.

This design allows for a facile synthesis of a molecular construct with a complex structure. In this way, it becomes feasible for a skilled artisan to construct libraries of molecular constructs respectively carrying different functional elements, and then select and combine two molecular constructs (or linker units) from the libraries to generate desired constructs, depending on the needs and/or intended applications. Moreover, the number of functional elements for a linker unit is controlled by adjusting the number of linking amino acid residues of the cores.

<III> Uses of the Present Linker Unit or Molecular Construct in Disease Treatment The present linker unit and molecular construct can both be employed for the construction of pharmaceutical molecules for treating various diseases; for example, diffused tumors and solid tumors. Therefore, subject matters that are also included in other aspects of the present disclosure include pharmaceutical compositions comprising the present linker units and molecular constructs, method of treating diseases using the present linker units and molecular constructs or the pharmaceutical compositions comprising the same, as well as the use of the present linker units and molecular constructs in the manufacture of a medicament for use in the disease treatment.

To construct pharmaceutical molecules suitable for treating diffused tumors, the first element may be an antibody fragment, such as a single chain variable fragment (scFv), a single-domain antibody (sdAb), or the like, which is specific for a first cell surface protein, and the second element is a cytotoxic drug, or an antibody fragment specific for a second cell surface protein. The first cell surface antigen suitable for use as the targeting element for treating diffused tumor includes, but is not limited to, CD5, CD19, CD20, CD22, CD23, CD27, CD30, CD33, CD34, CD37, CD38, CD43, CD72a, CD78, CD79a, CD79b, CD86, CD134, CD137, CD138, and CD319. On the other hand, non-limiting examples of the second cell surface antigen suitable for use as the effector element include CD3 and CD16a. Alternatively, the first and second cell surface antigens are respectively CD79a and CD79b.

Examples of the diffused tumors treatable by the present linker unit and/or molecular construct include, but are not limited to, acute lymphocytic leukemia (ALL), chronic lymphocytic leukemia (CLL), acute myelogenous leukemia (AML), chronic myelogenous leukemia (CIVIL), Hodgkin lymphoma, non-Hodgkin lymphoma, and myeloma.

To construct a molecular construct for treating solid tumors, the first element (i.e., the targeting element) may be chosen from a peptide hormone, a growth factor, and a first antibody fragment specific for a tumor-associated antigen; whereas the second element (i.e., the effector element) may be a cytotoxic drug, a toll-like receptor (TLR) agonist, a chelator complexed with a radioactive nuclide, a cytokine, or a second antibody fragment specific for a second growth factor, a cell surface antigen, a hapten, or the cytokine.

For example, the peptide hormone may be secretin, cholecystokinin (CCK), somatostatin and analogues (e.g., octreotide), or thyroid-stimulating hormone (TSH). Regarding the first growth factor, it may be the epidermal growth factor (EGF), mutant EGF, epiregulin, heparin-binding epidermal growth factor (HB-EGF), vascular endothelial growth factor A (VEGF-A), basic fibroblast growth factor (bFGF), or hepatocyte growth factor (HGF). Illustrative examples of the tumor-associated antigen include epidermal growth factor receptor (HER1), HER2, HER3, HER4, carbohydrate antigen 19-9 (CA 19-9), carbohydrate antigen 125 (CA 125), carcinoembryonic antigen (CEA), mucin 1 (MUC 1), ganglioside GD2, melanoma-associated antigen (MAGE), prostate-specific membrane antigen (PSMA), prostate stem cell antigen (PSCA), mesothelin, mucine-related Tn, Sialyl Tn, Globo H, stage-specific embryonic antigen-4 (SSEA-4), and epithelial cell adhesion molecule (EpCAM).

Examples for the cytotoxic drug suitable for use in the linker unit or molecular construct for the treatment of diffused tumors or solid tumors include, but are not limited to, mertansine, auristatin, maytansine, doxorubicin, calicheamicin, and camptothecin. Non-limiting TLR agonist includes lipopolysaccharide (LPS), monophosphoryl lipid A, motolimod, imiquimod, resiquimod, gardiquimod, CpG oligodeoxynucleotide (CpG DON), lipoteichoic acid, β-glucan, and zymosan. The chelator is selected from the group consisting of 1,4,7,10-tetraazacyclododecane-1,4,7,10-tetraacetic acid (DOTA), 1,4,7-triaza-cyclo-nonane-1,4,7-triacetic acid (NOTA), 1,4,7-triazacyclononane-1,4-diacetic acid (NODA), and diethylenetriaminepentaacetic acid (DTPA); and the radioactive nuclide is $^{111}$In, $^{131}$I, or $^{177}$Lu. As to the cytokine, it can be selected from the group consisting of interleukin-2 (IL-2), IL-10, IL-12, interferon-alpha (IFN-α), IFN-γ, TGF-β, or tumor necrosis factor-alpha (TNF-α). The second growth factor capable of being specifically recognized and bound by the second antibody fragment may be EGF, mutant EGF, VEGF-A, bFGF, or HGF. The cell surface antigen specifically recognized and bound by the second antibody fragment may be selected from the group consisting of CD3, CD16a, CD28, CD134, cytotoxic T-lymphocyte-associated protein 4 (CTLA-4, or CD152), programmed cell death 1 (PD-1, or CD279), and programmed cell death 1 ligand 1 (PD-L1, or CD274). The cytokine specifically recognized and bound by the second antibody fragment may be selected from the group consisting of IL-2, IFN-α, IFN-γ, and TNF-α; in these cases, the second antibody fragment is a non-neutralizing antibody fragment. The hapten may be selected from the group consisting of dinitrophenol (DNP), trinitrophenol (TNP), and a short peptide having an amino acid sequence of WADWPGPP (SEQ ID NO: 23).

Exemplary solid tumors treatable by the present linker unit and/or molecular construct include, melanomas, esophageal carcinomas, gastric carcinomas, brain tumor, small cell lung cancer, non-small cell lung cancer, bladder cancer, breast cancer, pancreatic cancer, colon cancer, rectal cancer, colorectal cancer, renal cancer, hepatocellular carcinoma, ovary cancer, prostate cancer, thyroid cancer, testis cancer, and head and neck squamous cell carcinoma.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings briefly discussed below.

Figure 1A:
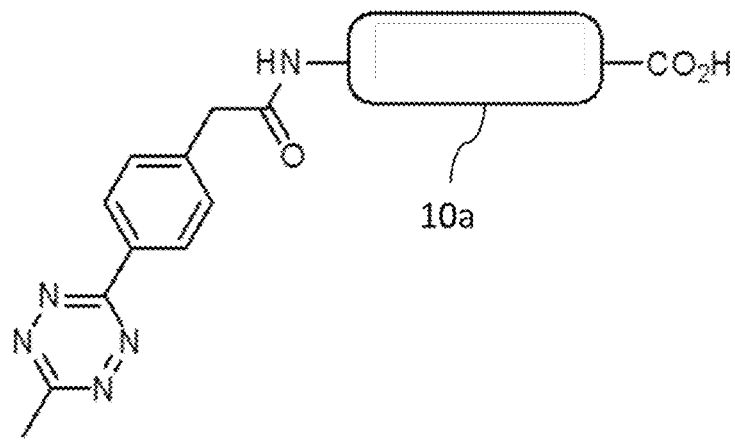
FIG. 1A to FIG. 1H are schematic diagrams illustrating cores according to certain embodiments of the present disclosure.
Figure 1B:
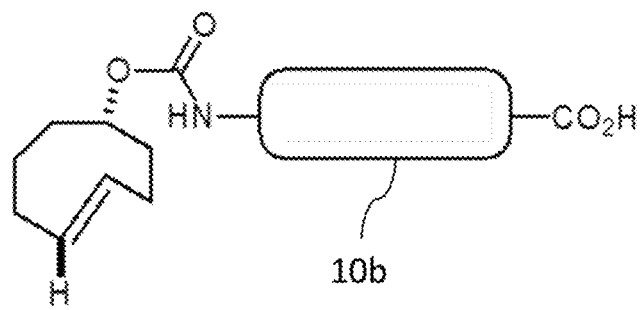
Figure 1C:
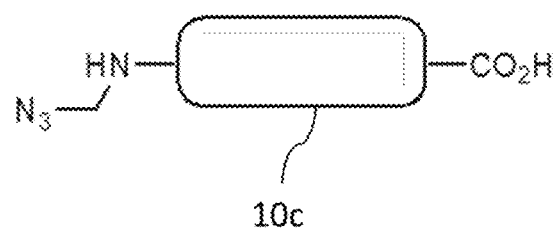
Figure 1D:
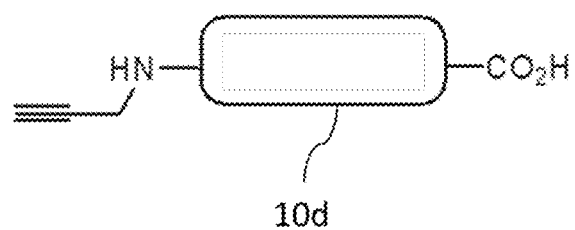

In accordance with common practice, the various described features/elements are not drawn to scale but instead are drawn to best illustrate specific features/elements relevant to the present invention. Also, like reference numerals and designations in the various drawings are used to indicate like elements/parts.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art.

Unless otherwise required by context, it will be understood that singular terms shall include plural forms of the same and plural terms shall include the singular. Specifically, as used herein and in the claims, the singular forms "a" and "an" include the plural reference unless the context clearly indicated otherwise. Also, as used herein and in the claims, the terms "at least one" and "one or more" have the same meaning and include one, two, three, or more. Similarly, the term "at least two" include two, three, four, or more. Furthermore, the phrases "at least one of A, B, and C", "at least one of A, B, or C" and "at least one of A, B and/or C," as use throughout this specification and the appended claims, are intended to cover A alone, B alone, C alone, A and B together, B and C together, A and C together, as well as A, B, and C together.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

This present disclosure pertains generally to molecular constructs, in which each molecular construct comprises a targeting element (T) and an effector element (E), and these molecular constructs are sometimes referred to as "T-E molecules," "T-E pharmaceuticals" or "T-E drugs" in this document.

As used herein, the term "targeting element" refers to the portion of a molecular construct that directly or indirectly binds to a target of interest (e.g., a receptor on a cell surface or a protein in a tissue) thereby facilitates the transportation of the present molecular construct into the interested target. In some example, the targeting element may direct the molecular construct to the proximity of the target cell. In other cases, the targeting element specifically binds to a molecule present on the target cell surface or to a second molecule that specifically binds a molecule present on the cell surface. In some cases, the targeting element may be internalized along with the present molecular construct once it is bound to the interested target, hence is relocated into the cytosol of the target cell. A targeting element may be an antibody or a ligand for a cell surface receptor, or it may be a molecule that binds such antibody or ligand, thereby indirectly targeting the present molecular construct to the target site (e.g., the surface of the cell of choice). The localization of the effector (therapeutic agent) in the diseased site will be enhanced or favored with the present molecular constructs as compared to the therapeutic without a targeting function. The localization is a matter of degree or relative proportion; it is not meant for absolute or total localization of the effector to the diseased site.

According to the present invention, the term "effector element" refers to the portion of a molecular construct that elicits a biological activity (e.g., inducing or suppressing immune activities, exerting cytotoxic effects, inhibiting enzymes, and the like) or other functional activity (e.g., recruiting immunocytes or other therapeutic molecules), once the molecular construct is directed to its target site. The "effect" can be therapeutic or diagnostic. The effector elements encompass those that bind to cells and/or extracellular immunoregulatory factors. The effector element comprises agents such as proteins, nucleic acids, lipids, carbohydrates, glycopeptides, drug moieties (both small molecule drug and biologics), compounds, elements, and isotopes, and fragments thereof.

Although the terms, first, second, third, etc., may be used herein to describe various elements, components, regions, and/or sections, these elements (as well as components, regions, and/or sections) are not to be limited by these terms. Also, the use of such ordinal numbers does not imply a sequence or order unless clearly indicated by the context. Rather, these terms are simply used to distinguish one element from another. Thus, a first element, discussed below, could be termed a second element without departing from the teachings of the exemplary embodiments.

Here, the terms "link," "couple," and "conjugate" are used interchangeably to refer to any means of connecting two components either via direct linkage or via indirect linkage between two components.

The term "polypeptide" as used herein refers to a polymer having at least two amino acid residues. Typically, the polypeptide comprises amino acid residues ranging in length from 2 to about 200 residues; preferably, 2 to 50 residues. Where an amino acid sequence is provided herein, L-, D-, or beta amino acid versions of the sequence are also contemplated. Polypeptides also include amino acid polymers in which one or more amino acid residues are an artificial chemical analogue of a corresponding naturally occurring amino acid, as well as to naturally occurring amino acid polymers. In addition, the term applies to amino acids joined by a peptide linkage or by other, "modified linkages," e.g., where the peptide bond is replaced by an α-ester, a β-ester, a thioamide, phosphoramide, carbomate, hydroxylate, and the like.

In certain embodiments, conservative substitutions of the amino acids comprising any of the sequences described herein are contemplated. In various embodiments, one, two, three, four, or five different residues are substituted. The term "conservative substitution" is used to reflect amino acid substitutions that do not substantially alter the activity (e.g., biological or functional activity and/or specificity) of the molecule. Typically, conservative amino acid substitutions involve substitution one amino acid for another amino acid with similar chemical properties (e.g., charge or hydrophobicity). Certain conservative substitutions include "analog substitutions" where a standard amino acid is replaced by a non-standard (e.g., rare, synthetic, etc.) amino acid differing minimally from the parental residue. Amino acid analogs are considered to be derived synthetically from the standard amino acids without sufficient change to the structure of the parent, are isomers, or are metabolite precursors. In the present application, the amino acid residues (1) lysine, which contains an amine group in its side chain, (2) cysteine, which contains a thiol group in its side chain, (3) serine and threonine, which contain a hydroxyl group in their side chain, and (4) aspartic acid and glutamic acid, which contain a carboxyl group in their side chain, are considered four distinctive groups of amino acids. These four groups of amino acids each contain in their side chains a unique functional group, which may be applied for conjugating to various chemical components. Non-natural amino acids, which contain the same functional groups in the side chains may be substituted for similar purposes.

In certain embodiments, polypeptides comprising at least 80%, preferably at least 85% or 90%, and more preferably at least 95% or 98% sequence identity with any of the sequences described herein are also contemplated.

"Percentage (%) amino acid sequence identity" with respect to the polypeptide sequences identified herein is defined as the percentage of polypeptide residues in a candidate sequence that are identical with the amino acid residues in the specific polypeptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two polypeptide sequences was carried out by computer program Blastp (protein-protein BLAST) provided online by Nation Center for Biotechnology Information (NCBI). The percentage amino acid sequence identity of a given polypeptide sequence A to a given polypeptide sequence B (which can alternatively be phrased as a given polypeptide sequence A that has a certain % amino acid sequence identity to a given polypeptide sequence B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in A or B, whichever is shorter.

The term "PEGylated amino acid" as used herein refers to a polyethylene glycol (PEG) chain with one amino group and one carboxyl group. Generally, the PEGylated amino acid has the formula of $NH_2—(CH_2CH_2O)_n—CO_2H$. In the present disclosure, the value of n ranges from 1 to 20; preferably, ranging from 2 to 12.

The term "conjugating moiety" as used herein refers to a molecule having one or more functional group, which is chemically reactive and is capable of binding covalently to other chemical units. Non-limiting examples of the functional group include, hydroxyl, carbonyl, carboxyl, thiol, amine, tert-Butyldimethylsilyl (TBDMS), N-hydroxysuccinimidyl (NETS), maleimide, vinyl sulfone, mono-sulfone, methylsulfonyl benzothiazole, iodo, iodoacetamide azide, alkyne, tetrazine, cyclooctene, and cyclooctyne groups. According to embodiments of the present disclosure, the conjugating moiety of the present linker unit has two functional groups, in which one is a carboxyl or amine group for binding with the alpha-amine or carboxyl group of the spacer via forming an amide bond therebetween so that the conjugating moiety is bonded to the N- or C-terminus of the spacer; and the other is an azide, alkyne, tetrazine, cyclooctene or cyclooctyne group for binding with the element or another linker unit via the CuAAC, iEDDA or SPAAC reaction.

As used herein, the term "terminus" with respect to a polypeptide refers to an amino acid residue at the N- or C-end of the polypeptide. With regard to a polymer, the term "terminus" refers to a constitutional unit of the polymer (e.g., the polyethylene glycol of the present disclosure) that is positioned at the end of the polymeric backbone. In the present specification and claims, the term "free terminus" is used to mean the terminal amino acid residue or constitutional unit is not chemically bound to any other molecular.

The term "antigen" or "Ag" are interchangeably used and refers to a molecule that elicits an immune response. This immune response may involve a secretory, humoral and/or cellular antigen-specific response. In the present disclosure, the term "antigen" can be any of a protein, a polypeptide (including mutants or biologically active fragments thereof), a polysaccharide, a glycoprotein, a glycolipid, a nucleic acid, or a combination thereof.

In the present specification and claims, the term "antibody" is used in the broadest sense and covers fully assembled antibodies, antibody fragments that bind with antigens, such as antigen-binding fragment (Fab/Fab'), F(ab')$_2$ fragment (having two antigen-binding Fab portions linked together by disulfide bonds), variable fragment (Fv), single chain variable fragment (scFv), bi-specific single-chain variable fragment (bi-scFv), nanobodies (also referred to as single-domain antibodies, sdAb), unibodies and diabodies. "Antibody fragments" comprise a portion of an intact antibody, preferably the antigen-binding region or variable region of the intact antibody. Typically, an "antibody" refers to a protein consisting of one or more polypeptides substantially encoded by immunoglobulin genes or fragments of immunoglobulin genes. The well-known immunoglobulin genes include the kappa, lambda, alpha, gamma, delta, epsilon, and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. A typical immunoglobulin (antibody) structural unit is known to comprise a tetramer. Each tetramer is composed of two identical pairs of polypeptide chains, with each pair having one "light" chain (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively. According to embodiments of the present disclosure, the antibody fragment can be produced by modifying the nature antibody or by de novo synthesis using recombinant DNA methodologies. In certain embodiments of the present disclosure, the antibody and/or antibody fragment can be bispecific, and can be in various configurations. For example, bispecific antibodies may comprise two different antigen binding sites (variable regions). In various embodiments, bispecific antibodies can be produced by hybridoma technique or recombinant DNA technique. In certain embodiments, bispecific antibodies have binding specificities for at least two different epitopes. In many of the molecular configurations that employ antibody fragments, the antibody fragments may be substituted for antibody mimetics, which bind to the same antigenic components as the antibody fragments. Antibody mimetics include anticalins, DARPins, affibodies, filomers, ankyrins, avimers, and others.

The term "specifically binds" as used herein, refers to the ability of an antibody or an antigen-binding fragment thereof, to bind to an antigen with a dissociation constant (Kd) of no more than about $1\times10^{-6}M$, $1\times10^{-7}M$, $1\times10^{-8}M$, $1\times10^{-9}M$, $1\times10^{-10}M$, $1\times10^{-11}M$, $1\times10^{-12}M$, and/or to bind to an antigen with an affinity that is at least two-folds greater than its affinity to a nonspecific antigen.

The term "treatment" as used herein includes preventative (e.g., prophylactic), curative or palliative treatment; and "treating" as used herein also includes preventative (e.g., prophylactic), curative or palliative treatment. In particular, the term "treating" as used herein refers to the application or administration of the present molecular construct or a pharmaceutical composition comprising the same to a subject, who has a medical condition a symptom associated with the medical condition, a disease or disorder secondary to the medical condition, or a predisposition toward the medical condition, with the purpose to partially or completely alleviate, ameliorate, relieve, delay onset of, inhibit progression of, reduce severity of, and/or reduce incidence of one or more symptoms or features of said particular disease, disorder, and/or condition. Treatment may be administered to a subject who does not exhibit signs of a disease, disorder, and/or condition, and/or to a subject who exhibits only early signs of a disease, disorder and/or condition, for the purpose of decreasing the risk of developing pathology associated with the disease, disorder and/or condition.

The term "effective amount" as used herein refers to the quantity of the present molecular construct that is sufficient to yield a desired therapeutic response. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as particular condition being treated, the physical condition of the patient (e.g., the patient's body mass, age, or gender), the type of subject being treated, the duration of the treatment, the nature of concurrent therapy (if any), and the specific formulations employed and the structure of the compounds or its derivatives. Effective amount may be expressed, for example, as the total mass of active component (e.g., in grams, milligrams or micrograms) or a ratio of mass of active component to body mass, e.g., as milligrams per kilogram (mg/kg).

The terms "application" and "administration" are used interchangeably herein to mean the application of a molecular construct or a pharmaceutical composition of the present invention to a subject in need of a treatment thereof.

The terms "subject" and "patient" are used interchangeably herein and are intended to mean an animal including the human species that is treatable by the molecular construct, pharmaceutical composition, and/or method of the present invention. The term "subject" or "patient" intended to refer to both the male and female gender unless one gender is specifically indicated. Accordingly, the term "subject" or "patient" comprises any mammal, which may benefit from the treatment method of the present disclosure. Examples of a "subject" or "patient" include, but are not limited to, a human, rat, mouse, guinea pig, monkey, pig, goat, cow, horse, dog, cat, bird and fowl. In an exemplary embodiment, the patient is a human. The term "mammal" refers to all members of the class Mammalia, including humans, primates, domestic and farm animals, such as rabbit, pig, sheep, and cattle; as well as zoo, sports or pet animals; and rodents, such as mouse and rat. The term "non-human mammal" refers to all members of the class Mammals except human.

The present disclosure is based, at least on the construction of the T-E pharmaceuticals that can be delivered to target cells, target tissues or organs at increased proportions relative to the blood circulation, lymphoid system, and other cells, tissues or organs. When this is achieved, the therapeutic effect of the pharmaceuticals is increased, while the scope and severity of the side effects and toxicity is decreased. It is also possible that a therapeutic effector is administered at a lower dosage in the form of a T-E molecule, than in a form without a targeting component. Therefore, the therapeutic effector can be administered at lower dosages without losing potency, while lowering side effects and toxicity.

Part I Novel Design of Multi-Arm Linkers

I-(i) New Forms of Multi-Arm Linkers

The first aspect of the present disclosure pertains to a multi-arm linker unit that comprises, (1) a core comprising a plurality of linking amino acid residues, and (2) a plurality of linking arms respectively linked to the linking amino acid residues of the core. The present core is characterized in having one or two conjugating moieties bonded to its N- or/and C-terminus. According to embodiments of the present disclosure, the conjugating moiety is useful in efficiently coupling a functional element (e.g., a targeting element, a therapeutic effector element, or an element for improving pharmacokinetics) to the core so as to improve the therapeutic effect of the present linker unit.

The core is a polypeptide that has 3-120 amino acid residues in length, and comprises at least two linking amino acid residues, which are independently lysine (K), aspartic acid (D) and/or glutamic acid (E) residues; for example, the present core may comprise 2, 3, 4, 5, 6, 7, 8, 9, 10, 11, 12, 13, 14, 15, 16, 17, 18, 19, 20, 21, 22, 23, 24, 25 or more K, D and/or E residues. Preferably, the present core comprises two to twenty K residues, or two to twenty D and/or E residues. As could be appreciated, the linking amino acid residue may be a non-natural amino acid residue, which has an amine or carboxyl group at its side chain. According to the embodiments, any two of the linking amino acid residues may be adjacent to each other or are separated by a spacer.

According to embodiments of the present disclosure, the peptide core comprises at least one (i.e., 1, 2, 3 or more) spacer. In certain embodiments, one spacer is linked to the N-terminus of the first linking amino acid residue starting from the N-terminus of the polypeptide; in the following description, such spacer is, when appropriate, designated as the N-terminal spacer since it is disposed at the N-terminus of the core. Additionally or alternatively, one spacer is linked to the C-terminus of the last linking amino acid residue starting from the N-terminus of the polypeptide; similarly, such spacer is sometimes referred to as the C-terminal spacer hereinafter because it is disposed at the C-terminus of the core.

In general, the spacer mentioned above may be, (1) a single amino acid residue other than the linking amino acid residue, (2) a peptide of 2-20 (i.e., 2, 3, 4, 5, 6, 7, 8, 9, 10, 11, 12, 13, 14, 15, 16, 17, 18, 19, or 20) amino acid residues other than the linking amino acid residue, or (3) a PEGylated amino acid, with EG units of 2 to 12 (i.e., having 2, 3, 4, 5, 6, 7, 8, 9, 10, 11 or 12 EG units). Specifically, in the case when the present core comprises a plurality of K residues, the spacer may either comprise a PEGylated amino acid having 2-12 EG unit, or comprise 1-12 non-K amino acid residues, wherein each of the non-K amino acid residues are respectively selected from the group consisting of, glycine (G), aspartic acid (D), glutamic acid (E), serine (S), arginine (R), histidine (H), threonine (T), asparagine (N), glutamine (Q), proline (P), alanine (A), valine (V), isoleucine (I), leucine (L), methionine (M), phenylalanine (F), tyrosine (Y), and tryptophan (W) residues; preferably, each of the non-K amino acid residues are respectively selected from the group consisting of, G, S, R, H, T, N, Q, P, A, V, I, L, M, F, Y, and W residues; more preferably, each of the non-K amino acid residues are respectively G and/or S residues. Alternatively, when the present core comprises a plurality of D/E residues, the spacer may either comprise a PEGylated amino acid having 2-12 EG unit, or comprise 1-12 non-D/E amino acid residues, wherein each of the non-D/E amino acid residues are respectively selected from the group consisting of, K, G, S, R, H, T, N, Q, P, A, V, I, L, M, F, Y, and W residues; preferably, each of the non-D/E amino acid residues are respectively selected from the group consisting of, G, S, R, H, T, N, Q, P, A, V, I, L, M, F, Y, and W residues; more preferably, each of the non-D/E amino acid residues are respectively G and/or S residues.

As could be appreciated, when the present core comprises more than one spacers, each of the spacers may be the same or different; that is, each of the spacers may comprise the same of different amino acid sequences and/or EG units. According to one embodiment of the present disclosure, the present core comprises three spacers, in which one of the spacers is a PEGylated amino acid having 8 repeats of EG unit, and the other two spacers are respectively one S residue and one G residue. According to another embodiment of the present disclosure, the present core comprises five spacers, in which one of the spacers consists of four G and two S residues, while the other four spacers respectively consists of one G and one S residue. According to still another embodiment of the present disclosure, the present core comprises five spacers, each being a PEGylated amino acid having 4 repeats of EG unit.

In the preparation of the present linker unit, a peptide or a PEG chain that has an amine-reactive group (e.g., a succinimidyl ester, a TFP ester or a carboxyl group) or a carboxyl-reactive group (e.g., an amine group), is linked to the linking amino acid residues (i.e., the K, D and/or E residues) of the present core. More specifically, a peptide or a PEG chain that has an amine-reactive group at one terminus and a functional group at the other terminus may be linked to the K residue of the present core by forming an amide bond between the amine-reactive group of the peptide/PEG chain and the amine group of the K residue. The succinimidyl ester may be a NHS ester. Alternatively, a peptide or a PEG chain that has a carboxyl-reactive group at one-terminus and a functional group at the other terminus may be linked to the carboxyl group of the D or E residue of the present core by forming an amide bond between amine group of the peptide or PEG chain and carboxyl group of the D or E residue. In the present disclosure, the peptide or PEG chain linked to the linking amino acid residue is referred to as a linking arm, which has a functional group at the free-terminus thereof (i.e., the terminus that is not linked to the linking amino acid residue of the core). In general, said functional group is selected from the group consisting of, amine, carboxyl, hydroxyl, TBDMS, NHS, maleimide, vinyl sulfone, mono-sulfone, methylsulfonyl benzothiazole, iodo, iodoacetamide, azide, alkyne, cyclooctyne, tetrazine, and cyclooctene groups, in which the tetrazine group is 1,2,3,4-tetrazine, 1,2,3,5-tetrazine, 1,2,4,5-tetrazine, or derivatives thereof; the cyclooctene group is a norbornene or a trans-cyclooctene (TCO) group; and the cyclooctyne group is selected from the group consisting of, dibenzocyclooctyne (DIBO), difluorinated cyclooctyne (DIFO), bicyclononyne (BCN), and dibenzoazacyclooctyne (DIBAC or DBCO). According to one embodiment of the present disclosure, the tetrazine group is 6-methyl-tetrazine.

According to some embodiments of the present disclosure, the linking arm is a peptide comprising 2-12 (i.e., 2, 3, 4, 5, 6, 7, 8, 9, 10, 11 or 12) amino acid residues (each of which may be a natural or non-natural amino acid residue) other than the linking amino acid residue. In certain embodiments, the present core comprises a plurality of K residues, and the linking arm is a peptide comprises 2-12 non-K amino acid residues (i.e., the amino acid residues independently selected from the group consisting of, G, E, D, S, R, H, T, N, Q, P, A, V, I, L, M, F, Y, and W residues). According to one working example, the present core comprises a plurality of K residues, and the linking arm is a peptide comprising 5-10 amino acid residues that are independently selected from the group consisting of, G, S, E and R residues. Alternatively, the linking arm may be a PEG chain having 2-24 (i.e., 2, 3, 4, 5, 6, 7, 8, 9, 10, 11, 12, 13, 14, 15, 16, 17, 18, 19, 20, 21, 22, 23 or 24) repeats of EG unit; preferably, 5-15 repeats of EG units; more preferably, 6-12 repeats of EG units. As would be appreciated, the peptide or PEG chain of the linking arm may be substituted with a polymer of approximately the same length. A polymer comprising carbohydrate or other hydrophilic building blocks is suitable for use as the linking arms.

According to embodiments of the present disclosure, at least one conjugating moiety is bonded to the alpha-amine group of the N-terminal spacer, and/or bonded to the carboxyl group of the C-terminal spacer. A conjugating moiety cannot be an amino acid residue, because the amino acid residue has both amine and carboxylate groups; the two groups interfere with each other in forming a peptide bond with the peptide core.

Specifically, the conjugating moiety of the present linker unit has an amine-reactive group (e.g., a carboxyl or carbonyl chloride group) or a carboxyl-reactive group (e.g., an amine or hydrazine group) at one terminus, and a conjugating group at the other terminus, in which the conjugating group is selected from the group consisting of, azide, alkyne, tetrazine, cyclooctene and cyclooctyne groups (see above for illustrative examples thereof). According to some embodiments of the present disclosure, one of the spacers is an N-terminal spacer; in these embodiments, the conjugating moiety has a carboxyl group, and accordingly, may be bonded to the alpha-amine group of the N-terminal spacer via forming an amide bond between the carboxyl group of the conjugating moiety and the alpha-amine group of N-terminal spacer. According to certain embodiments of the present disclosure, one of the spacer is a C-terminal spacer; in these embodiments, the conjugating moiety has an amine group, and thus, may be bonded to the carboxyl group of the C-terminal spacer via forming an amide bond between the amine group of the conjugating moiety and the carboxyl group of the C-terminal spacer. As in the cases where the core comprises both an N-terminal spacer and a C-terminal spacer, the core also has two conjugating moieties, in which one conjugating moiety is bonded to the alpha-amine group of the N-terminal spacer, while the other conjugating moiety is bonded to the carboxyl group of the C-terminal spacer. The conjugating moiety bonded to the core thus has the conjugating group at the free-terminus thereof (i.e., the terminus that is not linked to the core).

Optionally, the conjugating moiety further comprises a PEG chain having 2-10 (i.e., 2, 3, 4, 5, 6, 7, 8, 9 or 10) repeats of EG units disposed between the carboxyl or amine group and the conjugating group; for example, the PEG chain may have 4, 6, 7 or 8 repeats of EG unit.

As would be appreciated, when the core has two conjugating moieties bonded thereto, the conjugating groups thereof may be the same or different. Preferably, the two conjugating groups are different. According to the preferred examples, one conjugating group is an azide, alkyne or cyclooctyne group, and the other conjugating group is a tetrazine or cyclooctene group.

Preferably, when the conjugating group of the conjugating moiety is an azide, alkyne, or cyclooctyne group, then the functional group of the linking arm is a tetrazine or cyclooctene group; and when the conjugating group of the conjugating moiety is the tetrazine or the cyclooctene group, then the functional group of the linking arm is the azide, alkyne, or cyclooctyne group. In the condition where the linker unit comprises two conjugating moieties respectively linked to the N- and C-terminal spacers, the functional group of the linking arm is preferably a maleimide, vinyl sulfone, mono-sulfone, iodo or iodoacetamide group; the conjugating group of one of the two conjugating moieties is an azide, alkyne, or cyclooctyne group; and the conjugating group of the other conjugating moiety is a tetrazine or cyclooctene group.

Figure 1E:
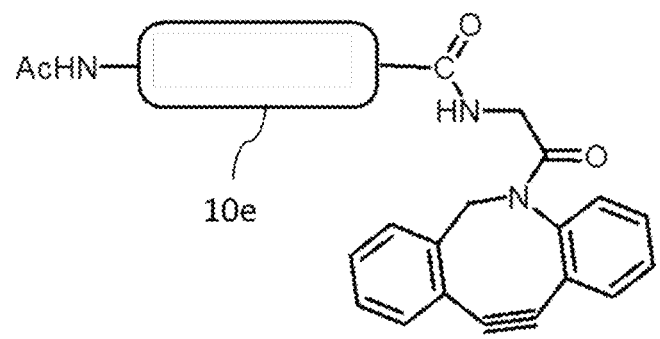

Reference is now made to FIGS. 1A-1E, in which each of the cores 10a, 10b, 10c, 10d and 10e has a conjugating moiety bonded thereto. In FIGS. 1A to 1D, conjugating moieties respectively having a tetrazine group, a TCO group, and azide group and an alkyne group are bonded to the alpha-amine groups of the N-terminal spacers of cores 10a, 10b 10c and 10d. FIG. 1E provides an alternative example, in which an acetyl group serving as a protecting group is bonded with the alpha-amine group of the spacer of the peptide core 10e, whereas a conjugating moiety having a DBCO group (as a conjugating group) is bonded with the carboxyl group of the C-terminal spacer of the core 10e.

Figure 1F:
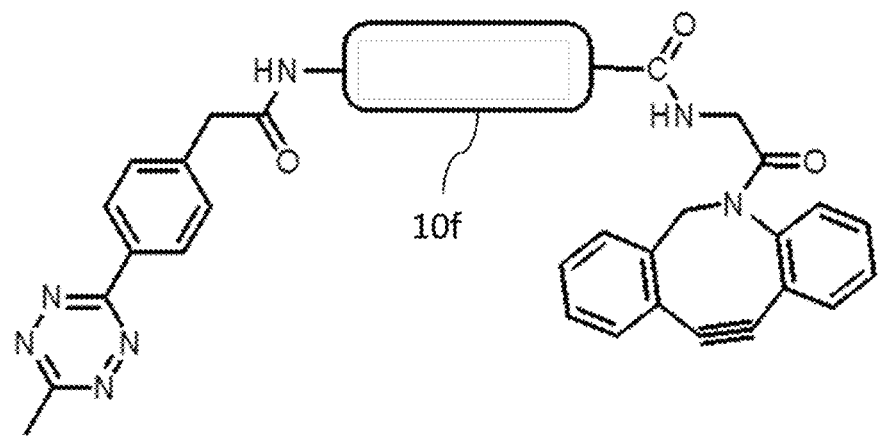
Figure 1G:
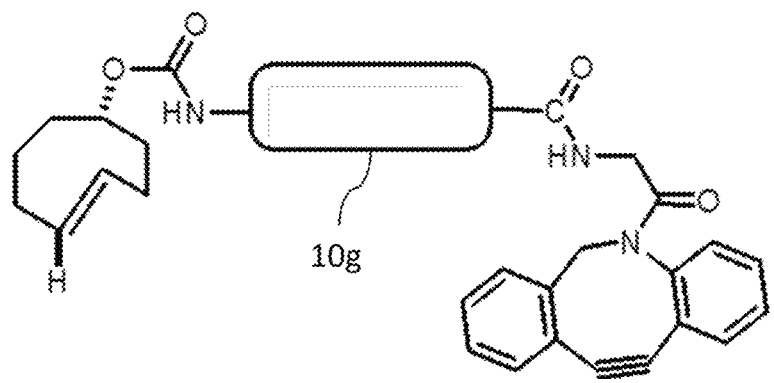
Figure 1H:
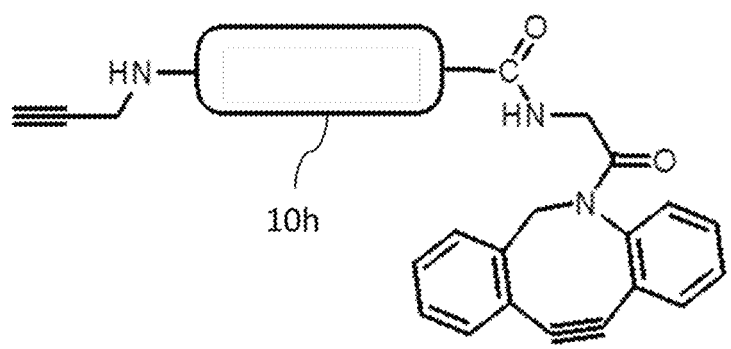

In some embodiments of the present disclosure, the core comprises two conjugating groups. FIG. 1F illustrates such an example, in which conjugating moieties respectively having a tetrazine group and a DBCO group are bonded to the alpha-amine group of the N-terminal spacer and the carboxyl group of the C-terminal spacer of the peptide core 10f. FIG. 1G provides another example, in which conjugating moieties respectively having a TCO group and a DBCO group are bonded to the alpha-amine group of the N-terminal spacer and the carboxyl group of the C-terminal spacer of the peptide core 10g. In an alternative example, the alpha-amine group of the N-terminal spacer and the carboxyl group of the C-terminal spacer of the peptide core 10h are respectively bonded with a conjugating moiety having an alkyne group and a conjugating moiety having a DBCO group.

Schemes 1-3 provide the examples of synthesizing the core having one or two specified conjugating moiety bonded thereto.

<<Scheme 1 Production of core having a tetrazine or TCO group bonded to the N terminus thereof>>

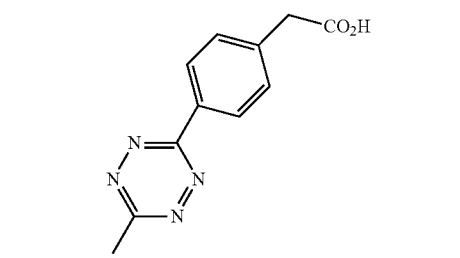

Tetrazine-CO₂H

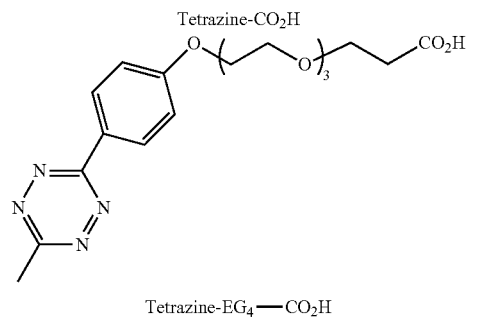

Tetrazine-EG₄—CO₂H

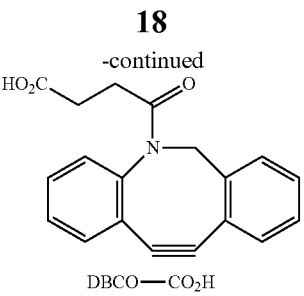

DBCO—CO₂H

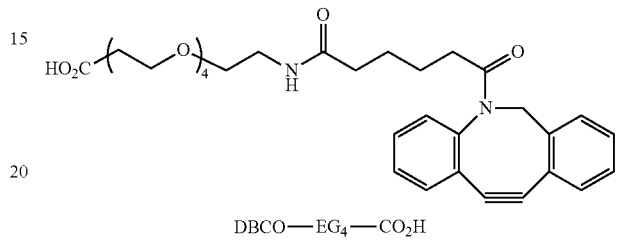

DBCO—EG₄—CO₂H

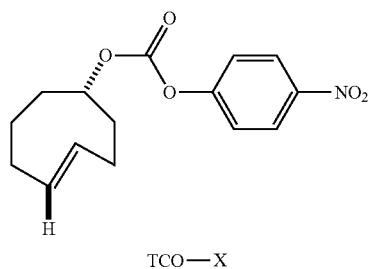

TCO—X

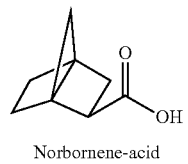

Norbornene-acid

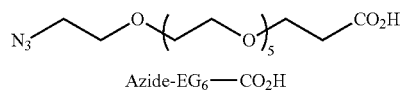

Azide-EG₆—CO₂H

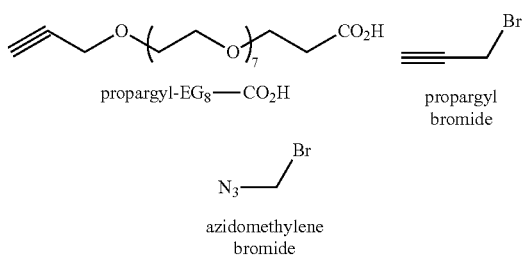

propargyl-EG₈—CO₂H     propargyl bromide azidomethylene bromide

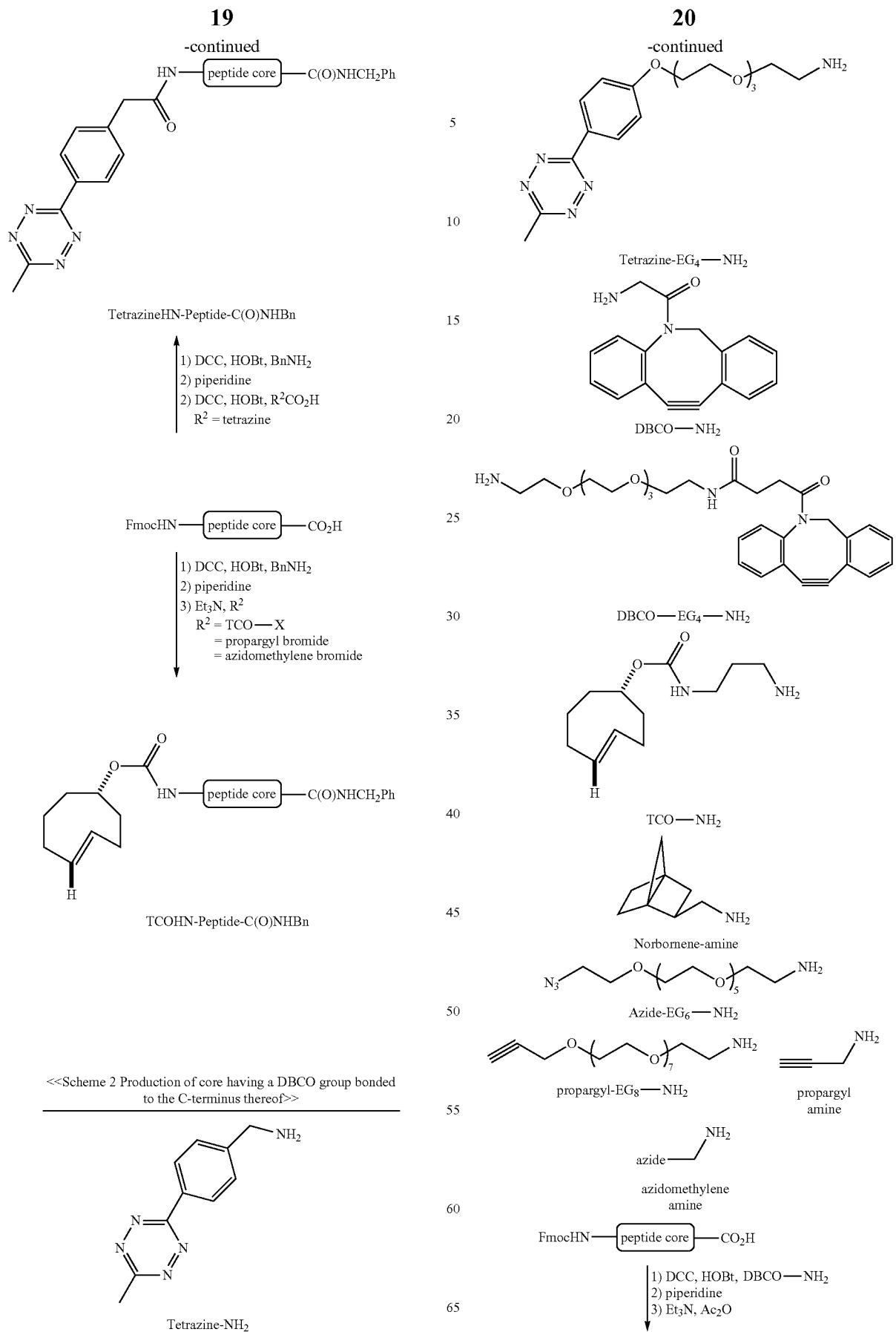

-continued

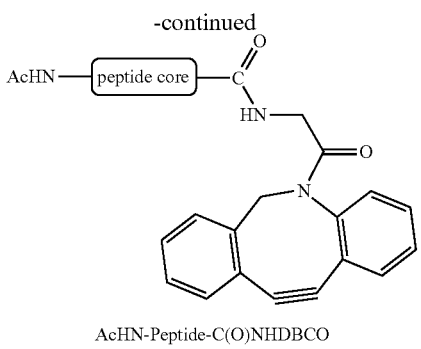

AcHN-Peptide-C(O)NHDBCO amino acids with varying lengths of PEG are used to construct the core, because the PEG moieties contained in the amino acid molecules provide conformational flexibility and adequate spacing between conjugating groups, enhance aqueous solubility, and are generally weakly immunogenic. The synthesis of PEGylated amino acid-containing core is similar to the process for the synthesis of regular polypeptides.

For stability purpose, in the case where the N-terminus of the core is not bonded with a conjugating moiety, it is preferably bonded with an acetyl group.

As could be appreciated, the number of the linking arms linked to the core is mainly determined by the number of linking amino acid resides (i.e., the K, D and/or E residues) comprised in the core. Since there are at least two linking

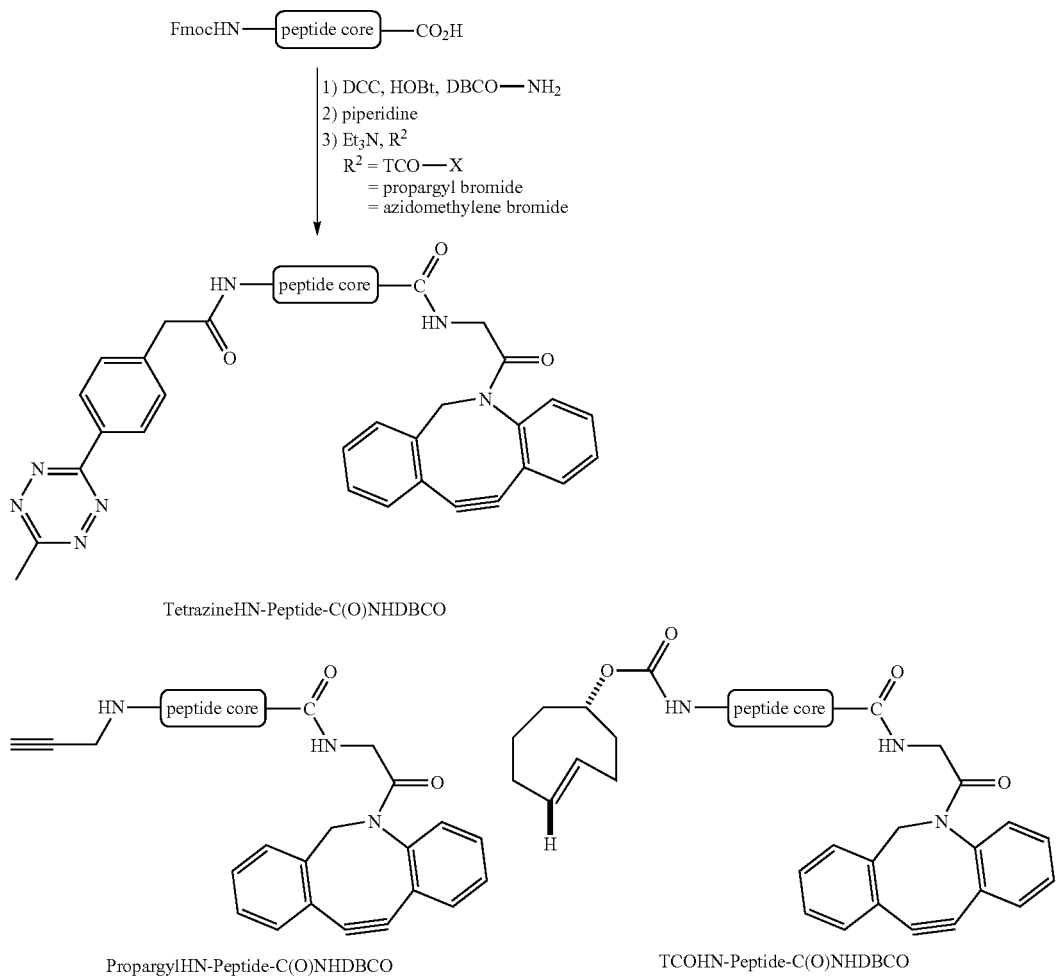

The synthesis of a peptide core using PEGylated amino acids as the spacers involves fewer steps than that with regular amino acids such as G and S resides. Moreover, PEGylated amino acids with varying lengths (i.e., numbers of repeated ethylene glycol units) may be employed, offering flexibility for solubility and spacing between adjacent amino groups of K residues. In addition to PEGylated amino acids, the cores may also be constructed to comprise artificial amino acids, such as D-form amino acids, homo-amino acids, N-methyl amino acids, etc. Preferably, the PEGylated amino acid residues comprised in the present core, the present linker unit may comprise a plurality of linking arms.

Figure 2A:
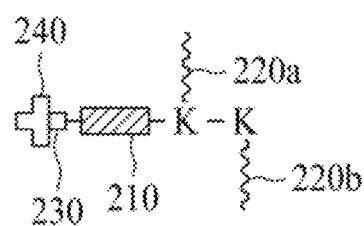
FIG. 2A to FIG. 2F are schematic diagrams illustrating linker units according to certain embodiments of the present disclosure.

Reference is now made to FIG. 2A. As illustrated, the linker unit 20A comprises a core, which comprises two adjacent K residues, and a spacer 210 (i.e., an "N-terminal spacer") linked to the N-terminus of the first K residues. A conjugating moiety having a carboxyl group 230 and a cyclooctene group 240 is bonded to the alpha-amine group of the spacer 210 via forming an amide bond between the carboxyl group 230 of the conjugating moiety and the alpha-amine group of the spacer 210. In this example, two linking arms 220a, 220b are independently linked to the K residues. As discussed below, the free terminus of the linking arm (i.e., the terminus that is not linked to the K residue) is useful in conjugating with the functional element, and the cyclooctene group 240 disposed at the N-terminus of the core allows for the conjugation with an additional functional element or another linker unit.

Figure 2B:
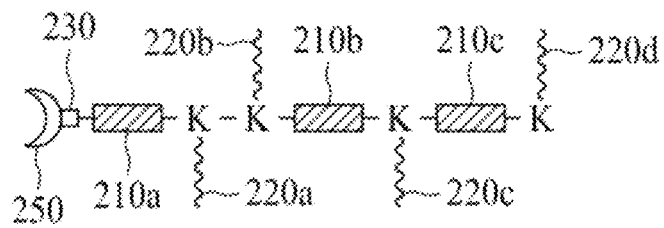

FIG. 2B provides an alternative example of the present linker unit. In FIG. 2B, the linker unit 20B comprises four K residues and four linking arms 220a-220d respectively linked to the four K residues. The first and second K residues are linked via forming an amide bond therebetween, and the second, third and fourth K residues are separated from one another by spacers 210b or 201c. A conjugating moiety having a carboxyl group 230 and an azide group 250 is bonded to the N-terminal spacer 210a via forming an amide bond between the carboxyl group 230 of the conjugating moiety and the alpha-amine group of the N-terminal spacer 210a. As afore-mentioned, the spacers 210a-210c may comprise the same or different amino acid sequences and/or EG units.

Figure 2C:
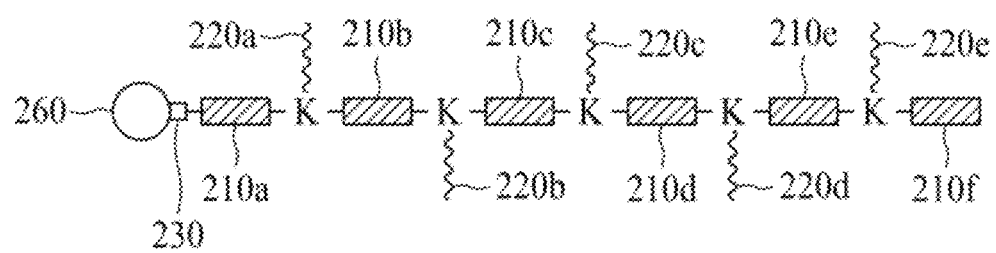

FIG. 2C is directed to a linker unit 20C, which comprises five K residues respectively separated by spacers 210b-210e and five linking arms 220a-220e respectively linked to the five K residues. In addition, the spacers 210a, 210f serving as the N- and C-terminal spacers are respectively linked to the N-terminus of the first K residue and the C-terminus of the last K residue. In this example, a conjugating moiety having a carboxyl group 230 and an alkyne group 260 is bonded to the spacer 210a via forming an amide bond between the carboxyl group 230 of the conjugating moiety and the alpha-amine group of the spacer 210a.

Figure 2D:
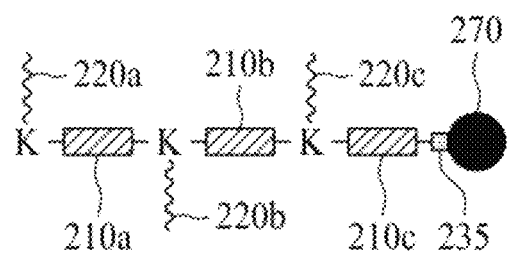

Reference is now made to FIG. 2D, in which the linker unit 20D has a structure similar to the linker units 20A-20C, except that the conjugating moiety is bonded to the C-terminus of the core, rather than the N-terminus of the core. As illustrated in FIG. 2D, the conjugating moiety having an amine group 235 and a cyclooctyne 270 is bonded to the C-terminal spacer 210c via forming an amide bond between the amine group 235 of the conjugating moiety and the carboxyl group of the C-terminal spacer 210c.

Figure 2E:
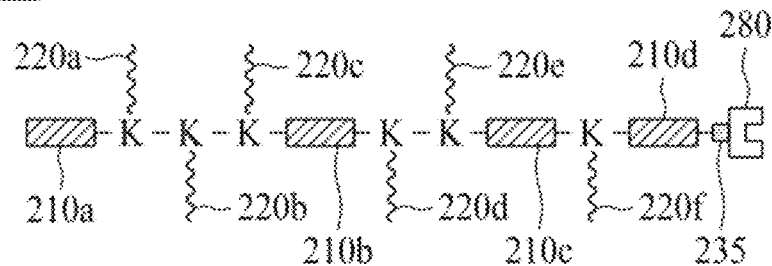

FIG. 2E provides an alternative example, in which the linker unit 20E comprises four spacers 210a-210d. In this example, the spacers 210a and 210d serving as the N- and C-terminal spacers are respectively linked to the N-terminus of the first K residue and the C-terminus of the last K residue; the spacer 210b is disposed between the third and fourth K residues; and the spacer 210c is disposed between the fifth and sixth K residues. The conjugating moiety having an amine group 235 and a tetrazine group 280 is bonded to the spacer 210d via forming an amide bond between the amine group 235 of the conjugating moiety and the carboxyl group of the spacer 210d.

Figure 2F:
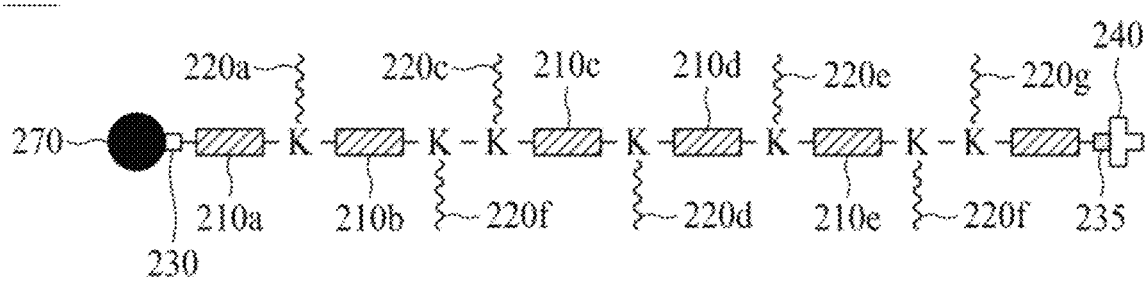

FIG. 2F provides a linker unit 20F comprising two conjugating moieties, according to another embodiment of the present disclosure. The present core comprises seven K residues. Two spacers 210a, 210f serving as the N- and C-terminal spacers are respectively disposed at the N-terminus and the C-terminus of the core. A conjugating moiety having a cyclooctyne group 270 is bonded to the alpha-amine group of the spacer 210a, and a conjugating moiety having a cyclooctene group 240 is bonded to the carboxyl group of the spacer 210f. As discussed below, the linker unit 20F may serve as a carrier to link with three kinds of functional groups respectively via the linking arms 220a-220g, the cyclooctyne group 270, and the cyclooctene group 240.

As could be appreciated, certain features discussed above regarding the linker units 20A-20F, or any other following linker units are common to other linker units disclosed herein, and hence some or all of these features are also applicable in the following examples, unless it is contradictory to the context of a particular embodiment. However, for the sake of brevity, these common features may not be explicitly repeated below.

Depending on the functional group (i.e., an amine, carboxyl, hydroxyl, TBDMS, NHS, maleimide, vinyl sulfone, mono-sulfone, methylsulfonyl benzothiazole, iodo, iodoacetamide, azide, alkyne, cyclooctyne, tetrazine, or cyclooctene group) present at the free terminus of the linking arm, it is feasible to design a functional element (such as, a targeting element, a therapeutic effector element, or an element for improving the pharmacokinetic property) with a corresponding functional group, so that the functional element may be linked to the free terminus of the linking arm via any of the following chemical reactions, (1) forming an amide bond therebetween: in this case, the linking arm has an amine, carboxyl or NHS group at the free terminus thereof, and the functional element has an amine or carboxyl group;

(2) forming an ester bond therebetween: in this case, the linking arm has a hydroxyl or TBDMS group at the free terminus thereof, and the functional element has an hydroxyl-reactive group (e.g., a tosyl-O group);

(3) the thiol-maleimide (or vinyl sulfone) reaction: in this case, the linking arm has a maleimide, a vinyl sulfone, a mono-sulfone or a methylsulfonyl benzothiazole group at the free terminus thereof, and the functional element has a thiol group;

(4) the SN2 reaction: in this case, the linking arm has an iodo or an iodoacetamide group at the free terminus thereof, and the functional element has a thiol group;

(5) the Copper(I)-catalyzed alkyne-azide cycloaddition reaction (CuAAC reaction): one of the free terminus of the linking arm and the functional element has an azide or a picolyl azide group, whereas the other has an alkyne group; the CuAAC reaction is exemplified in Schemes 4 and 5;

(6) the inverse electron demand Diels-Alder (iEDDA) reaction: one of the free terminus of the linking arm and the functional element has a tetrazine group, whereas the other has a cyclooctene group (e.g., a TCO or a norbornene group); the iEDDA reaction is exemplified in Schemes 6 and 7; or (7) the strained-promoted azide-alkyne click chemistry (SPAAC) reaction: one of the free terminus of the linking arm and the functional element has an azide group, whereas the other has an cyclooctyne group; the SPAAC reaction is exemplified in Scheme 8.

The CuAAC reaction yields 1,5 di-substituted 1,2,3-triazole. The reaction between alkyne and azide is very selective and there are no alkyne and azide groups in natural biomolecules. Furthermore, the reaction is quick and pH-insensitive. It has been suggested that instead of using copper (I), such as cuprous bromide or cuprous iodide, for catalyzing the click reaction, it is better to use a mixture of copper (II) and a reducing agent, such as sodium ascorbate to produce copper (I) in situ in the reaction mixture. Alternatively, the second element can be linked to the N- or C-terminus of the present core via a copper-free reaction, in which pentamethylcyclopentadienyl ruthenium chloride complex is used as the catalyst to catalyze the azide-alkyne cycloaddition.

<<Scheme 4 CuAAC reaction occurred between an azide and an alkyne groups>>

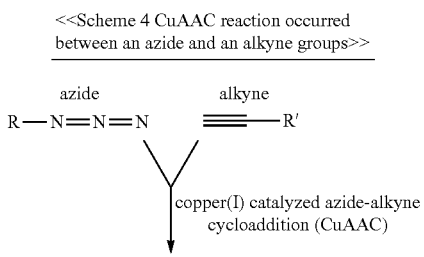

<<Scheme 5 CuAAC reaction occurred between a picolyl azide and an alkyne groups>>

Picolyl azide

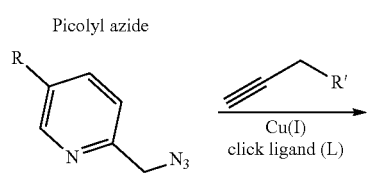

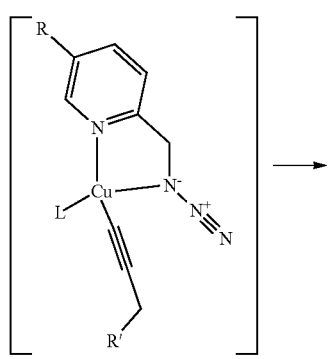

<<Scheme 6 iEDDA Reaction occurred between a TCO and a tetrazine groups>>

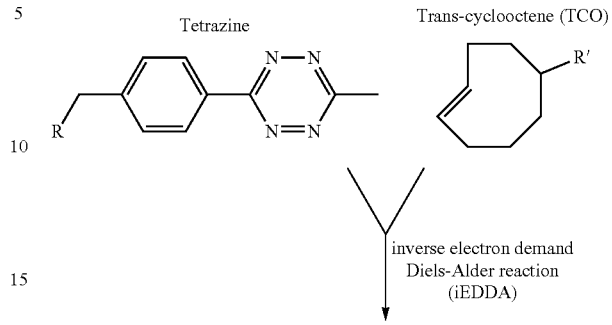

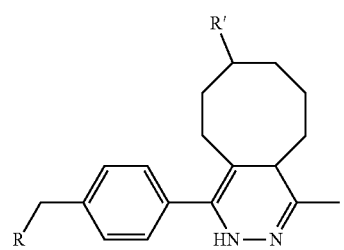

<<Scheme 7 iEDDA reaction occurred between a norbornene and a tetrazine groups>>

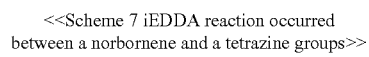

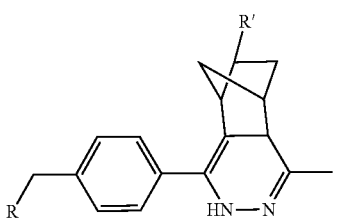

<<Scheme 8 SPAAC reaction occurred between an azide and a DBCO groups>>

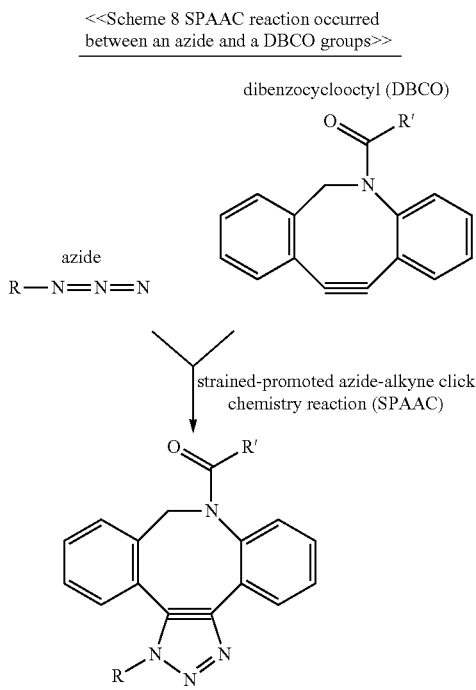

For the sake of illustration, the functional elements linked to the linking arms are referred to as the first elements. As could be appreciated, the number of the first elements carried by the present linker unit depends on the number of linking amino acid residues (i.e., K, D and/or E residues) of the core (and thus, the number of the linking arms). Accordingly, one of ordinary skill in the art may adjust the number of the first elements of the linker unit as necessary, for example, to achieve the desired targeting or therapeutic effect.

Figure 3A:
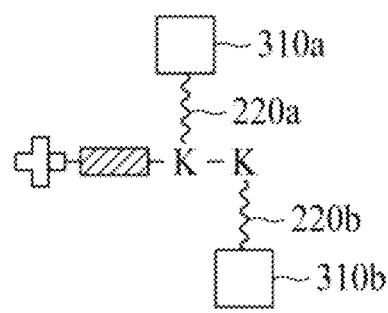
FIG. 3A to FIG. 3C are schematic diagrams illustrating linker units comprising functional elements linked thereto according to some embodiments of the present disclosure.
Figure 3B:
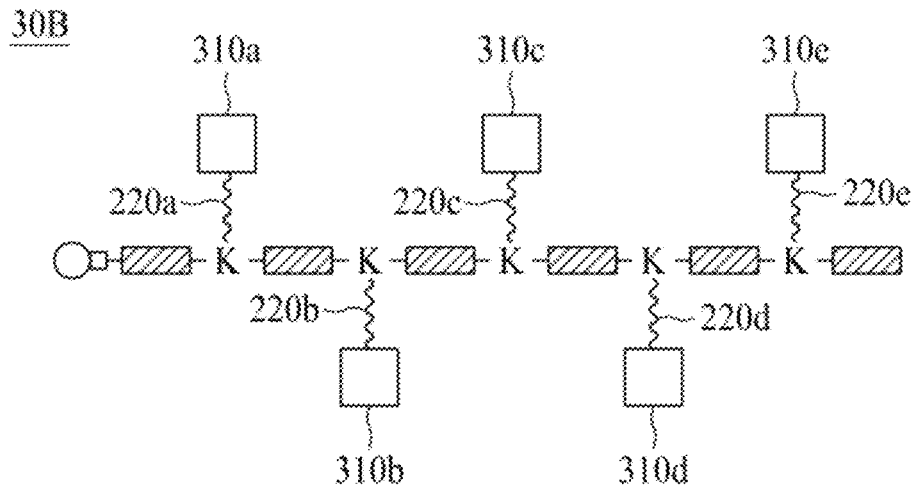
Figure 3C:
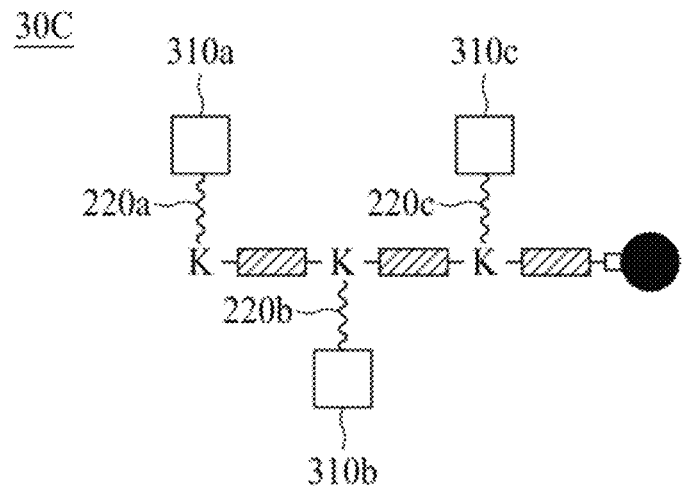

An example of a linker unit 30A having two first elements is illustrated FIG. 3A. The linker unit 30A has a structure similar to the linker unit 20A of FIG. 2A, except that two first elements 310a and 310b are respectively linked to the K residues of the core via the linking arms 220a and 220b. FIG. 3B provides another example, in which the linker unit 30B has five first elements 310a-310e respectively linked therewith via the linking arms 220a-220e. Similarly, in FIG. 3C, the linking arms 310a-310c allow for the conjugation of three first elements 310a-310c.

In order to increase the intended or desired effect (e.g., the therapeutic effect), the present linker unit may further comprise a second element in addition to the first element. For example, the second element can be either a targeting element or an effector element. In optional embodiments of the present disclosure, the first element is an effector element, while the second element may be another effector element, which works additively or synergistically with or independently of the first element. Still optionally, the first and second elements exhibit different properties; for example, the first element is a targeting element, and the second element is an effector element, and vice versa. Alternatively, the first element is an effector element, and the second element is an element capable of improving the pharmacokinetic property of the linker unit, such as solubility, clearance, half-life, and bioavailability. The choice of a particular first element and/or second element depends on the intended application in which the present linker unit (or multi-arm linker unit) is to be used. Examples of these functional elements are discussed below in Part I-(ii) of this specification.

Structurally, the second element is linked to the conjugating group (i.e., azide, alkyne, tetrazine, cyclooctene or cyclooctyne group) of the conjugating moiety bonded at the N- or C-terminus of the core. The second element may be optionally conjugated with a short PEG chain (preferably having 2-12 repeats of EG units) and then linked to the conjugating group.

According to some embodiments of the present disclosure, the conjugating group of the core is an azide, alkyne, tetrazine, cyclooctene or cyclooctyne group; and accordingly, a second element having an azide-reactive group (e.g., an alkyne or a DBCO group), an alkyne-reactive group (e.g., an azide group), a tetrazine-reactive group (e.g., a norbornene or a TCO group), a cyclooctene-reactive (e.g., a tetrazine group) or a cyclooctyne-reactive group (e.g., an azide group) can be linked to the conjugating group of the core via a suitable click chemistry reaction, such as the CuAAC reaction, iEDDA reaction or SPAAC reaction.

Figure 4A:
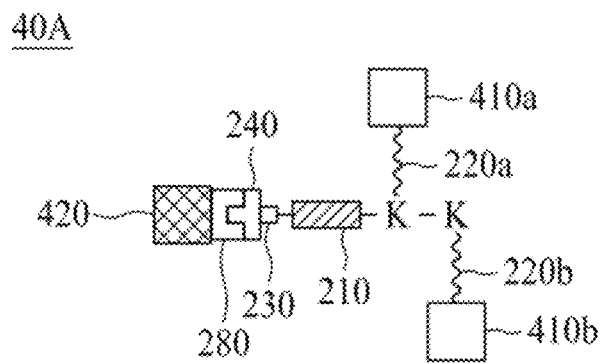
FIG. 4A to FIG. 4C are schematic diagrams illustrating linker units comprising different functional elements according to some embodiments of the present disclosure.

Reference is now made to FIG. 4A. Other than the features discussed hereafter, FIG. 4A is quite similar to FIG. 2A. First, the linker unit 40A has two first elements 410a and 410b respectively linked to the linking arms 220a and 220b. Second, there is a cyclooctene group 240 at the N-terminus of the core, and accordingly, a second element having a cyclooctene-reactive group (e.g., a tetrazine group 280) may be linked to the cyclooctene group 240 via the iEDDA reaction.

Figure 4B:
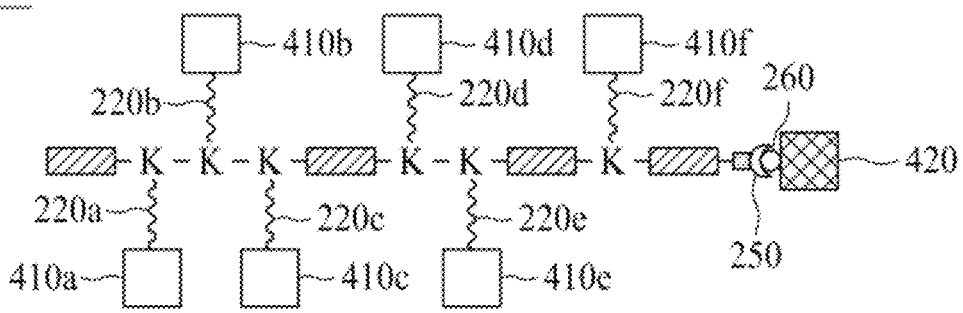

FIG. 4B provides an alternative example, in which the linker unit 40 has a similar structure with the linker unit 20E of FIG. 2E, except that an azide group 250 is present at the C-terminus of the core, rather than the tetrazine group 280. In addition, six first elements 410a-410f are respectively linked to the linking arms 220a-220f, and a second element having an alkyne group 260 is linked to the azide group 250 via the CuAAC reaction.

Alternatively, the linker unit may have two conjugating groups respectively present at the N- and C-terminus thereof. As mentioned above, when the first conjugating group is the azide, alkyne or cyclooctyne group, then the second conjugating group is preferably the tetrazine or cyclooctene group. Accordingly, two functional elements can be respectively linked to the core via SPAAC and iEDDA reactions, or via CuAAC and iEDDA reactions. For example, a second element having a cyclooctyne-reactive group (e.g., an azide group) can be linked to the first coupling group via the SPAAC reaction; while a third element having an alkyne-reactive group (e.g., an azide group), a tetrazine-reactive group (e.g., a norbornene or a TCO group), or a cyclooctene-reactive group (e.g., a tetrazine group) can be linked to the second coupling group via the CuAAC or the iEDDA reaction. Alternatively, a second element having a tetrazine-reactive group (e.g., a norbornene or a TCO group) or a cyclooctene-reactive group (e.g., a tetrazine group) can be linked to the first coupling group via the iEDDA reaction; and a third element having an azide-reactive group (e.g., an alkyne or a DBCO group), an alkyne-reactive (e.g., an azide group) or a cyclooctyne-reactive group (e.g., an azide group) can be linked to the second coupling group via the CuAAC or the SPAAC reaction.

Figure 4C:
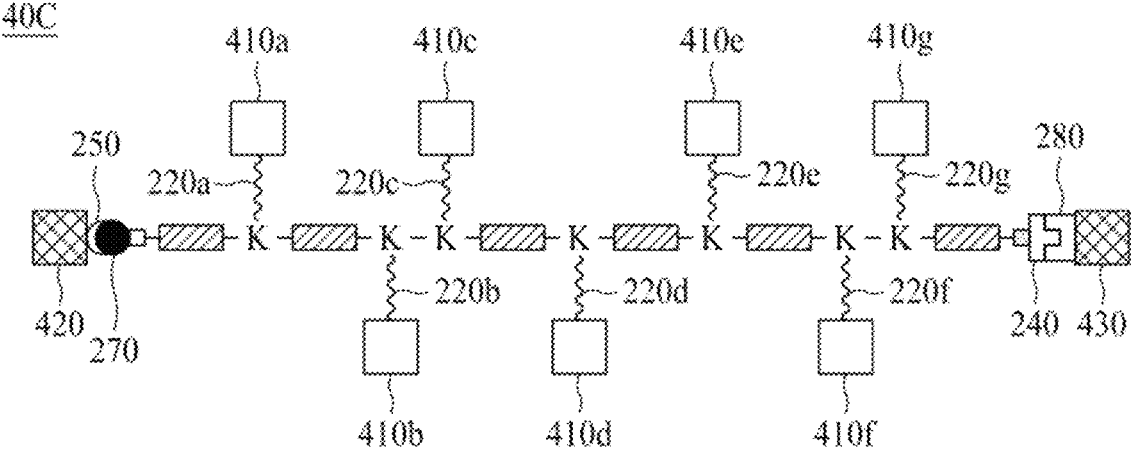

FIG. 4C provides an example of the present linker unit 40C, which comprises two conjugating groups respectively bonded to the second and third elements. The linker unit 40C has a similar structure with the linker unit 20F of FIG. 2F, except that the first elements 410a-410g are respectively linked to the linking arms 220a-220g, the second element 420 having an azide group 250 is linked to the cyclooctyne 270 via the SPAAC reaction, and the third element 430 having a tetrazine 280 is linked to the cyclooctene 240 via the iEDDA reaction.

When the release of effector elements at the targeted site is required, a cleavable bond can be installed in the linking arm. Such a bond is cleaved by acid/alkaline hydrolysis, reduction/oxidation, or enzymes. One embodiment of a class of cleavable PEG chains that can be used to form the coupling arm is NHS-PEG$_{2-20}$-S—S-maleimide (or vinyl sulfone), where S—S is a disulfide bond that can be slowly reduced, while the NHS group is used for conjugating with the amine group of the core, thereby linking the PEG chain onto the core. The maleimide (or vinyl sulfone) group at the free terminus of the linking arm may be substituted by an azide, alkyne, tetrazine, or strained alkyne group. According to some embodiments of the present disclosure, the linking arm is a PEG chain, which has 2-20 repeats of EG units with a disulfide linkage at the free terminus thereof (i.e., the terminus that is not linked with the core).

Scheme 9 provides the examples of sulfhydryl-reactive chemical groups (e.g., maleimides, vinyl sulfones and haloacetyls) that are amendable to the conjugation with sulfhydryl-containing molecules.

<<Scheme 9 Thiol-specific conjugation>>

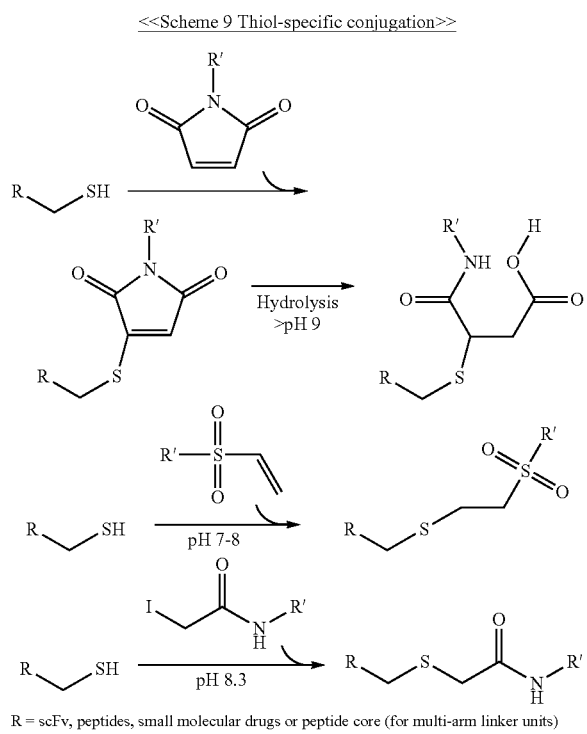

R = scFv, peptides, small molecular drugs or peptide core (for multi-arm linker units)

The maleimide group reacts specifically with sulfhydryl groups when the pH of the reaction mixture is between pH 6.5 and 7.5. The thio-succimide adduct is slightly reversible, with maleimide elimination occurring slowly under physiological condition. To avoid this retro-thiol-Michael reaction, the thio-succinimide adduct ring opening is conducted by base catalysis under mild condition (>pH 9.0), and the resulting product is chemically stable.

A vinyl sulfone group can selectively react with free thiol group. The reaction of Michael-type addition of the vinyl sulfone group is suitable for the selective modification of sulfhydryl groups of intended molecules under mild conditions (pH 7-8).

A direct $S_N2$ reaction of an iodoacetyl group with a sulfhydryl group yields a stable thioether linkage. The R group stands for scFv, peptides, small molecular drugs or peptide core (for multi-arm linker units), which contain sulfhydryl group.

Scheme 10 provides a method of conjugating a protein element to a core with hydroxyl groups. Formation of the PEG linker (3) could be accomplished by a direct etherification of a hydroxyl-containing core (1) with a tosylate linking arm (2) under the condition of a stoichiometric amount of NaH with a catalytic amount of NaI. The desired etherified core with scFv (4) could be obtained by a further 1,4-addition of intermediate (3) with an scFv. The Y group is a maleimide or vinyl sulfone group, which reacts with the Y' group. Y' is an SH group of a protein element or an SH group or an NH$_2$ group of a peptide.

<<Scheme 10 A method of conjugating a protein element to a core with hydroxyl groups>>

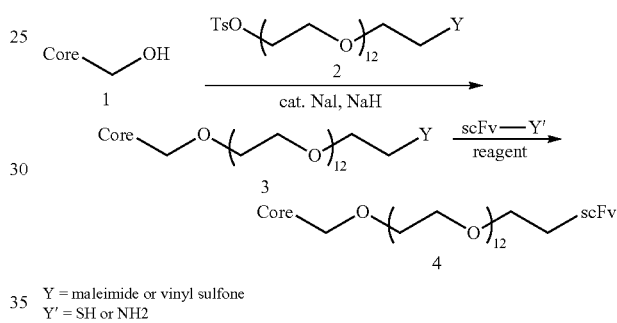

Y = maleimide or vinyl sulfone
Y' = SH or NH2

Scheme 11 provides an example of conjugating small molecular compounds to a core with hydroxyl groups. Various cross-coupling reactions could be utilized in the formation of a tosylate linking arm with drug (6) using the linking arm (5) and Y'-modified small molecular drug as the starting components. The desired etherified core with drug (7) could be obtained from an etherification of the hydroxy-containing core (1) with the tosylate linking arm with drug (6) under a condition of a stoichiometric amount of NaH with a catalytic amount of NaI. Y is a terminal functional group of the linking arm, which is selected from a group consisting of: TBDMS, hydroxyl, maleimide, NHS, vinyl sulfone, azide, alkyne, TCO, BCN, DBCO and tetrazine group. Y' is a terminal functional group of a modified small molecular drug, which is selected from a group consisting of: carboxylic acid, sulfhydryl, amine, NHS, vinyl sulfone, azide, alkyne, TCO, BCN, DBCO and tetrazine group. X represents the cross-linkage between two terminal functional groups Y and Y' after the coupling reaction.

<<Scheme 11 A method of conjugating small molecular element to a core with hydroxyl groups>>

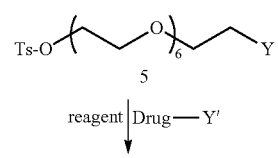

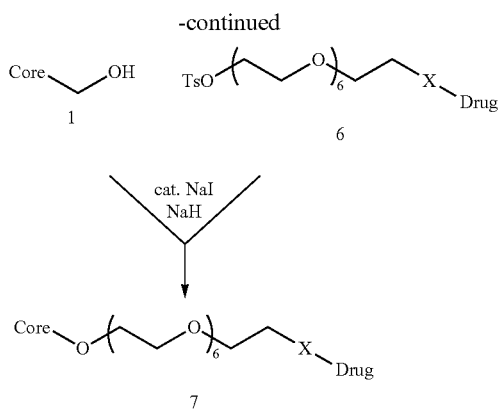

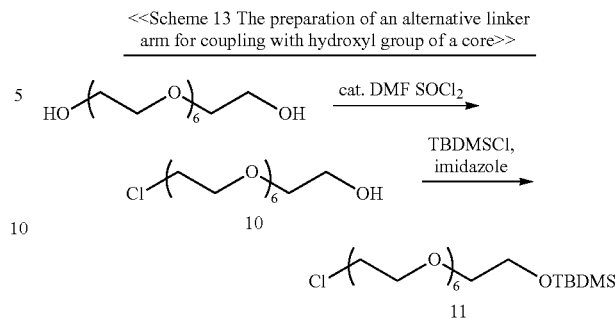

Scheme 14 provides a method of conjugating a protein element to a core with carboxylic acid groups. A direct esterification of a $CO_2H$-containing core (12) with linking arms having OH group (13) under a typical $DCC/NHS/Et_3N$ condition could deliver the corresponding esterified core (14). Next, a sulfa or aza-Michael addition of ester-modified core (14) with an scFv could deliver the desired esterified core with scFV (15). The other end of the linking arm has a Y group, which is a maleimide or vinyl sulfone group, which reacts with Y' group. Y' is a SH group of a protein element or a SH group or an $NH_2$ group of a peptide.

| Y = | Y' = | X = |
|---|---|---|
| OTBDMS | Carboxylic acid | Ester linkage |
| Hydroxyl | Carboxylic acid | Ester linkage |
| Vinyl sulfone | Sulfhydryl | Sulfonyl thioether linkage |
| Maleimide | Sulfhydryl | Succinimide thioether linkage |
| NHS | Amine | Amide linkage |
| Azide | Alkyne | 1,2,3-triazole linkage |
| Azide | DBCO | Triazole linkage |
| Azide | BCN | Triazole linkage |
| TCO | Tetrazine | Dihydropyrazine |

Scheme 12 provides an example of the preparation of the linking arm $TsO-PEG_6-OTBDMS$ used in scheme 11. Hexaethylene glycol ($HO-PEG_6-OH$) is commercially available. A TsCl/NaOH-mediated monosulfonate formation of hexaethylene glycol could produce the tosylate linking arm 8 ($TsO-PEG_6-OH$). Further TBDMSCl/imidazole-mediated silyletherification of a tosylate linking arm (8) could deliver the desired linking arm with tosyl and OTBDMS protecting group (9) ($TsO-PEG_6-OTBDMS$).

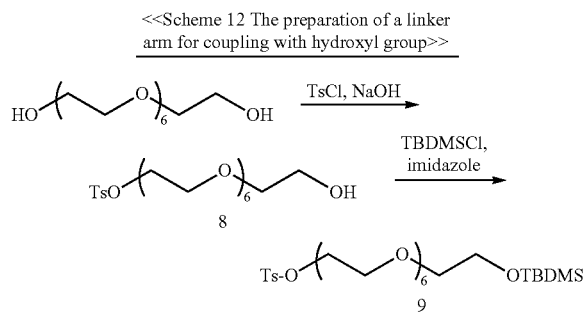

Scheme 13 provides an alternative example of the preparation of a linking arm $Cl-PEG_6-OTBDMS$ used in scheme 11. A $SOCl_2$-mediated monochlorination of hexaethylene glycol could give the ethanylchloride (10) ($Cl-PEG_6-OH$). Further TBDMS-Cl/imidazole-mediated silyletherification of the ethanylchloride (10) could deliver the desired linking arm (11) ($Cl-PEG_6-OTBDMS$). Abbreviations: TBAF, Tetrabutylammonium fluoride; DCC, N,N'-Dicyclohexylcarbodiimide; $Et_3N$, Triethylamine; TBDMS, tert-Butyldimethylsilyl; NHS, N-Hydroxy succinimide; Ts, p-Toluenesulfonyl; DMF, Dimethylformamide.

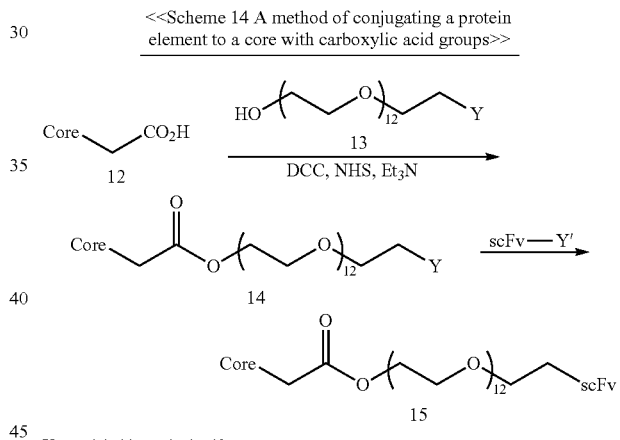

Y = maleimide or vinyl sulfone
Y' = SH or NH2

Scheme 15 provides an example of conjugating small molecular elements to a core with carboxylic acid ($CO_2H$) groups. A direct esterification of a $CO_2H$-containing core (12) with linking arms with OH group (16) under a typical $DCC/NHS/Et_3N$ condition could deliver the corresponding ester-modified core (17). Next, a conjugation of ester-modified core (17) with modified small molecular drugs under a suitable condition could deliver the desired ester-modified core with the drug (18). Y is a terminal functional group of linking arm, which is selected from a group consisting of: OTBDMS, hydroxyl, maleimide, NHS, vinyl sulfone, azide, alkyne, TCO, BCN, DBCO and tetrazine group. Y' is a terminal functional group of a modified small molecular drug, which is selected from a group consisting of: carboxylic acid, sulfhydryl, amine, NHS, vinyl sulfone, azide, alkyne, TCO, BCN, DBCO and tetrazine group. X represents the linkage between two terminal functional groups Y and Y' after coupling reaction.

<<Scheme 15 A method of conjugating small molecular elements to a core with carboxylic acid groups>>

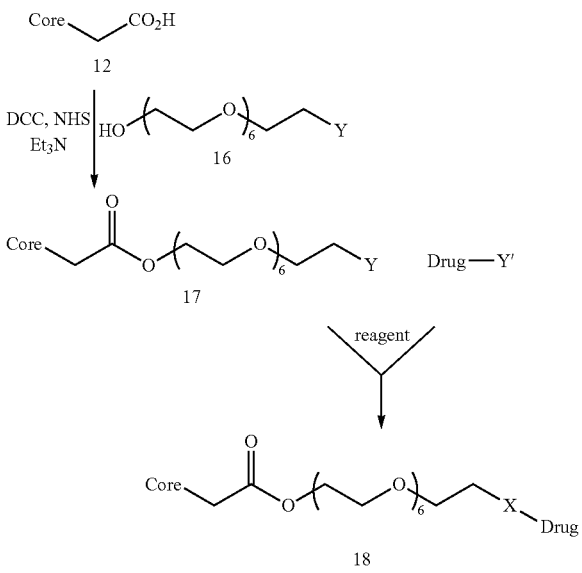

| Y = | Y' = | X = |
|---|---|---|
| OTBDMS | Carboxylic acid | Ester linkage |
| Hydroxyl | Carboxylic acid | Ester linkage |
| Vinyl sulfone | Sulfhydryl | Sulfonyl thioether linkage |
| Maleimide | Sulfhydryl | Succinimide thioether linkage |
| NHS | Amine | Amide linkage |
| Azide | Alkyne | 1,2,3-triazole linkage |
| Azide | DBCO | Triazole linkage |
| Azide | BCN | Triazole linkage |
| TCO | Tetrazine | Dihydropyrazine |

Scheme 16 provides an example of the preparation of a linking arm TsO-PEG$_6$-OH used in scheme 15. In this example, a TsCl/NaOH-mediated monosulfonate formation of hexaethylene glycol (HO-PEG$_6$-OH) could produce the tosylate linking-arm (8) (TsO-PEG$_6$-OH). An alternative example of the preparation of the linking arm Cl-PEG$_6$-OTBDMS is shown in scheme 17. In this example, A SOCl$_2$-mediated monochlorination of hexaethylene glycol (HO-PEG$_6$-OH) could give the ethanylchloride (10) (Cl-PEG$_6$-OH). Abbreviations: TBAF, Tetrabutylammonium fluoride; DCC, N,N'-Dicyclohexylcarbodiimide; Et$_3$N, Triethylamine; NHS, N-Hydroxysuccinimide; Ts, p-Toluenesulfonyl; DMF, Dimethylformamide.

<< Scheme 16 Preparation of a linking arm for coupling with carboxylic acid group>>

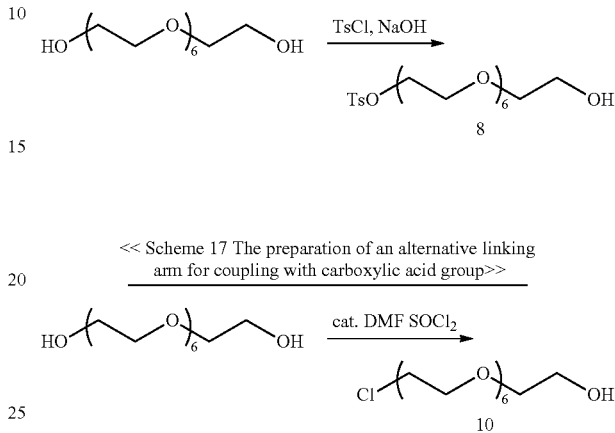

<< Scheme 17 The preparation of an alternative linking arm for coupling with carboxylic acid group>>

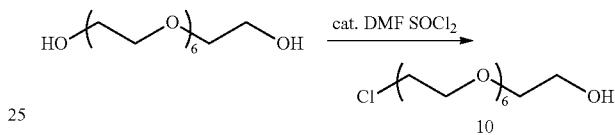

Scheme 18 illustrates the preparation of a linker arm and its conjugation to the OH groups of serine residues in a peptide core. The process to prepare HO-PEG$_{12}$-Cl (19) is similar to that described in scheme 17. A formation of HO-PEG$_{12}$-vinyl sulfone (20) could be accomplished by reacting HO-PEG$_{12}$-Cl 19 with sodium vinyl sulfinate. A TsCl/Et$_3$N-mediated monosulfonate formation of HO-PEG$_{12}$-vinyl sulfone (20) could produce the tosylate linking arm (21) (TsO-PEG$_{12}$-vinyl sulfone). In a separate reaction, the peptide core Ac-ZSZSZSC is reacted with a short linker Maleimide-PEG$_3$-DBCO to introduce DBCO for coupling with click reaction. The modified peptide core (22) is subsequently reacted with tosylate linking arm (21) (TsO-PEG$_{12}$-vinyl sulfone) under a condition of a stoichiometric amount of NaH with a catalytic amount of NaI, to produce the PEG linker-modified peptide core (23). Next, a sulfa-Michael addition of the PEG linker-modified peptide core (23) with an SH-containing scFv could deliver the desired the PEG linker-modified peptide core with scFv (24).

<<Scheme 18 A method of conjugating linking arms to a peptide core with serine residues>>

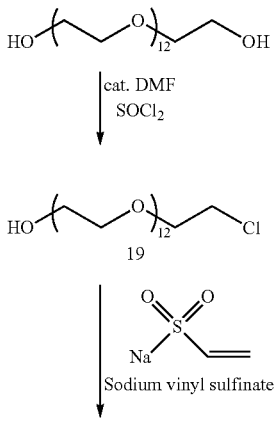

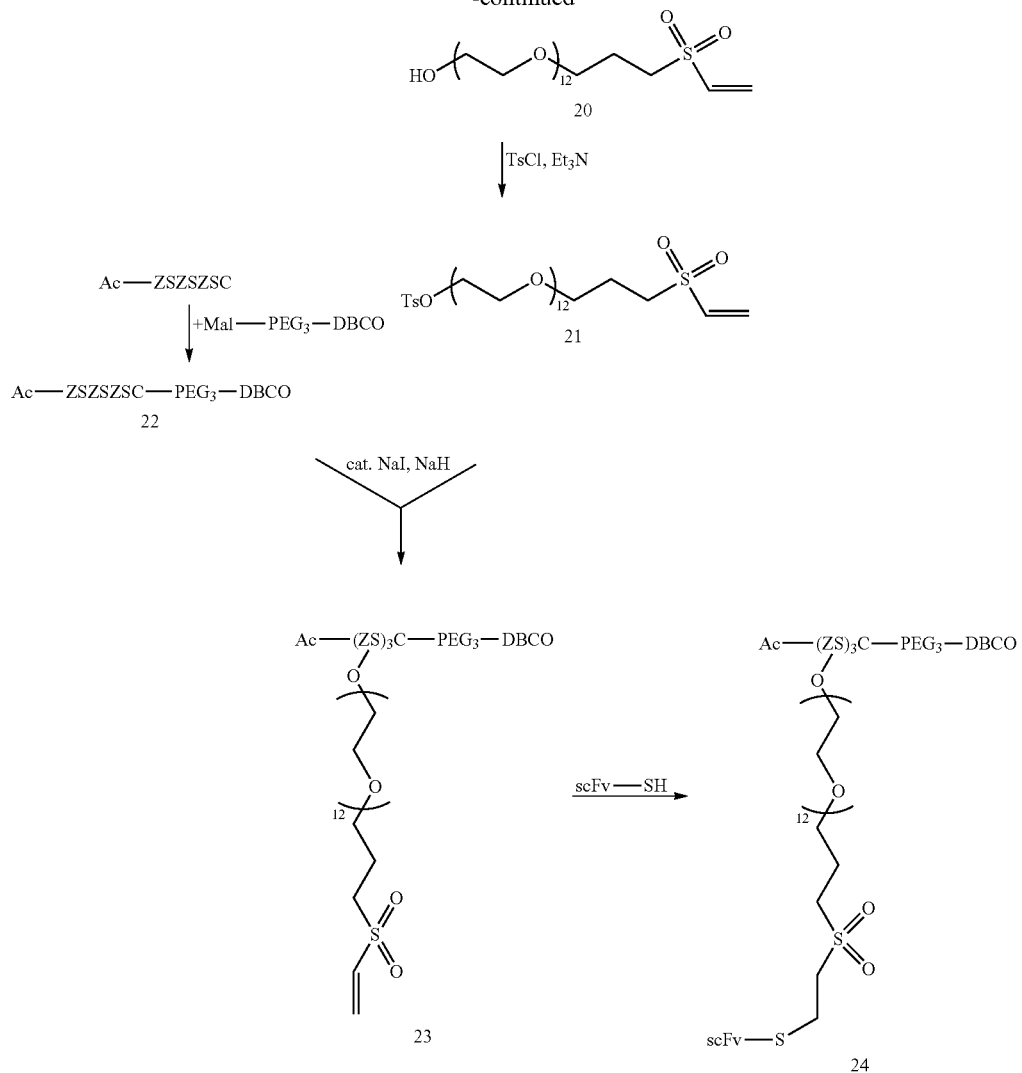

Scheme 19 illustrates a method of conjugating small molecular elements to a peptide core with serine residues. The process is similar to that described in scheme 17. In this case, the small drug molecules are conjugated to the linking arms before the linking arms are conjugated to the hydroxy groups of the peptide core. Various cross-coupling reactions could be utilized in a formation of a tosylate linking arm with drug (6) by reacting a tosylate linking arm (5) with the Y'-modified small molecular drug. Desired effector linker unit with drugs (28) could be obtained from an etherification of the Serine-containing peptide core (22) with the tosylate linking arm with drug (6) under a condition of a stoichiometric amount of NaH with a catalytic amount of NaI. Y is a terminal functional group of linking arm, which is selected from a group consisting of: OTBDMS, hydroxyl, maleimide, NHS, vinyl sulfone, azide, alkyne, TCO, BCN, DBCO and tetrazine group. Y' is a terminal functional group of a modified small molecular drug, which is selected from a group consisting of: carboxylic acid, sulfhydryl, amine, NHS, vinyl sulfone, azide, alkyne, TCO, BCN, DBCO and tetrazine group. X represents the linkage between two terminal functional groups Y and Y' after coupling reaction.

<<Scheme 19 A method of conjugating small molecular elements to a linker unit of peptide core with serine residues>>

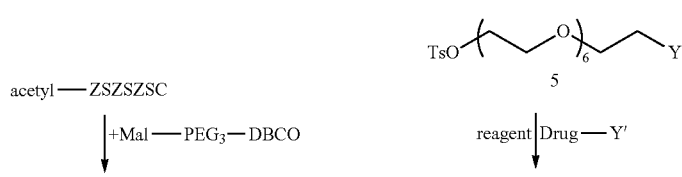

-continued

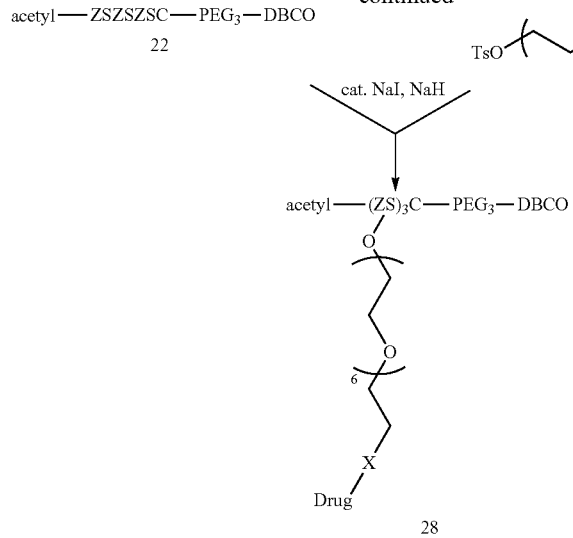

| Y= | Y'= | X= |
|---|---|---|
| OTBDMS | Carboxylic acid | Ester linkage |
| Hydroxyl | Carboxylic acid | Ester linkage |
| Vinyl sulfone | Sulfhydryl | Sulfonyl thioether linkage |
| Maleimide | Sulfhydryl | Succinimide thioether linkage |
| NHS | Amine | Amide linkage |
| Azide | Alkyne | 1,2,3-triazole linkage |
| Azide | DBCO | Triazole linkage |
| Azide | BCN | Triazole linkage |
| TCO | Tetrazine | Dihydropyrazine |

I-(ii) Functional Elements Suitable for Use in Multi-Arm Linker

In the case where the linker unit (or multi-arm linker) comprises only the first element but not the second and/or third element(s), the first element is an effector element that may elicit a therapeutic effect in a subject. On the other hand, when the present linker unit comprises elements in addition to first element(s), then at least one of the elements is an effector element, while the other may be another effector element, a targeting element, or an element capable of enhancing one or more pharmacokinetic properties of the linker unit (e.g., solubility, clearance, half-life, and bioavailability). For example, the linker unit may have two different kinds of effector element, one effector element and one targeting element or one pharmacokinetic property-enhancing element, two different kinds of targeting elements and one kind of effector element, two different kinds of effector elements and one kind of targeting element, or one kind of targeting element, one kind of effector element and one element capable of improving the pharmacokinetic property of the linker unit.

For the purpose of treating diffused tumor, one of the first and second elements of the present linker unit is an antibody fragment (e.g., an scFv) specific for a cell surface antigen, which is associated with and/or overexpressed on the diffused tumor; and the other of the first and second elements of the present linker unit is a cytotoxic drug or an antibody fragment specific for the cell surface antigen CD3 or CD16a. Preferably, the first element of the present linker unit is the antibody fragment specific for the tumor-associated antigen, and the second element of the present linker unit is the cytotoxic drug or the antibody fragment specific for the cell surface antigen CD3 or CD16a. According to the embodiments of the present disclosure, the cell surface antigen associated with and/or overexpressed on the diffused tumor is CD5, CD19, CD20, CD22, CD23, CD27, CD30, CD33, CD34, CD37, CD38, CD43, CD72a, CD78, CD79a, CD79b, CD86, CD134, CD137, CD138, or CD319. Optionally, the cytotoxic drug is selected from the group consisting of mertansine, auristatin, maytansine, doxorubicin, calicheamicin, and camptothecin.

The diffused tumors treatable by the present linker unit may be, acute lymphocytic leukemia (ALL), chronic lymphocytic leukemia (CLL), acute myelogenous leukemia (AML), chronic myelogenous leukemia (CML), Hodgkin lymphoma, non-Hodgkin lymphoma, or myeloma.

In one preferred embodiment, the present linker unit is employed to treat B-lymphocyte-derived lymphoma or leukemia, in which the first element is an antibody fragment (e.g., scFv) specific for CD5, CD19, CD20, CD22, CD23, CD30, CD37, CD79a, or CD79b; and the second element is the cytotoxic drug or an antibody fragment (e.g., scFv) specific for CD3 or CD16a.

In another preferred embodiment, the present linker unit is employed in the treatment of B-lymphocyte-derived lymphoma or leukemia, in which the first element is an antibody fragment specific for CD79a, and the second element is an antibody fragment specific for CD79b, or vice versa.

In still another preferred embodiment, the disease treated by the present linker unit is plasmacytoma or multiple myeloma, in which the first element is an antibody fragment specific for CD38, CD78, CD138, or CD319; and the second element is a cytotoxic drug or an antibody fragment specific for CD3 or CD16a.

In further another preferred embodiment, the present linker unit possesses an effect on T-cell derived lymphoma or leukemia, in which the first element is an antibody fragment specific for CD5, CD30, or CD43; and the second element is a cytotoxic drug or an antibody fragment specific for CD3 or CD16a.

In one preferred embodiment, the present linker unit is used to treat myelogenous leukemia, in which the first element is an antibody fragment specific for CD33 or CD34; and the second element is a cytotoxic drug or an antibody fragment specific for CD3 or CD16a.

Regarding the treatment of solid tumors, the first element of the present linker unit is a peptide hormone, a growth factor, or an antibody fragment specific for a tumor-associated antigen; and the second element is a cytotoxic drug, a toll-like receptor agonist, a chelator complexed with a radioactive nuclide, a cytokine, or an antibody fragment specific for a growth factor, a cell surface antigen, a hapten, or a cytokine.

The tumor-associated antigen is selected from the group consisting of human epidermal growth factor receptor (HER1), human epidermal growth factor receptor 2 (HER2), human epidermal growth factor receptor 3 (HER3), human epidermal growth factor receptor (HER4), carbohydrate antigen 19-9 (CA 19-9), carbohydrate antigen 125 (CA 125), mucin 1 (MUC 1), ganglioside GD2, ganglioside GD3, ganglioside GM2, fucosyl GM1, Neu5GcGM3, melanoma-associated antigen (MAGE), prostate-specific membrane antigen (PSMA), prostate stem cell antigen (PSCA), mesothelin, mucine-related Tn, Sialyl Tn, Lewis$^Y$, Sialyl Lewis$^Y$, Lewis$^A$, Lewis$^x$, heparin-binding epidermal growth factor (HB-EGF), Globo H, and stage-specific embryonic antigen-4 (SSEA-4).

The peptide hormone is selected from the group consisting of secretin, gastrin, cholecystokinin (CCK), gastrin-releasing polypeptide, glucagon-like polypeptide 1 (GLP-1), neuromedin, octreotide, thyroid-stimulating hormone (TSH), adrenocorticotropic hormone (ACTH), gonadotropin-releasing hormone (GnRH), and somatostatin.

The growth factor is selected from the group consisting of epidermal growth factor (EGF), mutant EGF, epiregulin, heparin-binding epidermal growth factor (HB-EGF), vascular endothelial growth factor A (VEGF-A), basic fibroblast growth factor (bFGF), and hepatocyte growth factor (HGF). In one working example, the first targeting element is EGF, mutant EGF, HB-EGF, VEGF-A, bFGF, or HGF. In another working example, the first effector element is an antibody fragment specific for EGF, mutant EGF, VEGF-A, bFGF, or HGF.

The cell surface antigen is PD-1, PD-L1, CTLA-4, CD3, CD16a, CD28, or CD134.

The hapten is dinitrophenol (DNP), trinitrophenol (TNP), dansyl, penicillin, p-aminobenzoic acid, or a short peptide having an amino acid sequence of SEQ ID NO: 23.

The cytokine is IL-2, IL-10, IL-12, IFN-α, IFN-γ, TGF-β, or TNF-α. Preferably, the second element is a non-neutralizing antibody fragment specific for the cytokine selected from the group consisting of IL-2, IFN-α, IFN-γ, and TNF-α.

As would be appreciated, the cytotoxic drug exhibiting a cytotoxic effect on tumor cell can be anti-estrogens (e.g., tamoxifen, raloxifene, and megestrol), LHRH agonists (e.g., goscrclin and leuprolide), anti-androgens (e.g., flutamide and bicalutamide), photodynamic therapies (e.g., vertoporfin, phthalocyanine, photosensitizer Pc4, and demethoxy-hypocrellin A), nitrogen mustards (e.g., cyclophosphamide, ifosfamide, trofosfamide, chlorambucil, estramustine, and melphalan), nitrosoureas (e.g., carmustine and lomustine), alkylsulphonates (e.g., busulfan and treosulfan), triazenes (e.g., dacarbazine, temozolomide), platinum containing compounds (e.g., cisplatin, carboplatin, oxaliplatin), vinca alkaloids (e.g., vincristine, vinblastine, vindesine, and vinorelbine), taxoids (e.g., paclitaxel, docetaxeal, and taxol), epipodophyllins (e.g., etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonucleotide reductase inhibitors (e.g., hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, peplomycin), anthracycline (e.g., daunorubicin, doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), imatinib, thalidomide, lenalidomide, tyrosine kinase inhibitors (e.g., axitinib, bosutinib, cediranib, dasatinib, erlotinib, gefitinib, imatinib, lapatinib, lestaurtinib, neratinib, nilotinib, semaxanib, sunitinib, toceranib, vandetanib, vatalanib, rituximab, nilotinib, sorafenib, everolimus, temsirolimus, proteasome inhibitors (e.g., bortezomib), mTOR inhibitors (e.g., rapamycin, temsirolimus, everolimus, and ridaforolimus), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, or hexamethyl melamine. According to one specific embodiment of the present disclosure, the cytotoxic drug is mertansine, auristatin, maytansine, doxorubicin, calicheamicin, or camptothecin.

The toll-like receptor agonist is lipoteichoic acid, glucan, motolimod, imiquimod, resiquimod, gardiquimod, CpG oligodeoxynucleotide (CpG DON), lipopolysaccharide (LPS), monophosphoryl lipid A, or zymosan.

The solid tumor treatable by the present method may be melanomas, esophageal carcinomas, gastric carcinomas, brain tumor, small cell lung cancer, non-small cell lung cancer, bladder cancer, breast cancer, pancreatic cancer, colon cancer, rectal cancer, colorectal cancer, renal cancer, hepatocellular carcinoma, ovary cancer, prostate cancer, thyroid cancer, testis cancer, or head and neck squamous cell carcinoma.

I-(iii) Use of Multi-Arm Linker

The present disclosure also pertains to method for treating various diseases (e.g., diffused tumors and solid tumors) using suitable linker unit of the present disclosure. Generally, the method comprises the step of administering to a subject in need of such treatment an effective amount of the linker unit according to embodiments of the present disclosure.

Compared with previously known therapeutic constructs, the present linker unit discussed in Part I is advantageous in several points:

(1) The number of the functional elements may be adjusted in accordance with the needs and/or applications. The present linker unit may comprise two elements (i.e., the first and second elements) or three elements (i.e., the first, second, and third elements) in accordance with the requirements of the intended application (e.g., the disease being treated, the route of administration of the present linker unit, and the binding avidity and/or affinity of the antibody carried by the present linker unit). For example, when the linker unit is intended to be directly delivered into the tissue/organ, one element acting as the effector element may be enough, thus would eliminate the need of a second element acting as the targeting element. However, if the linker unit is intended to be delivered peripherally (e.g., oral, enteral, nasal, topical, transmucosal, intramuscular, intravenous, or intraperitoneal injection), it may be necessary for the linker unit to simultaneously comprise a targeting element that specifically targets the present linker unit to the lesion site (e.g., the tumor or the cancerous cell/tissue); and an effector element that exhibits a therapeutic effect on the lesion site. For the purpose of increasing the targeting or treatment efficacy or increasing the stability of the present linker unit, a third element (e.g., a second targeting element, a second effector element, or a PEG chain) may be further included in the present linker unit.

(2) The first element is provided in the form of a bundle. As described above, the number of the first element varies with the number of linking amino acid residues comprised in the core. As the number of linking amino acid residues in the core ranges from 2 to 20, accordingly at least two first elements may be comprised in each linker unit. Thus, instead of providing one single molecule (e.g., cytotoxic drug and antibody) as traditional therapeutic construct or method may render, the present linker unit is capable of providing more functional elements (either as targeting elements or as effector elements) at one time, thereby greatly improves the therapeutic effect.

(3) The linker unit can be efficiently linked to the functional element or another molecular construct (see, Part II below) via the conjugating group bonded thereto. The present core can be commercially synthesized. Alternatively, the present core can be easily prepared in accordance with procedures provided in Schemes 4-9, where the N-terminal 9-fluorenylmethoxycarbonyl (Fmoc) serving as a protecting group to protect the α-amine group of a synthetic polypeptide is replaced by the conjugating group (i.e., azide, alkyne, tetrazine, cyclooctene or cyclooctyne group). Additionally or alternatively, the conjugating group may be bonded to the polypeptide via reacting with the carboxyl group of the polypeptide. The thus-produced core comprises one or two conjugating groups, which serves as a connector to link functional elements (e.g., the present second and/or third element) and the core.

Part II Joint-Linker Molecular Constructs and Uses Thereof

In another aspect, the present disclosure is directed to a molecular construct comprising two or more linker units coupling to each other via their conjugating moiety; and the utility of such molecular construct. According to one embodiment of the present disclosure, the molecular construct comprises a first linker unit and a second linker unit. In general, the first or second linker unit respectively have the structure described above in connection with other aspect(s) and embodiment(s) of the present disclosure. Specifically, the first linker unit comprises a first core, and two or more linking arms (hereinafter, the first linking arms) linked to the first core; the second linker unit comprises a second core, and two or more linking arms (hereinafter, the second linking arms) linked to the second core. As described in Part I of the present disclosure, the present core is characterized in having at least one conjugating moiety directly bonded at the N- and/or C-terminus thereof. According to certain embodiments of the present disclosure, each of the first and second cores has a conjugating moiety bonded therewith; for the sake of discussion, the conjugating moiety bonded to the first core is designated as the first moiety, and the conjugating moiety bonded to the second core is designated as the second moiety. First elements are conjugated to the first linking arms, and second elements are conjugated to the second linking arms. The first and second linker units are then coupled to each other via iEDDA, SPAAC, or CuAAC reaction occurred between the first and second conjugating moieties. The first and second elements have different functions and may be small molecules or peptides and proteins. For example, the first and second elements may be antibody fragments, such as svFv, sdAb, Fab, or F(ab)'2, or antibody mimetics, specific for two different antigens.

More specifically, each of the first and second conjugating moieties comprises a conjugating group at one terminus thereof and an amine or carboxyl group at the other terminus thereof, in which the conjugating group is selected from the group consisting of, azide, alkyne, tetrazine, cyclooctene and cyclooctyne groups. Accordingly, the conjugating moiety may be bonded to the alpha-amine group of the N-terminal spacer via the carboxyl group. Alternatively, the conjugating moiety may be bonded to the carboxyl group of the C-terminal spacer via the amine group. The conjugating moiety bonded to the core thus has the conjugating group at the free-terminus thereof.

Optionally, the conjugating moiety further comprises a PEG chain having 2-10 repeats of EG units disposed between the conjugating group and the connecting group. For example, the PEG chain may have 4, 6, 7, or 8 repeats of EG unit.

Still optionally, one of the first and second linker units may further contain a third conjugating moiety. The third conjugating moiety may be used to couple with a third element (such as an antibody fragment or a long-chain PEG) or a third linker unit. In this case, the first and second linker units are coupled by click reaction. Subsequently, the third conjugating moiety of the joint first and second linker units is coupled with the third element or linker unit by different click reactions.

II-(i) Structure of Joint-Linker Molecular Construct

According to some embodiments of the present disclosure, the molecular construct comprises two linker units, and the linker units are coupled to each other via the CuAAC, SPAAC, or iEDDA reaction. In some embodiments, one of the linker units is linked with a plurality of first elements, which act as the targeting elements, and the other of the linker units is linked with a plurality of second elements, which act as the effector elements.

Figure 5A:
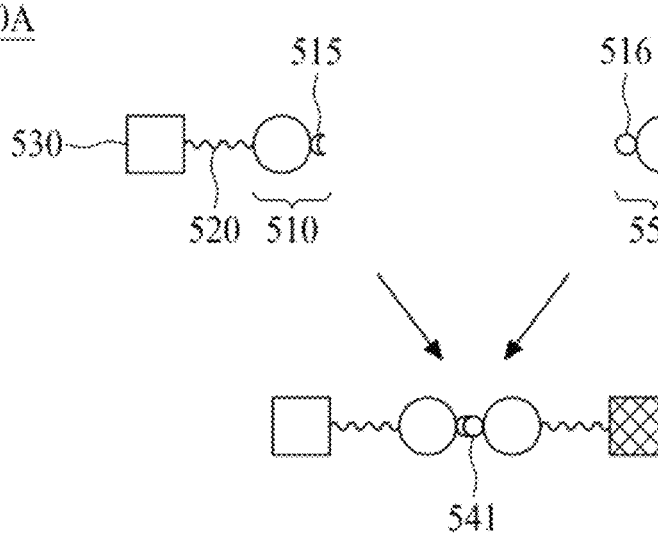
FIG. 5A to FIG. 5C are schematic diagrams that illustrate molecular constructs according to some embodiments of the present disclosure.
Figure 5B:
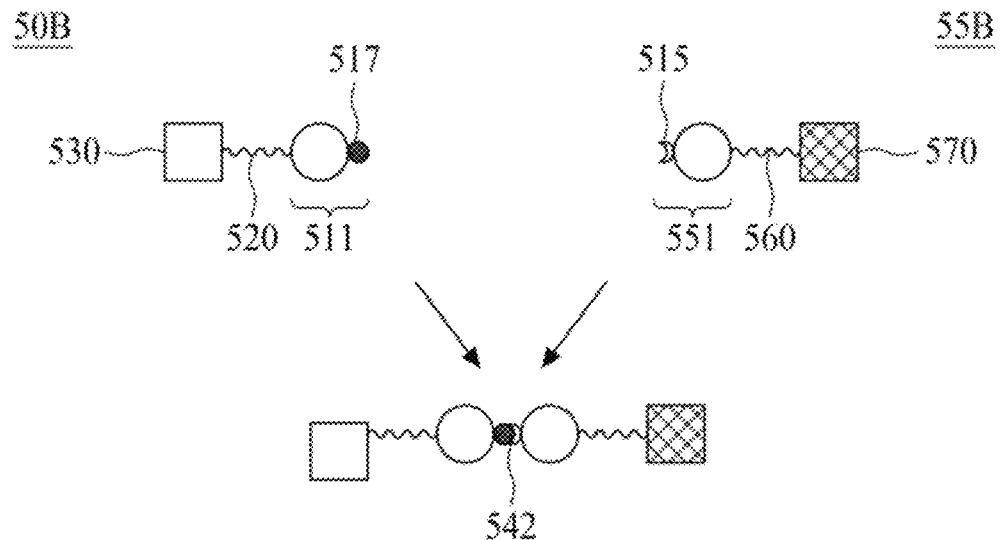
Figure 5C:
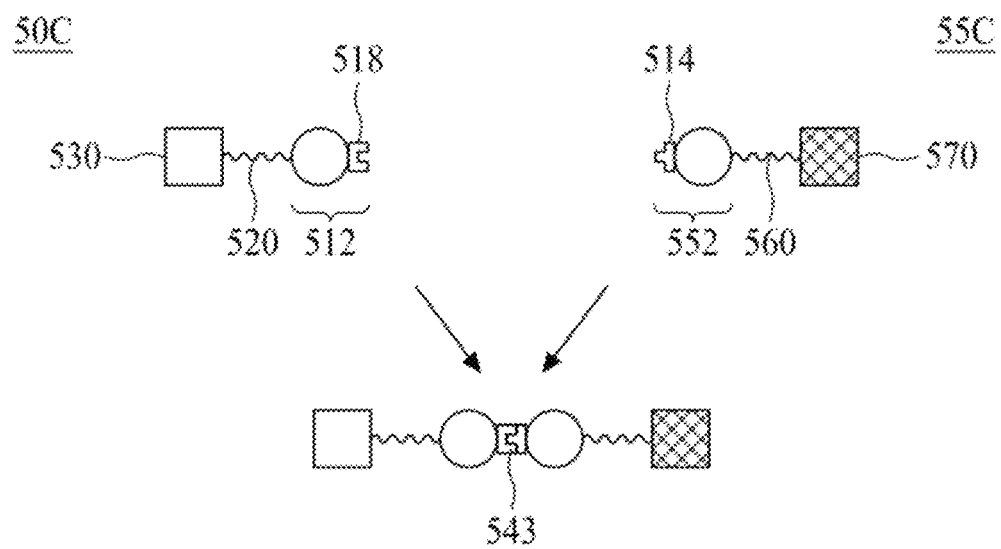

Reference is now made to FIGS. 5A-5C, which respectively depict the linkage between two linker units.

FIG. 5A depicts a molecular construct comprising two linker units 50A and 55A, which are coupled to each other via the CuAAC reaction. The first linker unit 50A comprises a first core 510, a linking arm 520 (i.e., the first linking arm) linked to the first core 510, and a functional element 530 (i.e., the first element) linked to the linking arm 520, in which the N- or C-terminal spacer of the first core 510 has a conjugating moiety with an azide group 515 bonded therewith. Similarly, the second linker unit 55A comprises a second core 550, a linking arm 560 (i.e., the second linking arm) linked to the second core 550, and a functional element 570 (i.e., the second element) linked to the linking arm 560, in which the N- or C-terminal spacer of the second core 550 has a conjugating moiety with an alkyne group 516 bonded therewith. Accordingly, the linker units 50A and 55A can be coupled together via the CuAAC reaction occurred between the azide group 515 and the alkyne group 516. The symbol 541 as depicted in FIG. 5A represents the chemical bond formed by the CuAAC reaction.

FIG. 5B provides another example of the present molecular construct, in which the N- or C-terminal spacer of the first core 511 has a conjugating moiety with a cyclooctyne group 517 bonded therewith, and the N- or C-terminal spacer of the second core 551 has a conjugating moiety with an azide group 515 bonded therewith. Then, the linker units 50B and 55B can be coupled to each other via the SPAAC reaction occurred between the cyclooctyne group 517 and the azide group 515. The symbol 542 as depicted in FIG. 5B represents the chemical bond formed by the SPAAC reaction.

Alternatively, the first and second linker units may be coupled together via the iEDDA reaction. Reference is now made to FIG. 5C. The linker units 50C and 55C respectively have a similar structure with the linker units 50A/50B and 55A/55B, except that the cores 512 and 552 respectively have a conjugating moiety with a tetrazine group 518 and a conjugating moiety with a cyclooctene group 514 bonded therewith. The linker units 50C and 55C can be coupled to each other via the iEDDA reaction occurred between the tetrazine group 518 and the cyclooctene group 514. The symbol 543 as depicted in FIG. 5C represents the chemical bond formed by the iEDDA reaction.

Preferably, when at least one of the first and second linking arms is linked to the functional element via the CuAAC or SPAAC reaction, then the first and second linker units are coupled to each other via the iEDDA reaction. Alternatively, when at least one of the first and second linking arms is linked to the functional element via the iEDDA reaction, then the first and second linker units are coupled to each other via the CuAAC or SPAAC reaction.

Compared with other therapeutic constructs, the present molecular construct is advantageous in at least the three following aspects:

(1) the linker units comprising a specified number and/or type of targeting/effector element can be prepared independently, which are then proceed to be coupled together via a suitable click chemistry reaction (such as, iEDDA, CuAAC, or the SPAAC reaction);

(2) the number and types of the targeting and/or effector elements may vary in accordance with the requirements of the intended application (e.g., the disease being treated, and the binding avidity and/or affinity of the targeting and/or effector element). The combination of the targeting and effector elements may be adjusted according to specific needs and/or applications. Each of the present targeting and effector elements may vary with such factors like particular condition being treated, the physical condition of the patient, and/or the type of disease being treated. A skilled person in the art may combine the most suitable targeting element and the most suitable effector element so as to achieve the best therapeutic effect. According to embodiments of the present disclosure, the targeting element may be a growth factor, a peptide hormone, a cytokine, or an antibody fragment; and the effector element may be an immunomodulant, a chelator complexed with a radioactive nuclide, a cytotoxic drug, a cytokine, a soluble receptor, or an antibody; and (3) compared with other coupling reactions, the iEDDA reaction or the SPAAC reaction is more efficient in terms of coupling any two linker units.

Figure 6:
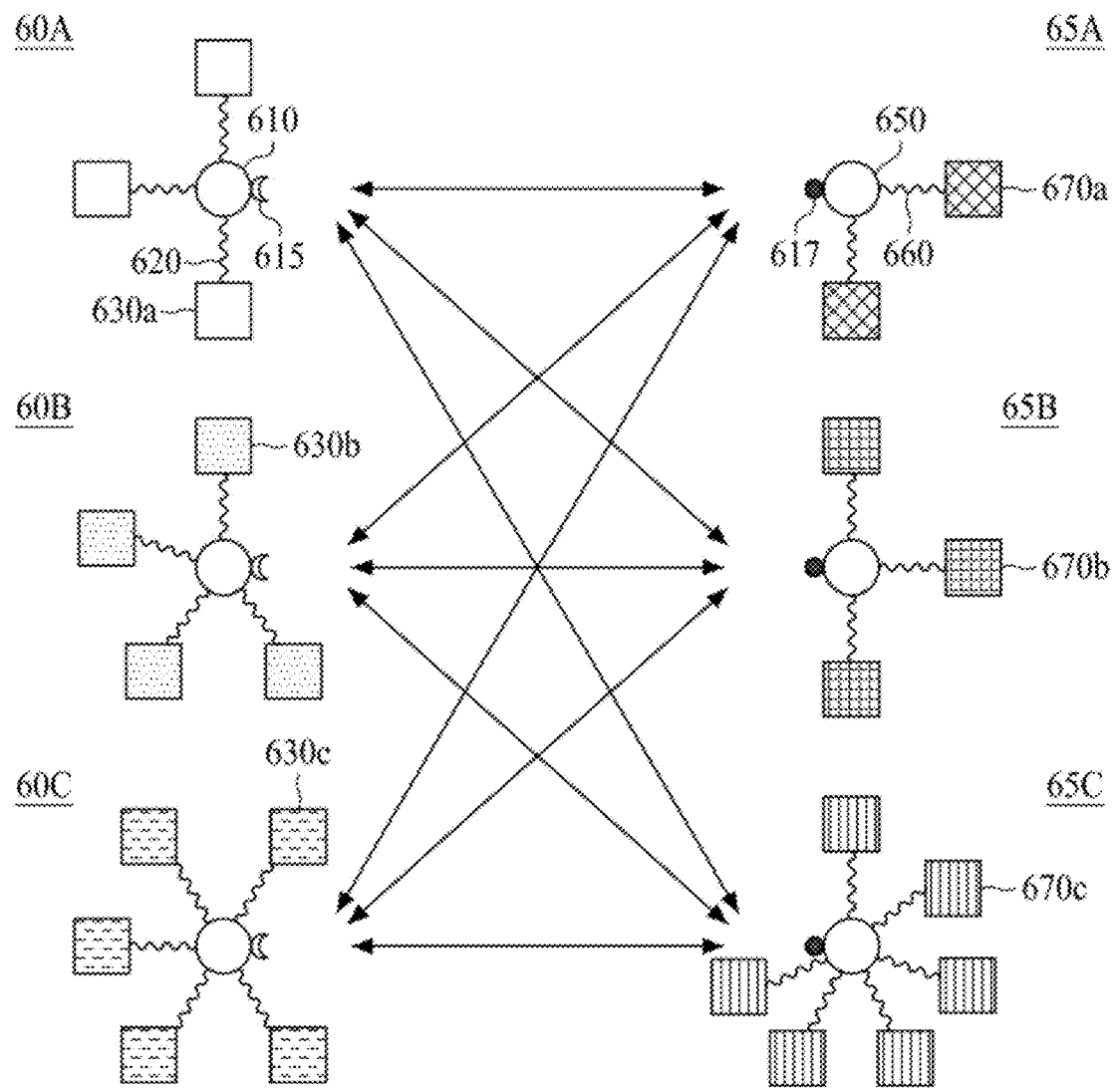
FIG. 6 is a schematic diagram that illustrates a molecular construct according to some embodiments of the present disclosure.

Reference is now made to FIG. 6, which illustrates six linker unit libraries that could be prepared independently. In this embodiment, Libraries 1-6 respectively comprise a plurality of linker units 60A, 60B, 60C, 65A, 65B, and 65C that are linked with functional elements. Each linker units 60A, 60B, and 60C are similar in structures; in which each of the linker units 60A, 60B, and 60C comprises one core 610 and a specified number of the linking arm 620, wherein the N- or C-terminus of the core 610 is bonded with a conjugating moiety having an azide group 615. For instance, the linker unit 60A comprises three linking arms 620, and accordingly, three targeting elements 630*a* can be respectively linked to the three linking arms 620. Similarly, four targeting elements 630*b* and five targeting elements 630*c* can be respectively linked to the linker units 60B and 60C. The targeting elements 630*a*, 630*b*, and 630*c* can be the same or different. As to the linker units 65A, 65B and 65C, each of these linker units comprises one core 650 and a specified number of the linking arm 660, in which the N- or C-terminus of the core 650 is bonded with a conjugating moiety with a cyclooctyne group 617. As depicted, two effector elements 670*a*, three effector elements 670*b*, and six effector elements 670*c* can be respectively linked to the linker units 65A, 65B and 65C. The effector elements 670*a*, 670*b*, and 670*c* can be the same or different. The Libraries 1-6 may be prepared independently. One skilled artisan may select the first linker unit from Libraries 1, 2 and 3, and the second linker unit from Libraries 4, 5, and 6, then proceed to couple the first and second linker units via the iEDDA reaction occurred between the azide group 615 and the cyclooctyne group 617, thereby producing a molecular construct having the specified number of targeting and effector elements.

As would be appreciated, the molecular construct may comprise three linker units, in which the first and second linker units are coupled to each other via the iEDDA reaction, and then, the third linker unit is coupled to the first or second linker unit via the CuAAC reaction. Alternatively, the first and second linker units are coupled to each other via the iEDDA reaction, and the third linker unit is coupled to the first or second linker unit via the SPAAC reaction. In some embodiments, the first, second, and third linker units respectively carry a plurality of first, second, and third elements, in which the first, second, and third elements may be the same or different.

Figure 7:
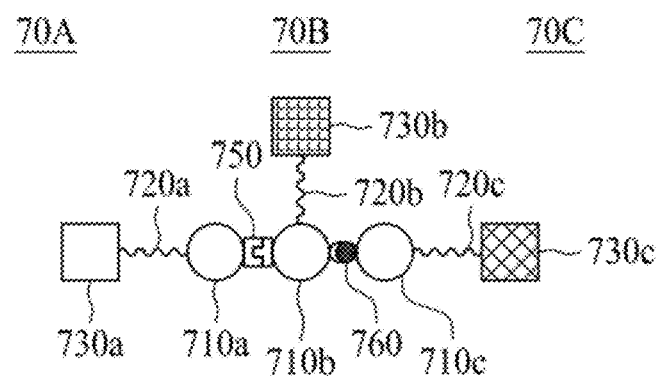
FIG. 7 is a schematic diagram illustrating a molecular construct comprising three linker units according to various embodiments of the present disclosure.

Reference is now made to FIG. 7, in which the linker units 70A, 70B and 70C are coupled together via the iEDDA and SPAAC reactions. Structurally, each of the linker units 70A, 70B, 70C comprises a core (710*a*, 710*b*, 710*c*), a linking arm (720*a*, 720*b*, 720*c*) linked to the core (710*a*, 710*b*, 710*c*), and a functional element (730*a*, 730*b*, 730*c*) linked to the linking arm (720*a*, 720*b*, 720*c*). For the purpose of coupling, the N- or C-terminus of the linker unit 70A has a conjugating moiety with a tetrazine group bonded therewith; the N- and C-termini of the linker unit 70B respectively have a conjugating moiety with a cyclooctene and a conjugating moiety with an azide groups bonded therewith; and the N- or C-terminus of the linker unit 70C has a conjugating moiety with a cyclooctyne group bonded therewith. Accordingly, the linker units 70A and 70B are coupled via the iEDDA reaction occurred between the tetrazine and cyclooctene groups, in which the symbol 750 depicted in FIG. 7 represents the chemical bond formed by the iEDDA reaction. On the other hand, the linker units 70B and 70C are coupled via the SPAAC reaction occurred between the azide and cyclooctyne groups, in which the symbol 760 depicted in FIG. 7 represents the chemical bond formed by the SPAAC reaction.

As would be appreciated, the numbers of each of the functional elements 730*a*, 730*b*, 730*c* respectively linked to the linker units 70A, 70B and 70C may be the same or different, depending on the intended use. With the library concept depicted in FIG. 6, the linker units respectively carrying different numbers and/or types of functional elements can be prepared independently as different libraries, and one skilled artisan may select and combine the desired linker units from the libraries in light of the intended application of the molecular construct.

Optionally, the present molecular construct may comprise a relatively long PEG chain connected to either the first or second core, so that the present molecular construct may be segregated further away from the reticuloendothelial system and attains a longer half-life after being administered to a subject. In the case where a protein is modified by a PEG chain to improve its pharmacokinetic properties and/or to decrease immunogenicity, PEG up to 20,000-50,000 daltons in length, is preferred. Accordingly, in one preferred embodiment of the present invention, linking arms of relatively shorter lengths are used to connect the targeting and effector elements, while a PEG chain of 20,000 to 50,000 daltons is connected to any of the linker units with the purpose of increasing in vivo half-life of the present molecular construct.

In some embodiments, multiple antibody fragments are used as the targeting and/or effector elements to construct the present molecular construct. The targeting element/effector element pharmaceuticals based on molecular constructs comprising antibody fragments should have longer in vivo half-lives than individual antibody fragments. For some clinical applications, much extended half-lives of the pharmaceuticals are desired, so as to eliminate the need of frequent administration of the drugs; in these cases, PEG chains that are 20,000 to 50,000 daltons by weight, may be used as the linking arms to link the antibody fragments that serve as targeting or effector elements. PEGs of these lengths have been used to modify a large number of therapeutic proteins to increase their half-lives.

Adopting a polypeptide as the core provides versatility to the present molecular construct, in which multiple copies or types of targeting/effector elements may be present in one construct, accordingly, enhanced specificity of drug delivery and potency in the intended target sites are achieved. A large number of configurations can be attained by employing the molecular construct comprising multiple linker units. A few non-limiting examples are: a first linker unit carrying three scFvs as targeting elements and a second linker unit carrying five therapeutic drug molecules; a first linker unit carrying three scFvs as targeting elements and a second linker unit carrying three scFvs effector elements; a first linker unit carrying two first scFvs (serving as first targeting elements), a second linker unit carrying two second scFvs (serving as second targeting elements), and a third linker unit carrying five therapeutic drug molecules; a first linker unit carrying 2 bi-scFv as targeting elements and a second linker unit carrying two scFvs as effector elements; or a first linker unit carrying three scFvs as targeting elements and a second linker unit carrying two scFvs as effector elements pluses one linking arm attached with a long PEG of 20,000-50,000 daltons for the purpose of increasing pharmacokinetic properties.

In some embodiments of this invention, a bi-functional PEG acting as a linking arm is used to link the antigen-binding fragments of antibodies (serving as the targeting or effector elements) to the amine groups located in the polypeptide core. Each PEG may have an NHS group at one end and maleimide and/or a vinyl sulfone group at the other end. The NHS group may couple with amine group in the polypeptide core, while the maleimide or vinyl sulfone group may couple with sulfhydryl group of a C residue of an antibody fragment, such as the scFv, bi-scFv, or Fab fragment of an antibody. The scFv and bi-scFv are engineered to have a polypeptide linker with terminal C residue at the C-terminal. Fab may be derived from a whole IgG by pepsin cleavage, and the free sulfhydryl groups are derived from the inter-chain disulfide bond by a mild reduction reaction.

When each of the targeting and effector elements is an scFv, and linking arms of 600 daltons (12 EG units) are used, a molecular construct with a total of six scFvs would have a molecular weight of about 170,000 daltons. A molecular construct with seven scFvs would have a molecular weight of about 200,000 daltons, and a molecular construct with eight scFvs would have a molecular weight of about 230,000 daltons. Most of the molecular constructs of this invention respectively have molecular weights less than 200,000 daltons, and a few molecular constructs have molecular weights range in 200,000-250,000 daltons.

When four different sets of scFv are to be carried in one molecular construct, it is preferable to have one linker unit carrying a joined single-chain, bi-specific scFv (bi-scFv), such as scFv1-scFv2 (e.g., specific for HER2 and HER3), and the other two linker units each carrying one scFv (i.e., scFv3 and scFv4 respectively). There are two approaches to construct a bi-specific scFv1-scFv2. In the "tandem" configuration, $V_L1-V_H1-V_L2-V_H2$ or $V_H1-V_L1-V_H2-V_L2$ is arranged; in the "diabody" configuration, $V_L2-V_L1-V_H1-V_H2$ or $V_H2-V_H1-V_L1-V_L2$ is arranged. Proper linkers with GGGGS (SEQ ID NO: 24) repeats or other sequences are placed between the immunoglobulin domains.

In our experience, a peptide or a PEG linker, which contains the maleimide and azide groups may become polymerized upon long-term storage, due to the automatic coupling reaction between the maleimide and azide groups. Therefore, it is preferable that each linker unit is prepared freshly and independently, and then proceeds to connecting the targeting or effector elements onto the linker units, as well as the coupling of the linker units through click reaction without delay. An alternative preferred embodiment is that the targeting elements and effector elements are both conjugated to linker units with alkyne groups, and the alkyne group in one of the linker units is then converted to azide with a short homo-bifunctional linker with azide at both ends. The linker units, one with alkyne and the other with azide, are then coupled via a click reaction. In a still another embodiment, the functional group at the free end of the linking arm is vinyl sulfone, which reacts with sulfhydryl group and form a stable covalent bond at regular physiological pH.

The preferred linking arms for this invention are PEG. The length of the linking arms is important for several considerations. It should be long enough to allow flexibility of the linked scFv or other types of functional elements to reach targeted antigenic sites on targeted cell surface without steric constraints; yet not long enough to cause intra-molecular and inter-molecular tangling of the linking arms and their linked scFv fragments or functional elements, or to unnecessarily increase the size of the whole molecular construct for hindering tissue penetration. Linking arms that are too long may also fail to pull antigen molecules to form compacted clusters, if such clusters are required to initiate signal-transducing process for apoptosis or other cellular effects. The optimal length of linking arms for different types of combinations of targeted antigens and their binding agents may be determined by any skilled artisan in the related field without undue experimentation. A linking arm of NHS-$(PEG)_{12}$-Maleimide (or vinyl sulfone) (approximately 500 daltons) is preferred in a number of molecular construct of this invention. A fully stretched $(PEG)_{12}$ has a length of 40-50 Å.

Applicable linking arms and coupling arms are not limited to PEG chains. Peptides comprising glycine, serine and other amino acid hydrophilic residues, and polysaccharides, and other biocompatible linear polymers, which are modified to contain NHS and maleimide (or vinyl sulfone) groups, can be used.

For certain therapeutic applications, it is desirable that the effector elements in the molecular constructs of this disclosure be released from the linking arms, so that they can get into cells at the targeted site, including cells bound by the targeting elements or surrounding cells, to cause pharmacological effects. In those cases, a cleavable bond is engineered in the linking arm. Cleavable bonds, which are susceptible for cleavage by hydrolysis, acid exposure, reduction, and enzymes, have been developed. For example, peptide segments susceptible to matrix metalloproteinases, which are present in inflammatory tissues, have been used in constructing therapeutic constructs. Peptide segments sensitive to cathepsins B or C, which are present in the endosomes or liposomes of various cells, have also been engineered in the linkers of antibody drug conjugates. One embodiment of the present invention is to use PEG linkers with S—S bond adjacent to the maleimide or vinyl sulfone group NHS-$PEG_{2-12}$-S—S-maleimide (or vinyl sulfone), wherein S—S is a disulfide bond, which can be slowly reduced.

According to some embodiments of the present disclosure, the targeting element described in above-mentioned embodiments is selected from the group consisting of a growth factor, a peptide hormone, a cytokine, and an antibody fragment; and the effector element is an immunomodulant, such as a toll-like receptor agonist, a chelator complexed with a radioactive nuclide, a therapeutic drug, a cytokine, a soluble receptor, or an antibody or antibody fragment.

In some optional embodiments, the antibody fragment is in the form of an antigen-binding fragment (Fab), a variable fragment (Fv), a single-chain variable fragment (scFv), a single domain antibody (sdAb), or a bi-specific single-chain variable fragment (bi-scFv). According to one embodiment, the bi-scFv is a bi-specific tandem scFv or a bi-specific diabody scFv.

In order to retain the diffusing ability of the molecular constructs, a molecular size smaller than 250,000 daltons is preferred. Thus, scFvs are preferred for most of the embodiments. At the DNA level, genes are constructed so that the $V_L$ and $V_H$ are linked as a single polypeptide in either order ($V_L$-$V_H$ or $V_H$-$V_L$) by a peptide linker of 10-25 amino acid residues with glycine and serine being the major residues. At the C-terminal, a short peptide extension with glycine and serine residues and a terminal residue C is engineered. The peptide extension may also comprise other hydrophilic and charged amino acid residues, such as H, K, R, N, and Q residues, which may help present the peptide extension and the terminal C residue in stretched configuration, so that the SH group of the C residue is freely accessible for conjugation with the linking arms of the multi-arm linker units. Recombinant scFv and bi-scFv can be produced in bacteria, such as E. coli and Pseudomonas putida, in yeast, such as Pichia pastoris, or in mammalian cells, such as CHO and HEK293 cell lines.

The inventors have produced a large number of IgG antibodies, Fab, scFv and various antibody fragments, Fc-based proteins, and other recombinant antibodies in HEK293 and CHO cell lines for experimentation in in vitro systems and in animal models. Also, we have developed cell lines for producing antibodies for human clinical trials. The HEK293 transient expression system can be conveniently employed to produce up to 1 gram of IgG or antibody fragments using a few flasks of 1-2 liters in the research laboratory. The antibody fragments to be used in the molecular constructs of this invention generally do not have a carbohydrate modification, and carbohydrate modification is not required for the binding activity of the scFv to their antigenic targets. Furthermore, only one disulfide bond and one terminal C are present in the antibody fragment. Therefore, small-scale bacterial expression systems have been developed as a manufacturing alternative for producing scFv. With E. coli, expression systems for recovering scFv in intracellular inclusion bodies, in periplasm, and/or in secreted form have also been employed. The scFv can be purified in most cases with an affinity column with Protein L, which interacts with $V_H$ of most κ light chain, or in other cases with ion-exchange columns.

The examples of this invention based on the joint-linker platform employ mainly scFv and Fab as the targeting and/or effector elements. However, specific binding molecules may also be screened from large libraries of binding molecules based on sdAb or other antibody fragments. Libraries of binding molecules, which are not based on immunoglobulin domains but resemble antibodies in having specific binding affinities to selected target molecules, include (1) aptamers, which are oligonucleotides or short peptides selected for binding to target molecules, (2) fynomers, which are small binding proteins derived from the human Fyn SH3 domain, (3) affimers, which are binding proteins derived from the cysteine protein inhibitor family of cystatins, and (4) DARPins (designed ankyrin repeat proteins), which are genetically engineered proteins with structures derived from the natural ankyrin proteins and consist of 3, 4, or 5 repeat motifs of these proteins. These antibody-mimetics have molecular weights of about 10K to 20K daltons.

II-(ii) Functional Elements Suitable for Use with Joint-Linker Molecular Construct As discussed above, the present joint-linker comprises at least two linker units, in which the first linker unit carries one or more targeting elements, and the second linker unit carries one or more effector elements or pharmacokinetic property-enhancing elements, and vice versa. The skilled artisan may select suitable functional elements as the targeting element, effector element and/or pharmacokinetic property-enhancing element in accordance with the first and second elements selected in Part I-(ii) of this specification so as to produce the desired effect.

II-(iii) Use of Joint-Linker Molecular Construct

The present disclosure also pertains to method for treating various diseases using the suitable joint-linker molecular construct. Generally, the method comprises the step of administering to a subject in need of such treatment an effective amount of the joint-linker molecular construct according to embodiments of the present disclosure.

As could be appreciated, examples of the functional elements described above in connection with other aspect(s) or embodiment(s) of the present disclosure are also applicable in the present molecular constructs, and these examples are not repeated herein for the sake of brevity.

However, for the purpose of illustration, the use of the present molecular construct in the treatment of various types of lung cancer is discussed here. To treat patients with various types of lung cancer, the effector element of the present linker unit or molecular construct to be administered may be any of, 1. Cytotoxic drugs—mertansine, monomethyl auristatin E (MMAE), pyrrolobenzodizepine (PBD), lenalidomide, pomalidomide, erybulin, tubulysin A, tubulysin B, doxorubicin, calicheamicin, and camptothecin;

2. Immunostulants—toll-like receptor agonists, monophosphoryl lipid A; or

3. Immune checkpoint inhibitors: antibodies, antibody fragments, or antibody mimetics specific for CTLA-4, PD-1, and PD-L1.

The following experimental examples are provided to elucidate certain aspects of the present invention and to aid those of skilled in the art in practicing this invention. These examples are in no way to be considered to limit the scope of the invention in any manner. Without further elaboration, it is believed that one skilled in the art can, based on the description herein, utilize the present invention to its fullest extent.

EXPERIMENTAL EXAMPLES

Example 1: Direct Synthesis of Peptide 1 to 4 as Peptide Cores

Four peptides containing a conjugating group that could be used as center cores for constructing multi-arm linker units were designed. Each of the conjugating group-containing peptides 1 to 4 (custom-made by ChinaPeptide Co., Ltd.; Shanghai, China) was synthesized directly by a standard solid-phase method and then purified with the reversed-phase high-performance liquid chromatography (HPLC) using Shimadzu Nexera-i LC-2040C 3D HPLC system to at least 95% purity. The reversed-phase HPLC used a Kromasil 100-5C18 column (250 mm×4.6 mm; 5 μm), with a mobile phase of acetonitrile and 0.1% trifluoroacetic acid, a linear gradient of 5% to 20% acetonitrile over 15 minutes, at a flow rate of 1.0 mL/min and a column temperature of 25° C.

Peptide 1 (purity: 95.52%) had the peptide sequence of SEQ ID NO: 1 (GGSGGSGGSKGSGSKGSK), in which both the N- and C-termini were chemically modified. In particular, the N-terminus of SEQ ID NO: 1 was modified by amidation with 4-pentynoic acid, whereas the C-terminus was esterified with methyl alcohol. Peptide 2 (purity: 97.05%) had the peptide sequence of SEQ ID NO: 2 (GGSGGSKGSKGSKGSKGSK) with the N and C-termini respectively modified by 2-azidoacetic acid and methyl alcohol. To prepare peptide 3 (purity: 98.71%), the peptide of SEQ ID NO: 3 (GSSGSSKGSGKGSGKGSGKGSGK) was subjected to N-terminal amidation with 3-butynoic acid and C-terminal primary amide formation by utilizing an amide resin. Similarly, for peptide 4 (purity: 95.95%), the peptide of SEQ ID NO: 4 (GSSGSSGSSGSKGSGSKGSGSK) was amidated with exo-5-norbornenecarboxylic acid at the terminus, and the C-terminus thereof was also modified by amidation.

The thus-synthesized peptides were respectively identified by electrospray ionization mass spectrometry (ESI-MS) (API 150 EX Applied Biosystems).

The present peptide 1 (SEQ ID NO: 1), as illustrated below, had a molecular weight (m.w.) of 1532.58 daltons.

The present peptide 2 (SEQ ID NO: 2), as illustrated below, had a molecular weight (m.w.) of 1734.84 daltons.

The present peptide 3 (SEQ ID NO: 3), as illustrated below, had a molecular weight (m.w.) of 2004.977 daltons.

The present peptide 4 (SEQ ID NO: 4), as illustrated below, had a molecular weight (m.w.) of 1935.98 daltons.

Figure 8A:
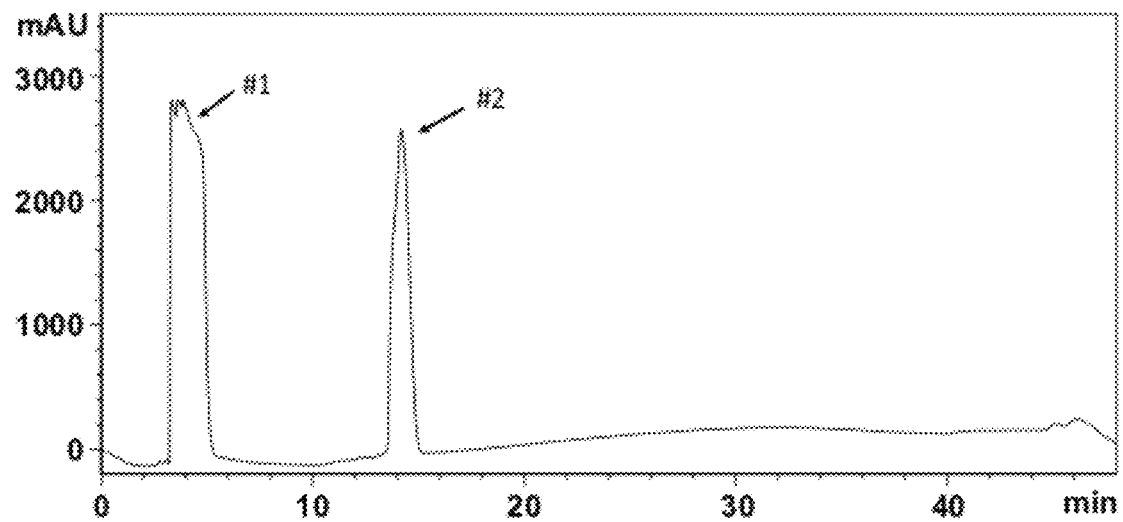
FIGS. 8A and 8B show the results of HPLC and mass spectrometry MALDI-TOF analysis of the norbornene-modified peptide 4 according to Example 1 of the present disclosure.
Figure 8B:
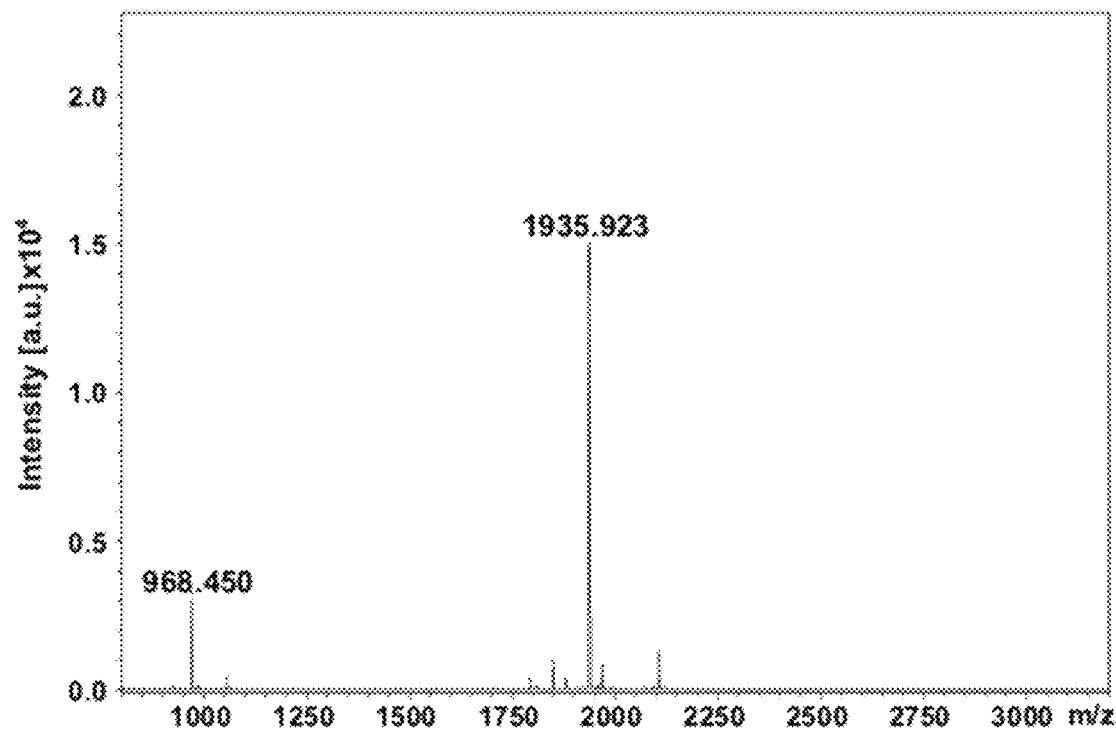

The purified sample of the norbornene-containing peptide 4 was analyzed using the reversed-phase analytical HPLC on a Supelco C18 column (250 mm×4.6 mm; 5 μm), with a mobile phase of acetonitrile and 0.1% trifluoroacetic acid, a linear gradient of 0% to 100% acetonitrile over 30 minutes, at a flow rate of 1.0 ml/min and a column temperature of 25° C., the ultraviolet (UV) absorbance at 210 nm ($OD_{210}$) was measured. FIG. 8A is the reversed-phase analytical HPLC profile of the present norbornene-containing peptide 4, which showed a peak of the norbornene-containing peptide 4 with a retention time of 14.17 minutes (arrow head #2; arrow head #1 was the peak of the eluted solvent). FIG. 8B shows the mass spectrometry MALDI-TOF result of the peptide 4. Unless indicated otherwise, all mass spectrometry analyses were performed by Mass Core Facility of Institute of Molecular Biology (IMB), Academia Sinica, Taipei, Taiwan; measurements were performed on a Bruker Autoflex III MALDI-TOF/TOF mass spectrometer (Bruker Daltonics, Bremen, Germany).

Example 2: Direct Synthesis of PEGylated Peptide 5 as Peptide Core

Peptide 5 (custom-made by Shanghai WuXi AppTech Co., Ltd., Shanghai, China), as illustrated below, was also synthesized directly using the standard solid-phase method, in which a PEGylated peptide having the sequence of SEQ ID NO: 5 (-Xaa$_4$-K-Xaa$_4$-K-Xaa$_4$-K-Xaa$_4$-K-Xaa$_4$-K) was modified by an azidoacetic acid at the N-terminus and by a methyl alcohol at the C-terminus. The inventors designed the peptides and outsourced the preparation of the two peptides to Shanghai WuXi AppTech Co., Ltd. (Shanghai, China).

Figure 9A:
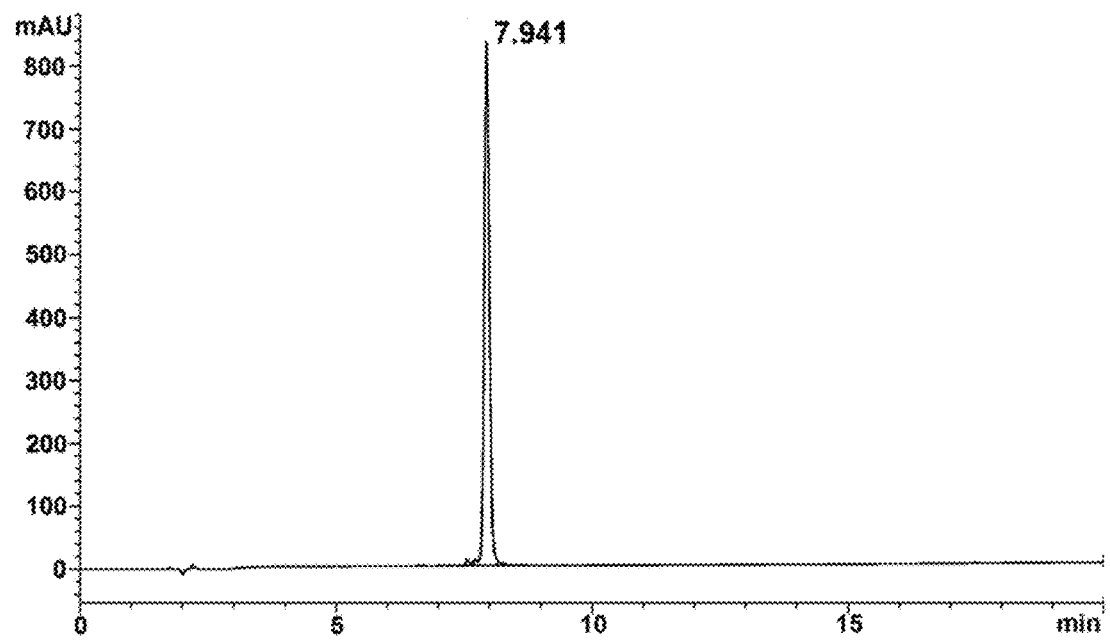
FIGS. 9A and 9B show the results of HPLC and mass spectrometry MALDI-TOF analysis of the azide-modified peptide 5 according to Example 2 of the present disclosure.

The azide-containing PEGylated peptide 5 was purified with reversed-phase HPLC using Agilent Nexera-i 1200 HPLC-BE system to 97.58% purity. The reversed-phase HPLC used a Gemini-NX C18 column (150 mm×4.6 mm; 5 μm), with a mobile phase of acetonitrile and 0.1% trifluoroacetic acid, a linear gradient of 10% to 40% acetonitrile over 20 minutes, at a flow rate of 1.0 mL/min and a column temperature of 25° C. FIG. 9A is the reversed-phase analytical HPLC profile of the azide-containing PEGylated peptide 5, which shows with the peak of the azide-containing PEGylated peptide 5 has a retention time of 7.941 minutes.

fied by a dibenzocyclooctyne-acid (DBCO-acid) at the N-terminus and amidated using an amide resin at the C-terminus. The peptide 7 serves as a center core, which has one DBCO group at the N-terminus thereof for the click reaction with an element or a linker unit.

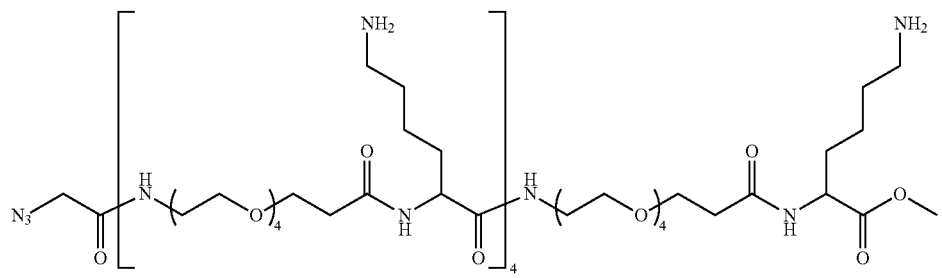

Figure 9B:
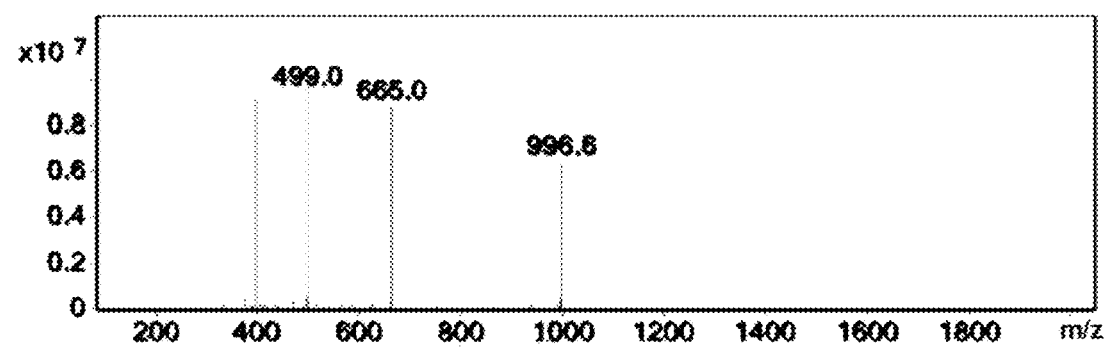

The identification of the azide-containing PEGylated peptide 5 as a core was carried out by ESI-MS. FIG. 9B shows the present PEGylated peptide 5 was a peptide core carrying one coupling arm with an azide group. The result of ESI-MS indicated that the present molecular construct had a m.w. of 996.6 daltons.

Example 3: Direct Synthesis of Peptide 6 to 10 as Peptide Cores

Five peptides containing a conjugating group that could be used as center cores for constructing multi-arm linker units were designed. Each of peptides 6 to 10 was synthesized directly by a standard solid-phase method (peptides 6 and 10, custom-made by ChinaPeptide Co., Ltd.; peptides 7 to 9, custom-made by NingBo KareBay Co., Ltd., Ningbo, China).

Peptide 6 (illustrated below) also had the amino acid sequence of SEQ ID NO: 2 (GGSGGSKGSKGSKGSKGSK), yet the N-terminus thereof was modified with azido-Xaa$_5$-acid, whereas the C-terminus was modified by C-terminal amidation. As a center core, peptide 6 had five K residues separated by a spacer having the sequence of GS, and the azido group at the N-terminus can be subjected to a click reaction with an element or another linker unit having a corresponding reactive group.

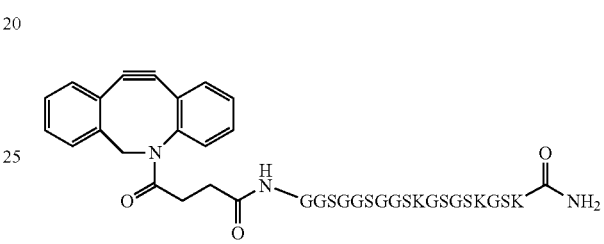

Figure 10A:
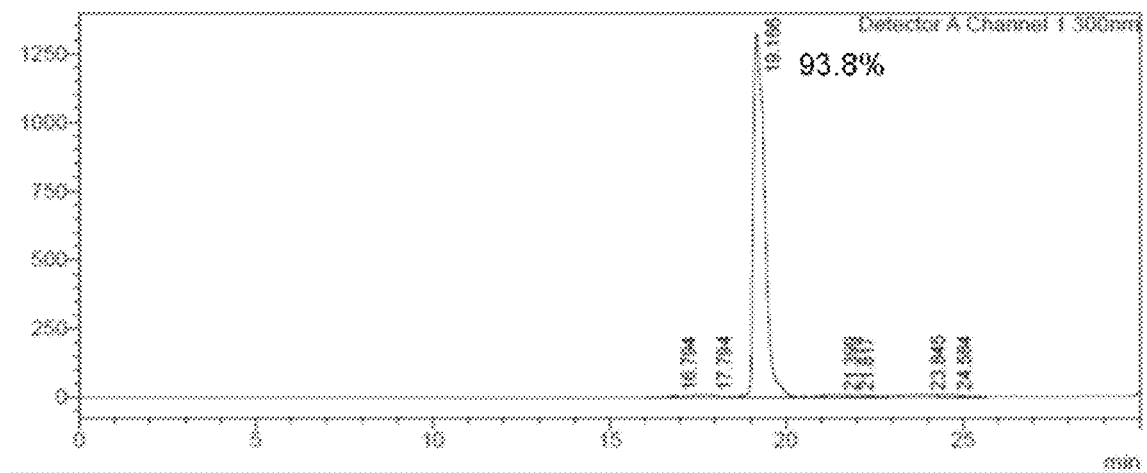
FIGS. 10A and 10B show the results of HPLC and mass spectrometry MALDI-TOF analysis of the DBCO-modified peptide 7 according to Example 3 of the present disclosure.

The purified sample of the DBCO-containing peptide 7 was analyzed by reversed-phase analytical HPLC on a Supelco C18 column (250 mm×4.6 mm; 5 μm), using a mobile phase of acetonitrile and 0.1% trifluoroacetic acid, a linear gradient of 0% to 73% acetonitrile over 30 minutes, at a flow rate of 1.0 ml/min and a column temperature of 25° C.; the UV absorbance was measured at 300 nm. FIG. 10A shows the reversed-phase analytical HPLC profile of the DBCO-containing peptide 7, which has a peak with a retention time of 19.166 minutes.

Figure 10B:
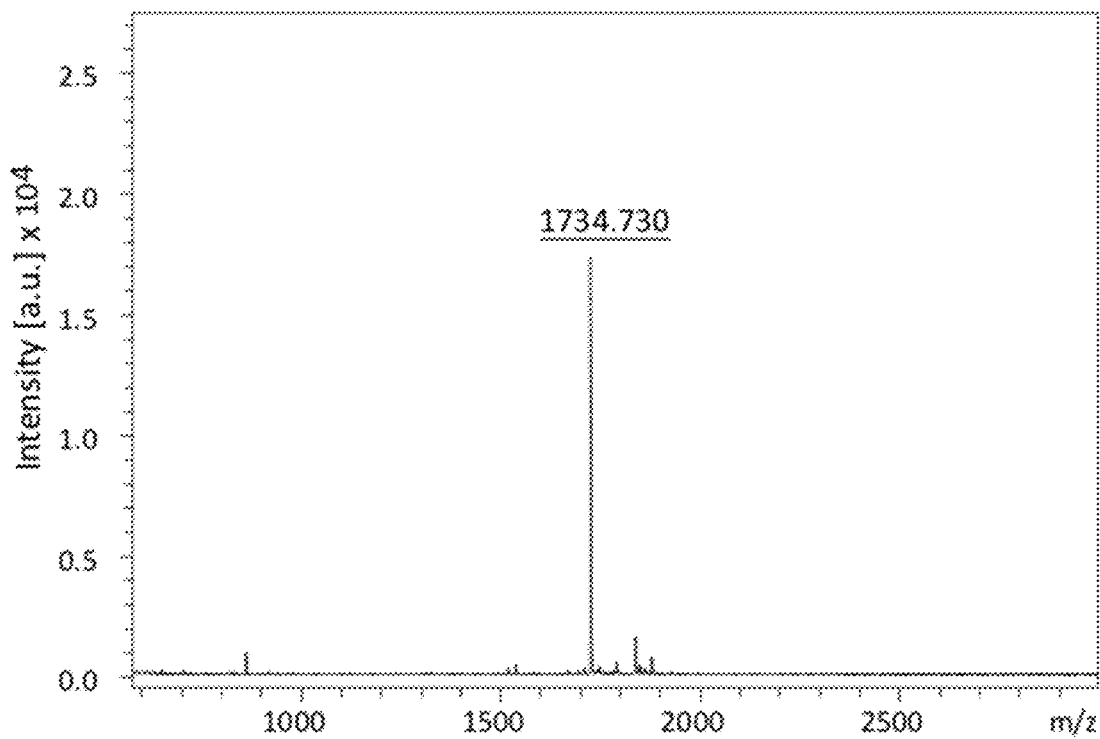

The thus-synthesized DBCO-containing peptide 7 was examined using MALDI-TOF. FIG. 10B shows that the DBCO-containing peptide 7 had a molecular weight of 1734.73 daltons.

As illustrated below, peptide 8 having the sequence of SKSKSK (SEQ ID NO: 6) was modified by an azido-Xaa$_6$-

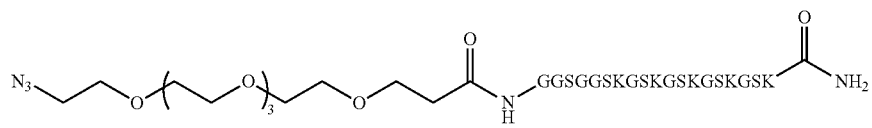

The purified sample of peptide 6 was analyzed by reversed-phase analytical HPLC on a Kromasil 100-5 C18 column (250 mm×4.6 mm; 5 μm), using a mobile phase of acetonitrile and 0.1% trifluoroacetic acid, a linear gradient of 15% to 30% acetonitrile over 12 minutes, at a flow rate of 1.0 ml/min and a column temperature of 35° C.

The thus-synthesized peptide 6 was examined using ESI-MS. The result of ESI-MS indicated that the present molecular construct had a molecular weight of 1954.15 daltons.

As illustrated below, the peptide 7 having the sequence of GGSGGSGGSKGSGSKGSK (SEQ ID NO: 1) was modiacid at the N-terminus and amidated by an amide resin at the C-terminus. The peptide 8 (as illustrated below) comprises three K residues separated by the same spacer sequence (i.e., a single S residue). This azide-containing peptide 8 had a m.w. of 1024.17 daltons.

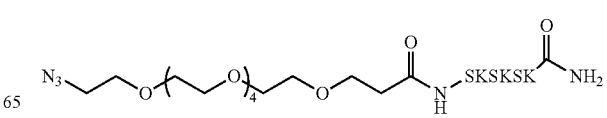

Figure 11A:
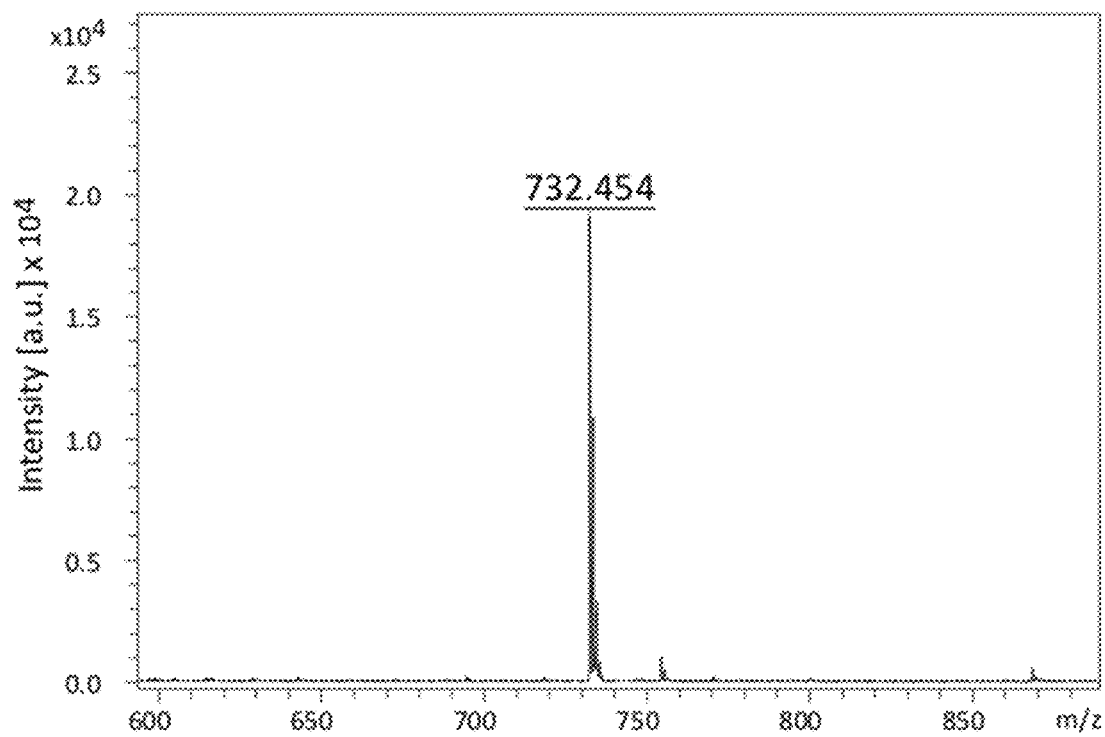
FIGS. 11A and 11B respectively show the analysis results of the alkyne-modified peptide 9 and the azido-modified peptide 10 according to Example 3 of the present disclosure.

As illustrated below, the peptide 9 has the sequence of KKK (that is, there is no spacer between the K residues), in which the N-terminus was modified by a propargyl-Xaa$_6$ acid, and the C-terminus thereof was modified with C-terminal primary amidation. The data in FIG. 11A indicates that the alkyne-peptide 9 had a m.w. of 732.454 daltons.

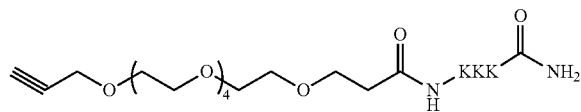

Figure 11B:
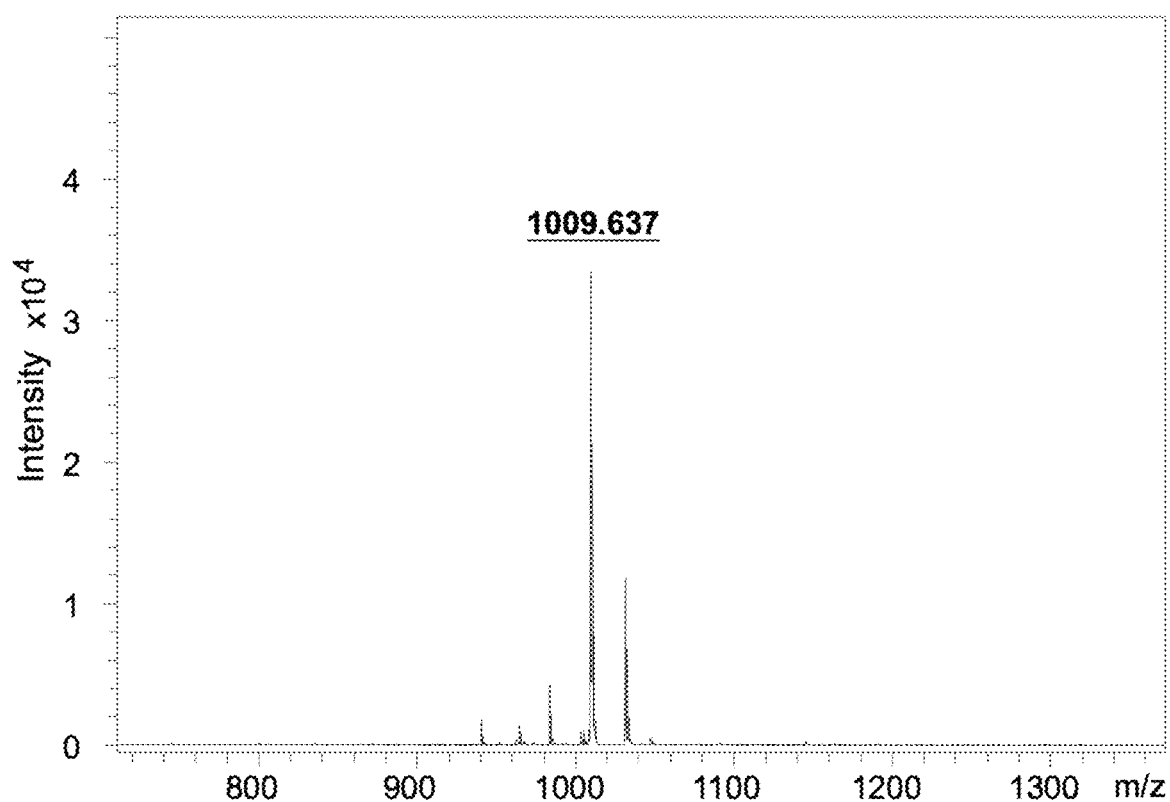

As illustrated below, the N-terminus of peptide 10 (KSKGK; SEQ ID NO: 7) was modified by an acetic acid, and the C-terminus thereof was modified by an amine-Xaa$_8$-azide. As a center core, peptide 10 has one acetyl group to block the amino group at N-terminus and one azido group at C-terminus for click reaction with an element or a linker unit. The peptide 10 comprises three K residues, with the spacer between the first and second K residues being S and the one between the second and third K residues being G. FIG. 11B shows that the peptide 10 had a molecular weight of 1009 daltons.

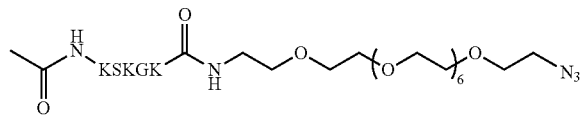

Example 4: Direct Synthesis of Dual Conjugating Groups-Containing Peptide 11 (SEQ ID NO: 8) as a Peptide Core for Constructing Multi-Arm Linker Unit As illustrated below, the peptide 11 has an amino acid sequence of GGSGGSKGSSGKGGSGGS (SEQ ID NO: 8), in which the N-terminus was modified by an Exo-5-norbornenecarboxylic acid, and the C-terminus is modified by a 3-azido-propylamine. The peptide 11 (illustrated below), serving as a center core for constructing a center linker unit, has an exo-5-norbornenyl group at the N-terminus for coupling one element or linker unit via click reaction, and an azido group at the C-terminus for another element or linker unit via click reaction. The dual conjugating groups-containing peptide 11 was custom-synthesized by ChinaPeptide Co., Ltd.

Example 5: Synthesis of Cholecystokinin Octapeptide (CCK8) Segment (SEQ ID NO: 9)

The CCK8-containing peptide had the sequence of CGGGGSDYMGWMDF (SEQ ID NO: 9) and was modified by an acetic acid at the N-terminus thereof and amidated by an amide resin at the C-terminus thereof. The CCK8-containing peptide was designed to be composed of an 8-amino acid residues of CCK with a consecutive N-terminal extension of six amino acid residues (CGGGGS; SEQ ID NO: 10) so that the N-terminus thereof is a cysteine residue. The N-terminal cysteine residue provided an SH group for conjugation with PEG-maleimide linking arms of the linker unit according to the present disclosure. This peptide was custom-synthesized by ChinaPeptide Co., Ltd.

Figure 12A:
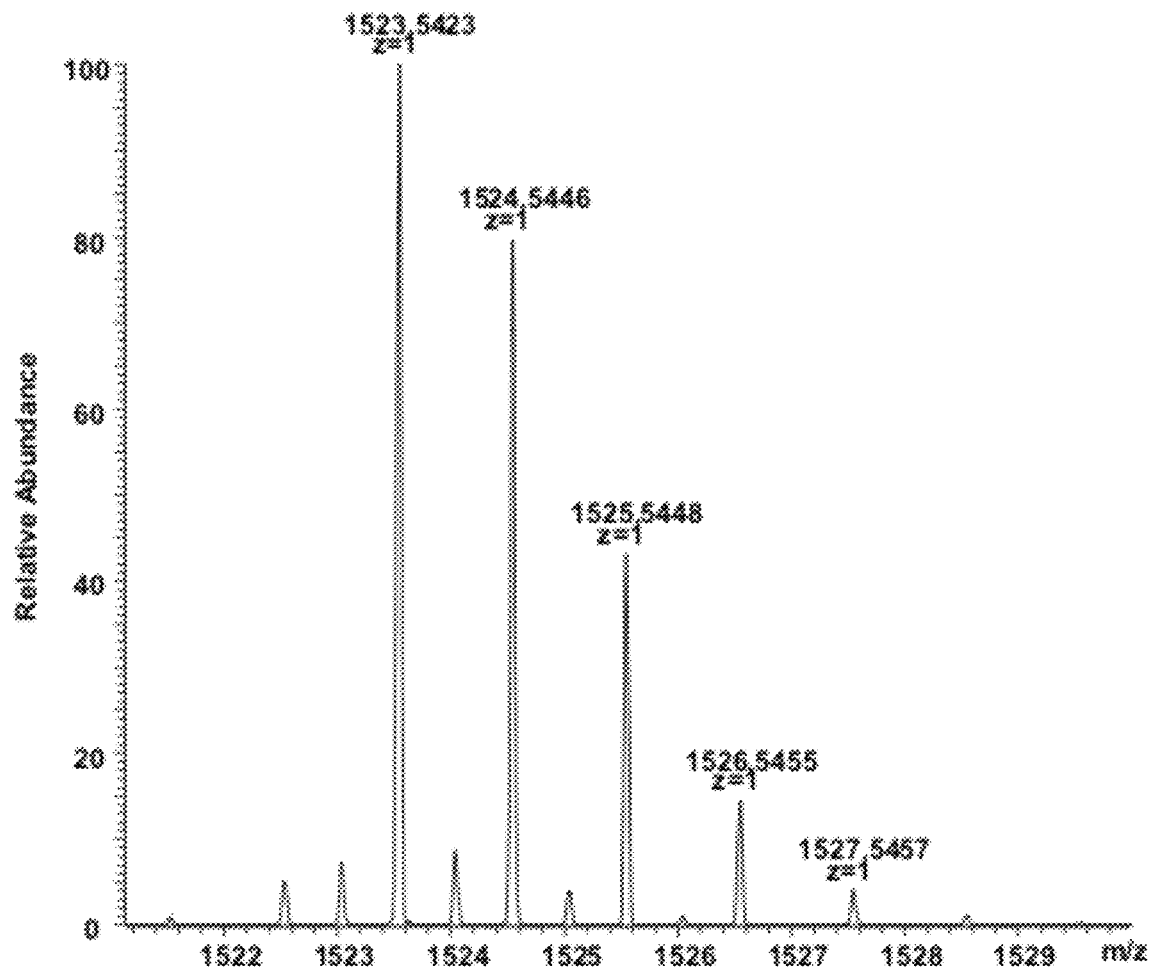
FIGS. 12A and 12B respectively show the results of mass spectrometry MALDI-TOF analysis of the CCK8-containing peptide and the CC8-containing linking arm according to Examples 5 and 6 of the present disclosure.

The thus-synthesized CCK8-containing peptide was examined using ESI-MS. The product was analyzed by mass spectroscopy ESI (FIG. 12A), and the data show (ESI-TOF) m/z: [M+H]$^+$—calculated for $C_{65}H_{86}N_{16}O_{21}S_3$ 1523.67; found 1523.5418. The four isotopic peaks were also visible in the MS spectrum at 1524.5448, 1525.5458 1526.5458, and 1527.5458, corresponding to [M+H+1]$^+$, [M+H+2]$^+$, [M+H+3]$^+$ and [M+H+4]$^+$, respectively.

Example 6: Conjugation of CCK8-Containing Peptide with a Mal-PEG$_6$-NHS

The thiol group of CCK8-containing peptide was reacted with a hetero-bifunctional crosslinker, Mal-PEG$_6$-NHS. The peptide was dissolved in 100% DMSO at a final concentration of 10 mM, while Mal-PEG$_6$-NHS, a hetero-bifunctional crosslinker, was dissolved in 100% DMSO at a 250-mM final concentration. Mal-PEG$_6$-NHS crosslinker was added to the dissolved peptide solution at 10-mM final concentration (1-fold molar excess over 10 mM peptide solution). The reaction mixture was incubated overnight at room temperature.

CCK8-PEG$_6$-NHS was purified by reversed-phase HPLC on a Supelco C18 column (250 mm×10 mm; 5 μm), using a mobile phase of acetonitrile and 0.1% trifluoroacetic acid, a linear gradient of 30% to 100% acetonitrile over 30 minutes, at a flow rate of 3.0 mL/min and a column temperature of 25° C. The elution profile of the reversed-phase HPLC of DM1-PEG$_6$-NHS was monitored by measuring the UV absorbance at 254 nm.

Figure 12B:
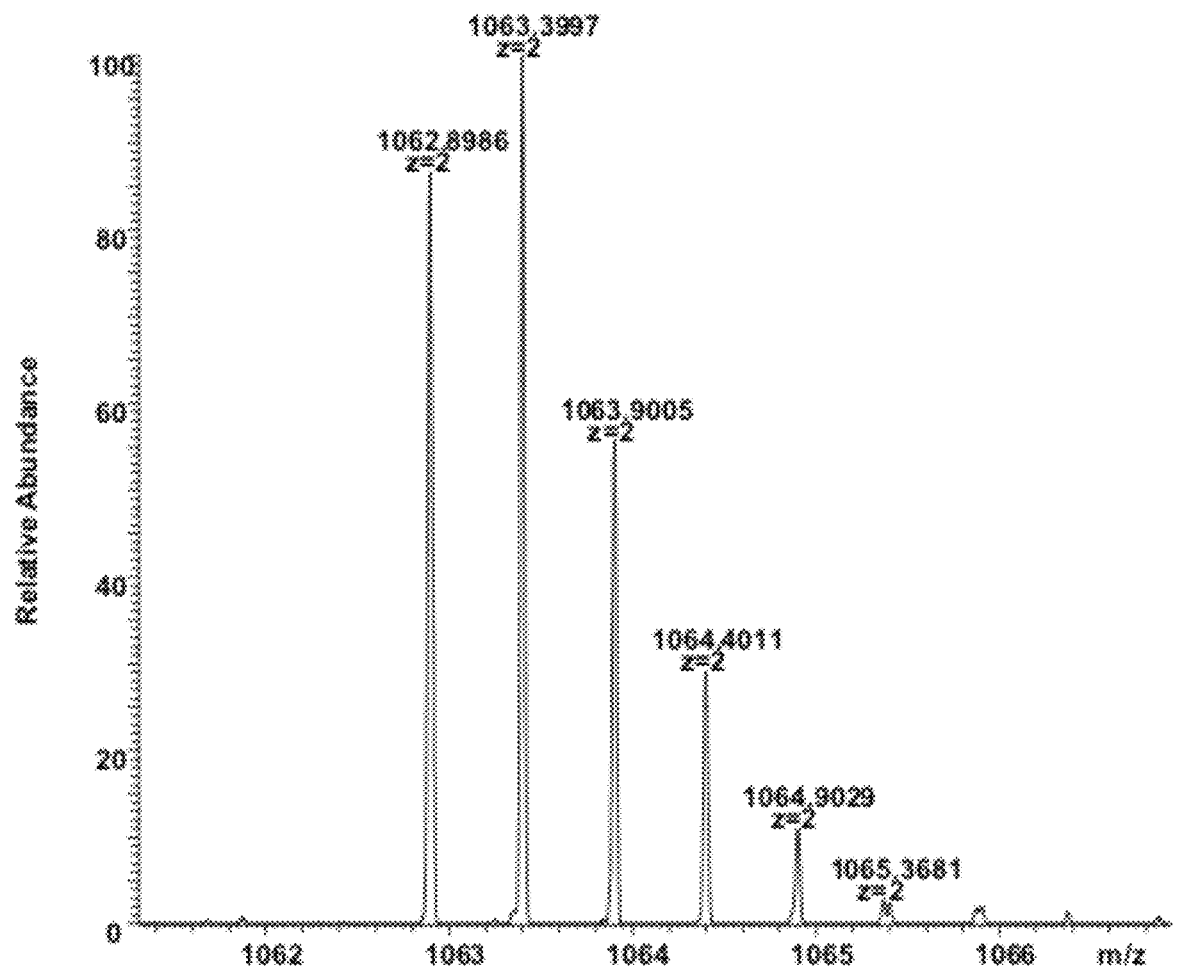

The thus-synthesized CCK8-PEG$_6$-NHS (illustrated below) was analyzed using mass spectroscopy ESI (FIG. 12B). The data show (ESI-TOF) m/z: [M+2H]$^{2+}$—calculated for $C_{91}H_{125}N_{19}O_{34}S_3$ 2125.28; found 2123.79. The six isotopic peaks were also visible in the MS spectrum at 1063.398, 1063.8978, 1064.4003, 1064.9022 and 1065.4061, corresponding to [M+2H+1]$^{2+}$, [M+2H+2]$^{2+}$, [M+2H+3]$^{2+}$, [M+2H+4]$^{2+}$ and [M+2H+5]$^{2+}$, respectively.

Example 7: Conjugation of Mertansine (DM1) with a Mal-PEG$_6$-CO$_2$H

DM1 was purchased from ALB Technology Inc., Hong Kong, China. The conjugation of DM1 with an SH group to the hetero-bifunctional crosslinker and the purification of the product were similar to those described in the preceding Example.

Briefly, the thiol group of DM1 molecule was reacted with a hetero-bifunctional crosslinker, Mal-PEG$_6$-CO$_2$H. DM1 was dissolved in 100% DMSO at a final concentration of 10 mM, while Mal-PEG$_6$-CO$_2$H was dissolved in 100% DMSO at a final concentration of 250 mM. Mal-PEG$_6$-CO$_2$H crosslinker was added to the dissolved DM1 solution at a final concentration of 10 mM (1-fold molar excess over 10 mM DM1 solution). The reaction mixture was incubated overnight at room temperature.

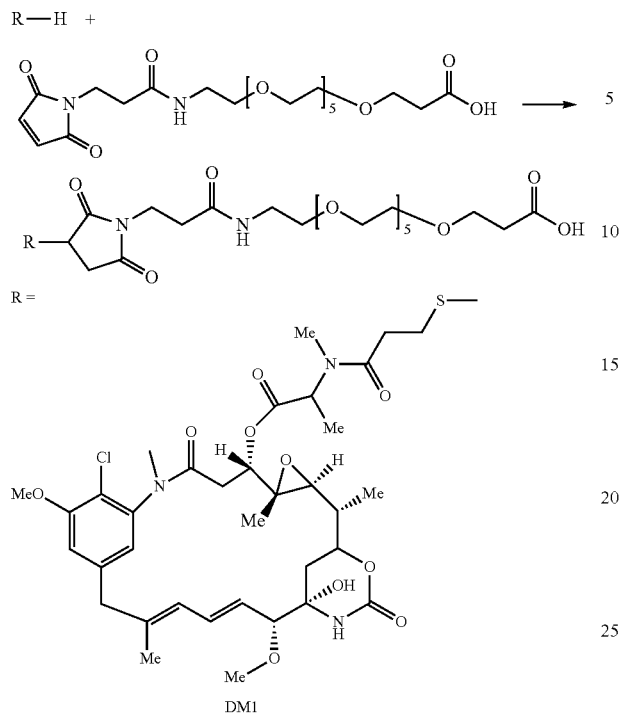

DM1-PEG$_6$-CO$_2$H was purified by reversed-phase HPLC on a Supelco C18 column (250 mm×10 mm; 5 μm), using a mobile phase of acetonitrile and 0.1% trifluoroacetic acid, a linear gradient of 30% to 100% acetonitrile over 30 minutes, at a flow rate of 3.0 mL/min and a column temperature of 25° C. The elution profile of the reversed-phase HPLC of DM1-PEG$_6$-CO$_2$H showed that the eluting peak of DM1-PEG$_6$-CO$_2$H has a retention time of 11.5 minutes, which was monitored by detecting the UV absorbance at 254 nm. The result of mass spectroscopic analysis of the thus-synthesized DM1-PEG$_6$-CO$_2$H (illustrated above) indicated that this molecular construct had a m.w. of 1242.429 daltons.

Example 8: Synthesis of DBCO-Containing Linker Unit with Peptide 7 as a Peptide Core and TFP-PEG$_{12}$-Mal or NHS-PEG$_6$-Mal as Linking Arms In this example, three linking arms of PEG$_{12}$-maleimide were conjugated to the peptide core DBCO-peptide 7. The crosslinker, TFP-PEG$_{12}$-maleimide [alpha-maleinimido-omega-(2.3.5.6-tetrafluorophenyl-propionamido)-dodeca-ethyleneglycol] ester, was purchased from QuantaBiodesign Inc (Plain City, USA). The conjugation process was performed per the manufacturer's instruction; the peptide with K residues was dissolved in 100% DMSO at a final concentration of 10 mM. TFP-PEG$_{12}$-maleimide crosslinker was added to the dissolved peptide at a final concentration of 60 mM (6-fold molar excess over 10 mM peptide solution). The catalyst, organic base DABCO (1,4-diazabicyclo [2.2.2]octane) (5 equiv), was added to the reaction mixtures. The reaction mixtures were incubated for over 18 hours at room temperature.

Figure 13A:
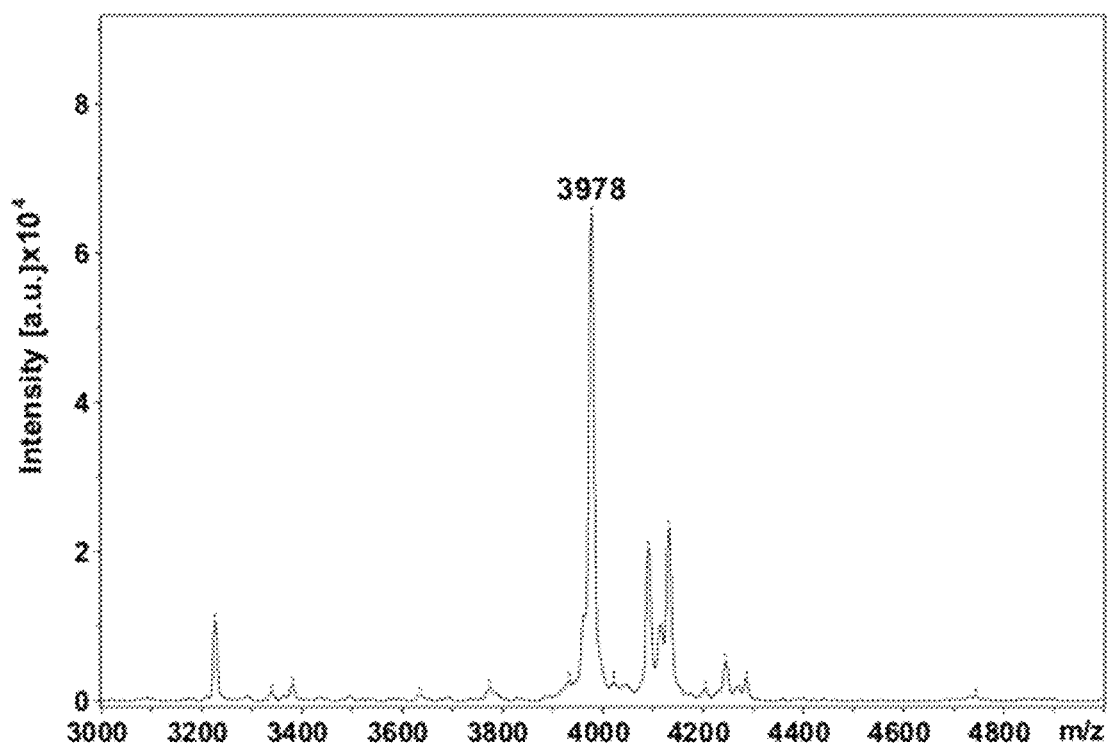
FIGS. 13A and 13B show the results of mass spectrometry MALDI-TOF analysis of the linker unit comprising specified core and linking arms according to Example 8 of the present disclosure.

As illustrated below, the thus-synthesized maleimide-PEG$_{12}$-conjugated DBCO-peptide 7 carried one coupling arm with a DBCO group and three PEG linking arms with maleimide groups; FIG. 13A shows the result of mass spectrometry MALDI-TOF, which indicated that the present molecular construct had a m.w. of 3978 daltons.

Three linking arms of PEG$_6$-maleimide were conjugated to the peptide core DBCO-peptide 7. The crosslinker, NHS-PEG$_6$-maleimide (succinimidyl-[(N-maleimido-propionamido)-hexaethyleneglycol]) ester, was purchased from Conju-probe Inc. The conjugation process was performed per the manufacturer's instruction; the peptide with K residues was dissolved in 100% DMSO at a final concentration of 10 mM. NHS-PEG$_6$-maleimide crosslinker was added to the dissolved peptide at a final concentration of 60 mM (6-fold molar excess over 10 mM peptide solution). The catalyst, organic base DABCO (5 equiv), was added to the reaction mixtures. The reaction mixtures were incubated for over 18 hours at room temperature.

Figure 13B:
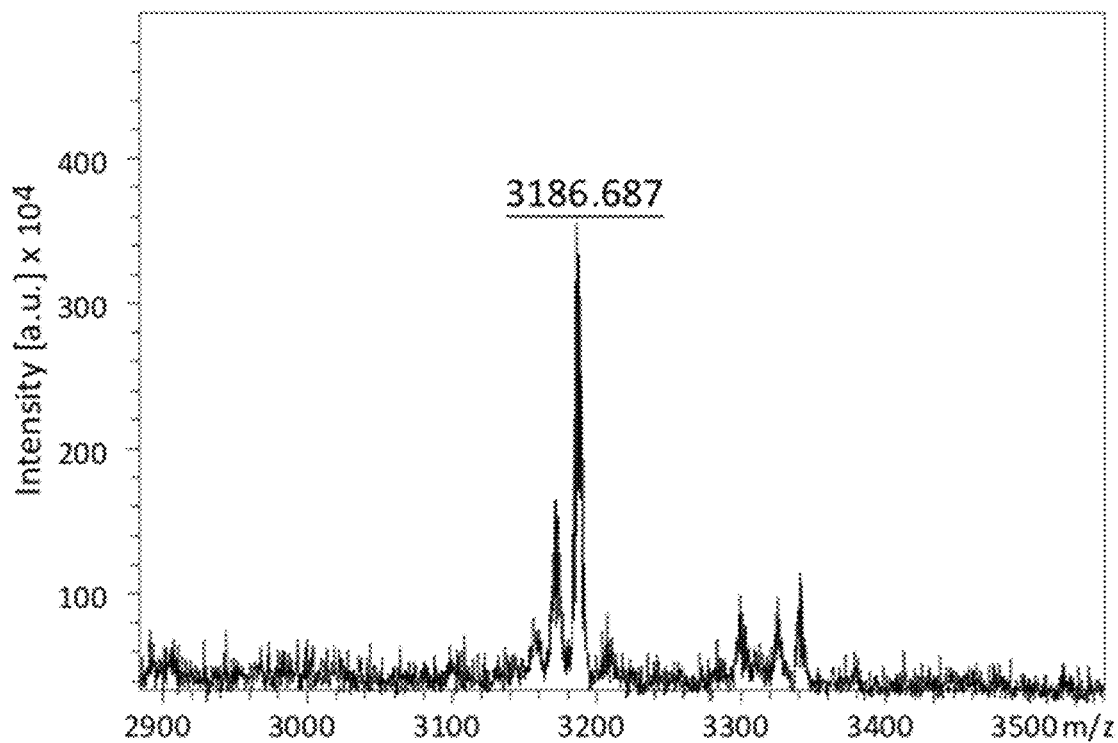

The thus-synthesized maleimide-PEG$_6$-conjugated azide-peptide 7 carried one coupling arm with a DBCO group and three PEG linking arms with maleimide groups. The result shows that it had a molecular weight of 3186.687 daltons (FIG. 13B).

Example 9: Synthesis of a Multi-Arm Linker Unit by Conjugating NHS-PEG$_6$-Mal to NH$_2$ Groups of Azide-Containing Peptide 8

The conjugation of the crosslinkers was performed using the protocol described in above examples. The thus-synthesized PEG$_6$-maleimide-conjugated azide-peptide 8 was examined using MALDI-TOF.

Figure 14:
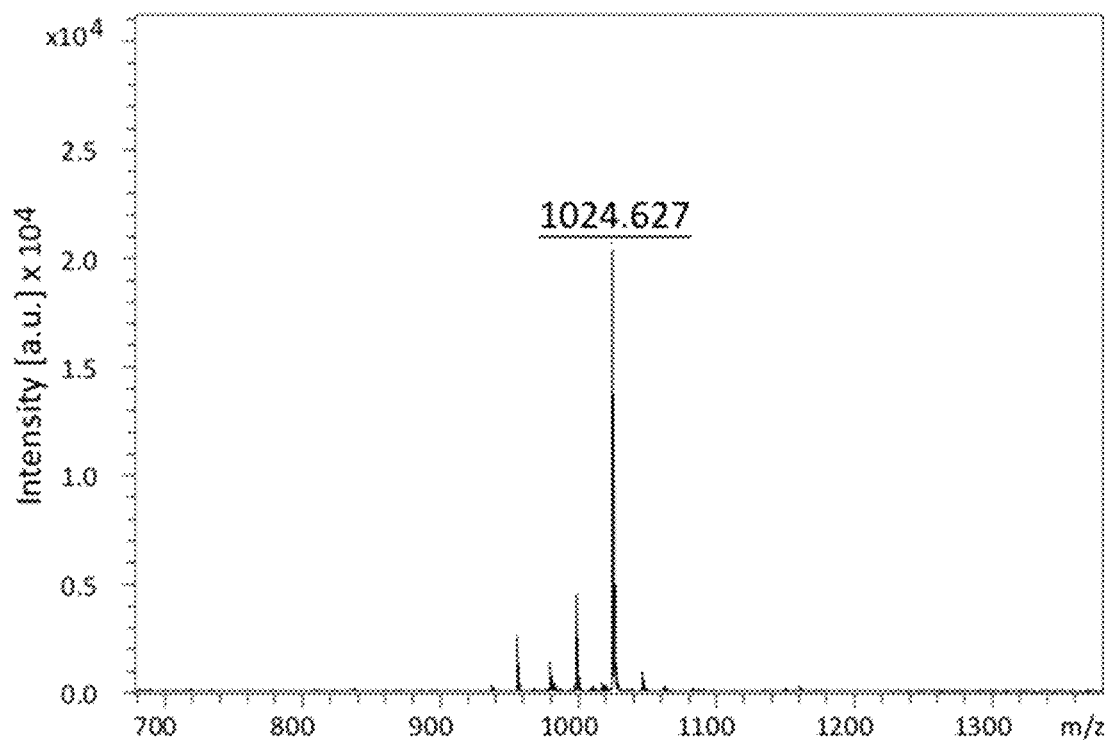
FIG. 14 shows the result of mass spectrometry MALDI-TOF analysis of the linker unit comprising the specified core and linking arms according to Example 9 of the present disclosure.

As illustrated below, the thus-synthesized maleimide-PEG$_6$-conjugated azide-peptide 8 carried one coupling arm with an azide group and three PEG linking arms with maleimide groups; FIG. 14 shows the result of mass spectrometry MALDI-TOF, which indicated that the present molecular construct had a m.w. of 1024.627 daltons.

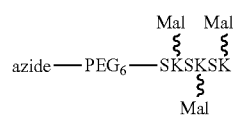

Example 10: Synthesis of a Multi-Arm Linker Unit by Conjugating NHS-PEG$_6$-Mal to NH$_2$ Groups of Alkyne-Containing Peptide 9

The conjugation of the crosslinkers was performed using the protocol described in above examples. The thus-synthesized PEG$_6$-maleimide-conjugated alkyne-peptide 9 was examined using MALDI-TOF.

Figure 15:
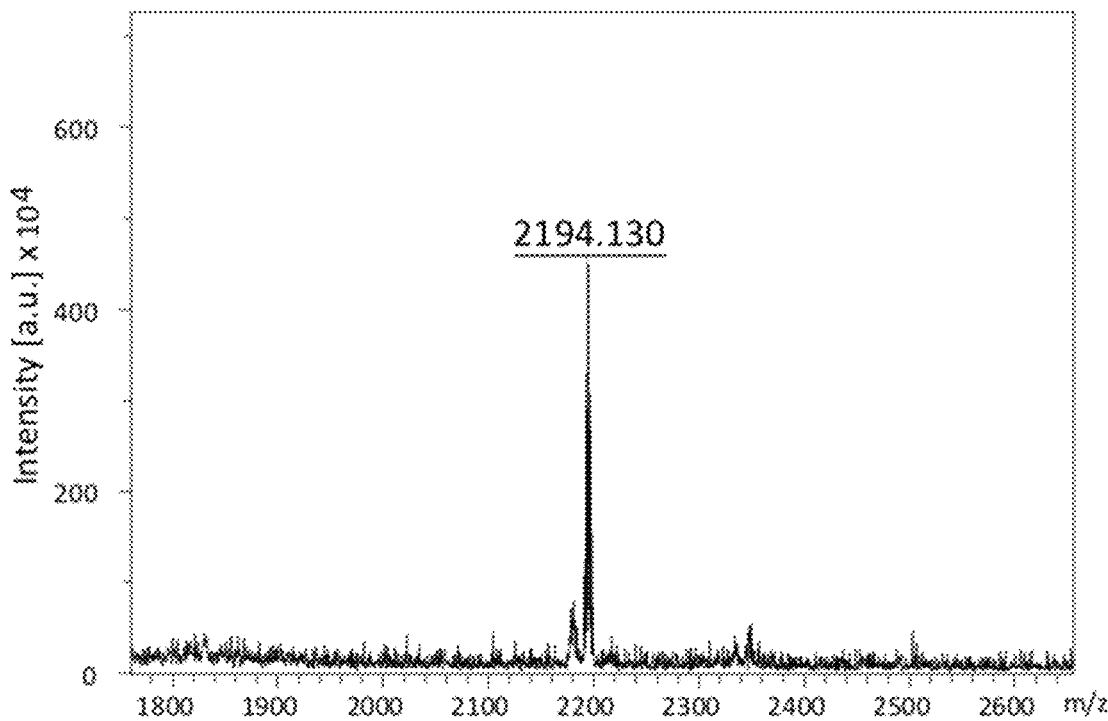
FIG. 15 shows the result of mass spectrometry MALDI-TOF analysis of the linker unit comprising the specified core and linking arms according to Example 10 of the present disclosure.

As illustrated below, the thus-synthesized maleimide-PEG$_6$-conjugated alkyne-peptide 9 carried one coupling arm with an alkyne group and three PEG linking arms with maleimide groups; FIG. 15 shows the result of mass spectrometry MALDI-TOF, which indicated that the present molecular construct had a m.w. of 2194.13 daltons.

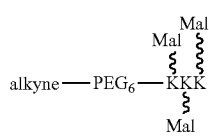

Example 11: Direct Synthesis of Norbornene-Containing Linker Unit with Peptide 12 (SEQ ID NO: 11) as a Peptide Core and RSGSSG (SEQ ID NO: 12) as Linking Arms The norbornene-containing linker unit with peptide 12 as a peptide core and the peptide RSGSSG (SEQ ID NO: 12) as linking arms was synthesized directly using standard Fmoc chemistry by manual synthesis. As illustrated below, the N-terminus of the linking arm was modified by a phenylmaleimide group. The inventors designed the linker unit and outsourced the production of the norbornene-containing linker unit with the phenylmaleimide-modified linking ams to ONTORES Co., Ltd. (Hangzhou, China).

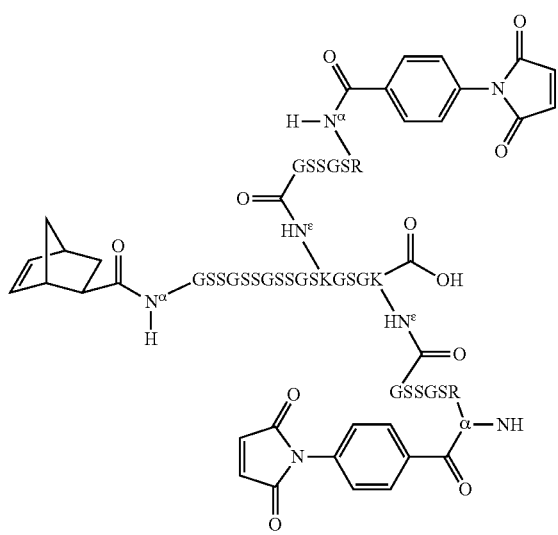

Figure 16:
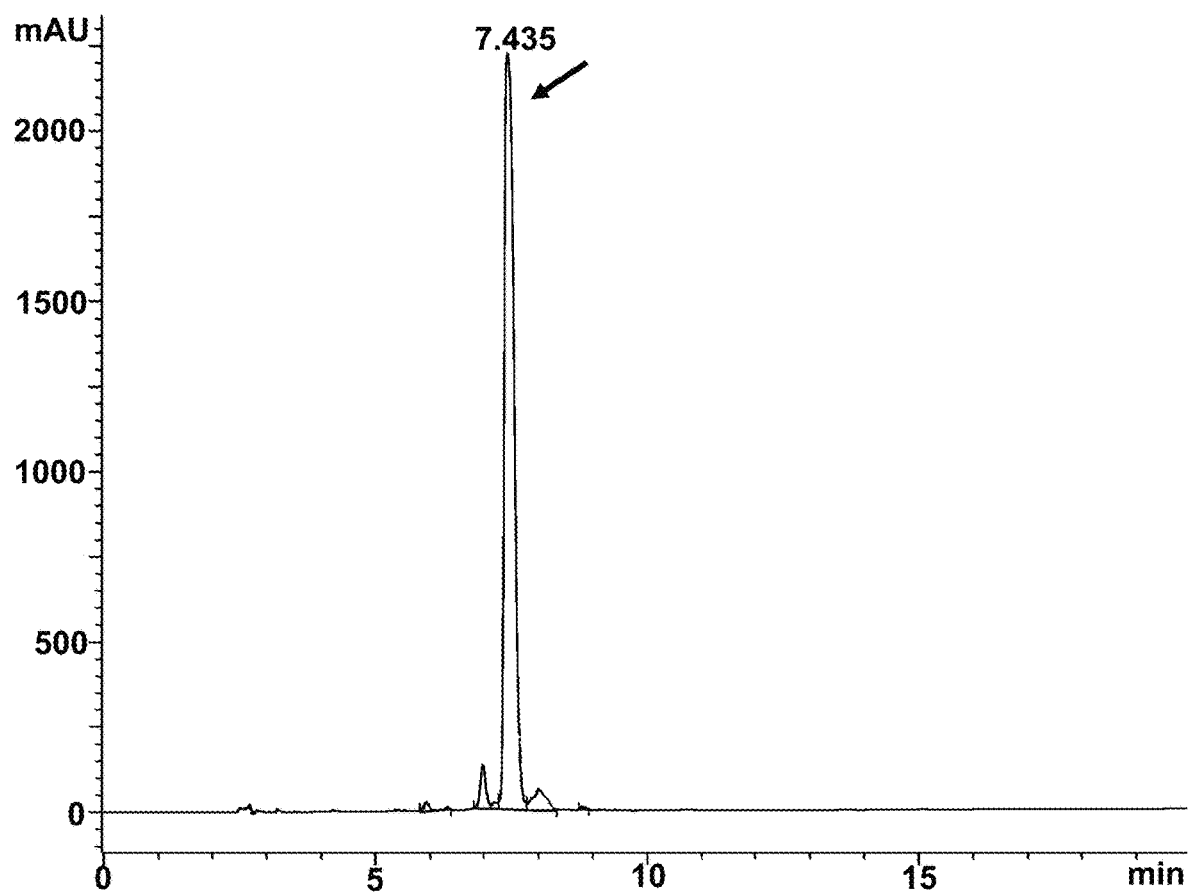
FIG. 16 shows the result of reversed-phase HPLC analysis of the norbornene-containing linker unit with the phenylmaleimide-modified linking arms according to Example 11 of the present disclosure.

The purified sample of the norbornene-containing linker unit with the phenylmaleimide-modified linking arms was analyzed by reversed-phase analytical HPLC on a C18 column (250 mm×4.6 mm; 5 μm), using a mobile phase of acetonitrile and 0.1% trifluoroacetic acid, a linear gradient of 27% to 47% acetonitrile over 20 minutes, at a flow rate of 1.0 ml/min and a column temperature of 30° C. FIG. 16 shows the reversed-phase HPLC profile of the norbornene-containing linker unit with the phenylmaleimide-modified linking arms, with the peak being indicated with arrow.

The identification of the norbornene-containing linker unit with the phenylmaleimide-modified linking arms was carried out by mass spectrometry ESI-MS.

The present norbornene-containing linker unit with the phenylmaleimide-modified linking arms was a peptide core-based linker unit carrying one coupling arm with an norbornene group and three linking arms respectively having the phenylmaleimide modification at the free-terminus thereof. The result of mass spectrometry of the thus-synthesized linker unit showed a strong molecular ion at 966, corresponding to $[M+3H]^{3+}$, indicating that the actual molecular weight of the linker unit was 2895 daltons.

Example 12: Direct Synthesis of Alkyne-Containing Linker Unit with Peptide 13 (SEQ ID NO: 1) as a Peptide Core and RSGSSG (SEQ ID NO: 12) as Linking Arms The alkyne-containing linker unit with peptide 13 as a peptide core and RSGSSG (SEQ ID NO: 12) as linking arms was synthesized directly using standard Fmoc chemistry by manual synthesis. As illustrated below, the N- and C-termini of the peptide 13 are respectively amidated by 4-pentynoic acid and esterified by methyl alcohol; the N-terminus of the linking arm was modified by a 3-maleimidopropionic acid. The inventors designed the linker unit and outsourced the production of the alkyne-containing linker unit with the maleimide-modified linking arms to Shanghai ChinaPeptide Co., Ltd. (Shanghai, China).

Figure 17:
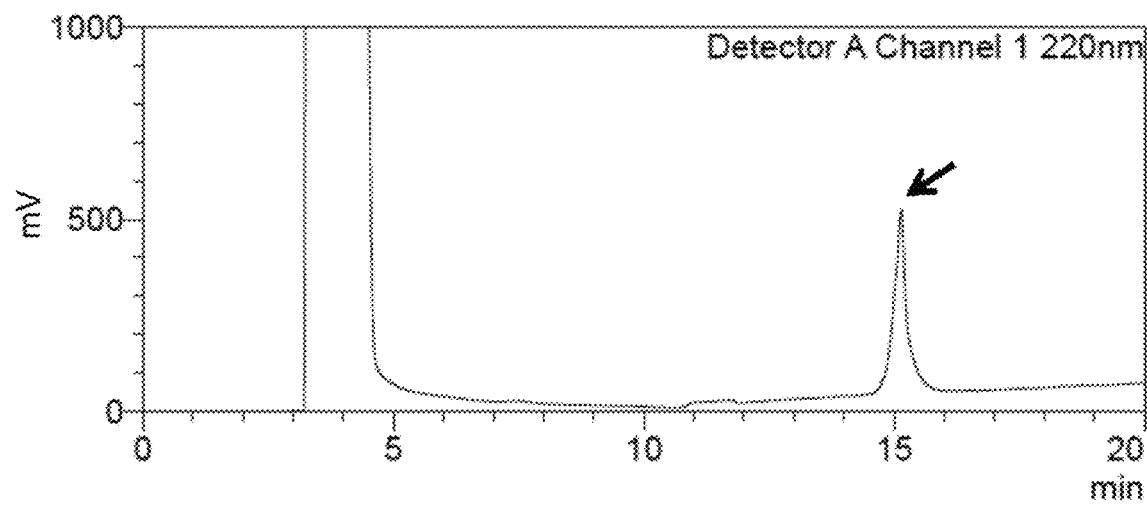
FIG. 17 shows the result of reversed-phase HPLC analysis of the alkyne-containing linker unit with the maleimide-modified linking arms according to Example 12 of the present disclosure.

The purified sample of the alkyne-containing linker unit with the maleimide-modified linking arms was analyzed by reversed-phase analytical HPLC on a kromasil 100-5 C18 column (250 mm×4.6 mm; 5 μm), using a mobile phase of acetonitrile and 0.1% trifluoroacetic acid, a linear gradient of 5% to 48% acetonitrile over 15 minutes, at a flow rate of 1.0 ml/min and a column temperature of 35° C. FIG. 17 is the reversed-phase HPLC profile of the alkyne-containing linker unit with the maleimide-modified linking arms, in which the peak is indicated with an arrow head.

The identification of the alkyne-containing linker unit with the maleimide-modified linking arms was carried out by mass spectrometry MALDI-TOF.

Figure 18:
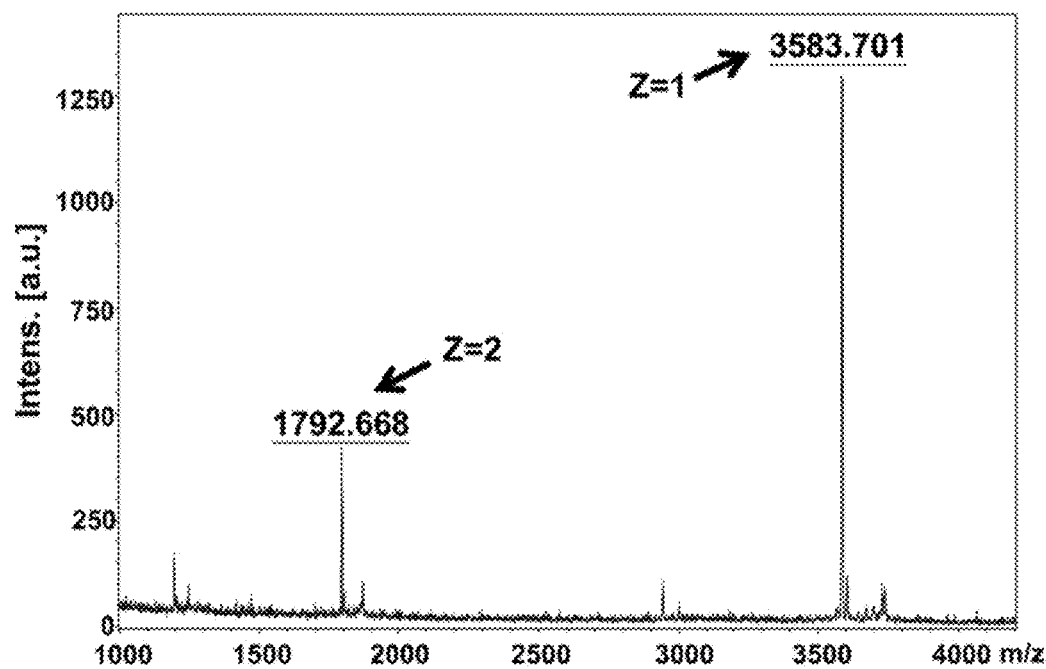
FIG. 18 shows the result of mass spectrometry MALDI-TOF analysis of the linker unit according to Example 12 of the present disclosure.

The present alkyne-containing linker unit with the maleimide-modified linking arms was a peptide core-based linker unit carrying one coupling arm with an alkyne group and three linking arms respectively having the maleimide modification at the free terminus thereof. FIG. 18 shows the result of mass spectrometry MALDI-TOF, which indicated that the present molecular construct had a m.w. of 3583.701 daltons.

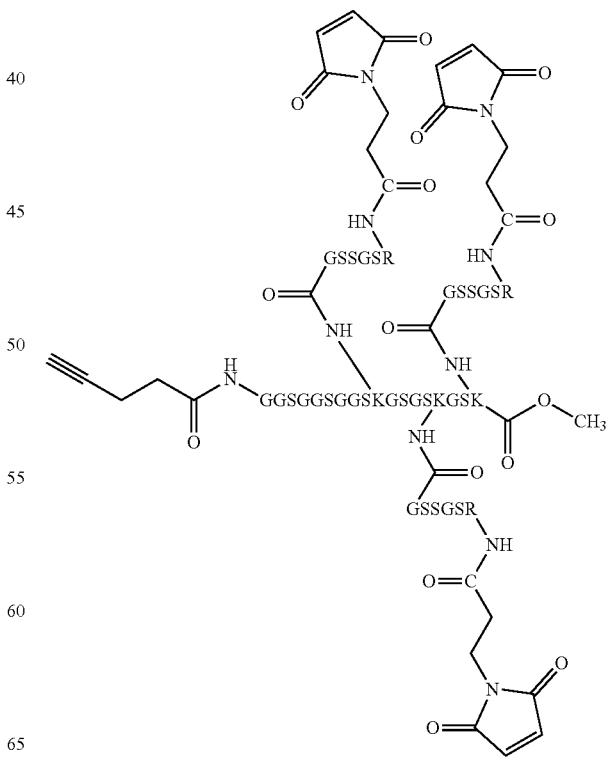

Example 13: Direct Synthesis of Methyltetrazine-Containing Linker Unit with Peptide 14 (SEQ ID NO: 13) as a Peptide Core and SGSSGSSG (SEQ ID NO: 14) as Linking Arms The methyltetrazine-containing linker unit with peptide 14 as a peptide core and SGSSGSSG (SEQ ID NO: 14) as linking arms was synthesized directly using standard Fmoc chemistry by manual synthesis. As illustrated below, the N-terminus of the linking arm was modified by a 3-maleimidopropionic acid. The inventors designed the linker unit and outsourced the production of the methyltetrazine-containing linker unit with the maleimide-modified linking arms to Shanghai WuXi AppTech Co., Ltd.

The purified sample of the methyltetrazine-containing linker unit with the maleimide-modified linking arms was analyzed by reversed-phase analytical HPLC on a Gemini-NX 5u C18 column (150 mm×4.6 mm; 4 µm), using a mobile phase of acetonitrile and 0.1% trifluoroacetic acid, a linear gradient of 10% to 40% acetonitrile over 20 minutes, at a flow rate of 1.0 ml/min and a column temperature of 30° C.

reaction mixtures. The reaction mixtures were incubated for over 18 hours at room temperature. The CCK8-PEG$_6$-conjugated DBCO-peptide 7 was purified by reversed-phase HPLC on a Princeton SPHER-300 C18 column (250 mm×30 mm; 300 Å; 5 µm), using a mobile phase of acetonitrile and 0.1% trifluoroacetic acid, a linear gradient of 0% to 73% acetonitrile over 28 minutes, at a flow rate of 27.0 ml/min and a column temperature of 25° C.

Figure 19:
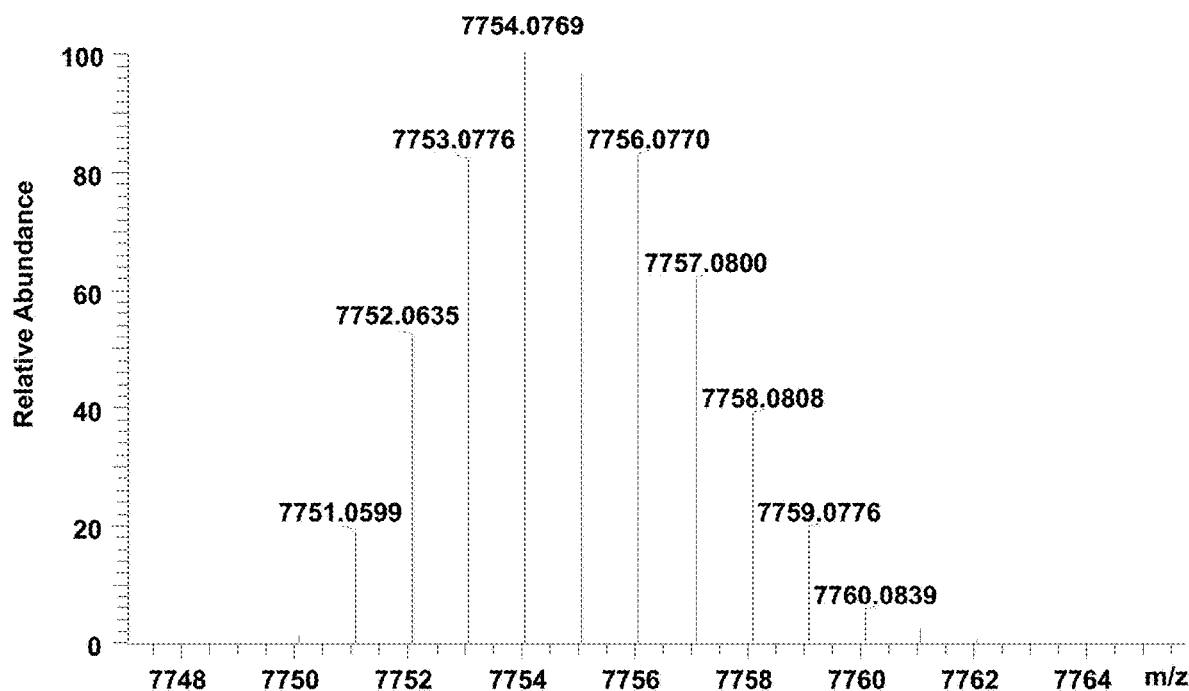
FIG. 19 shows the result of reversed-phase HPLC analysis of the linker unit comprising five cytotoxic drugs according to Example 14 of the present disclosure.

As illustrated below, the thus-synthesized CCK8-PEG$_6$-conjugated DBCO-peptide 7 carried one coupling arm with a DBCO group and three PEG linking arms with CCK8 peptide. The data show (ESI-TOF) m/z: [M+H]$^+$—calculated for $C_{334}H_{470}N_{77}O_{119}S_9$ 7751.0574; found 7751.0533. The nine isotopic peaks were also visible in the MS spectrum at 7752.0714, 7753.0759, 7754.0818, 7755.0820, 7756.0849, 7757.0353, 7758.0647, 7759.0844 and 7760.0636, corresponding to [M+H+1]$^+$, [M+H+2]$^+$, [M+H+3]$^+$, [M+H+4]$^+$, [M+H+5]$^+$, [M+H+6]$^+$, [M+H+7]$^+$, [M+H+8]$^+$ and [M+H+9]$^+$ (FIG. 19).

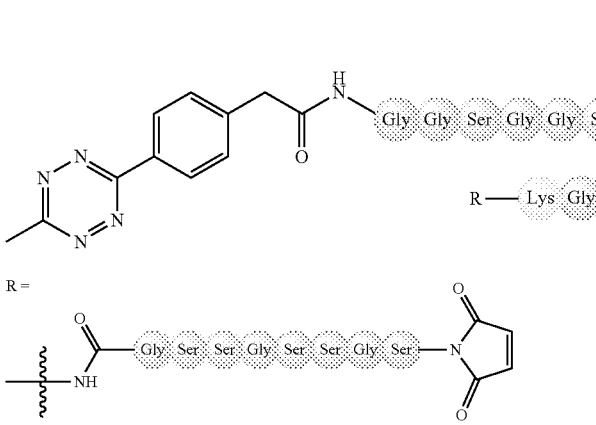

The identification of the methyltetrazine-containing linker unit with the maleimide-modified linking arms was carried out by mass spectrometry MALDI-TOF.

The present methyltetrazine-containing linker unit with the maleimide-modified linking arms was a peptide core-based linker unit carrying one coupling arm with a methyltetrazine group and three linking arms respectively having the maleimide modification at the free-terminus thereof. The result of mass spectrometry MALDI-TOF indicated that the present molecular construct had a m.w. of 1038 daltons.

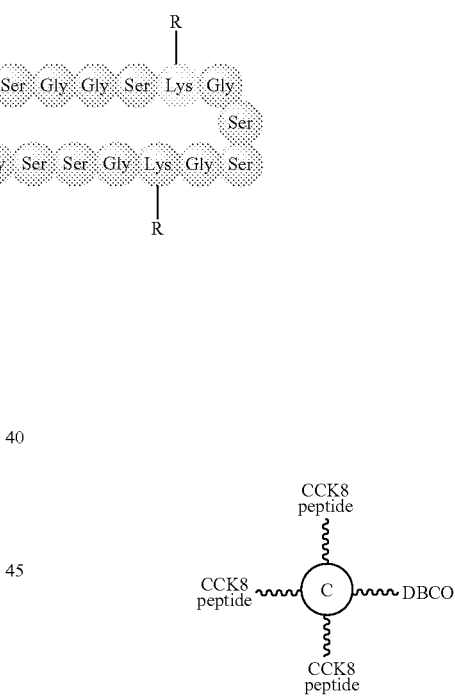

Example 14: Conjugating NHS-PEG$_6$-CCK8 to NH$_2$ Groups of DBCO-Containing Peptide 7

This example showed that three PEG$_6$-CCK8 were conjugated to the peptide core DBCO-containing peptide 7. The NHS-PEG$_6$-CCK8 was prepared in an earlier Example.

The conjugation process was performed per the manufacturer's instruction; the peptide with K residues was dissolved in 100% DMSO at a final concentration of 1 mM. The NHS-PEG$_6$-CCK8 prepared in the preceding example was added to the dissolved peptide at a final concentration of 6 mM (6-fold molar excess over 1 mM peptide solution). The catalyst, organic base DABCO (50 equiv) was added to the

Example 15: Conjugating CO$_2$H-PEG$_6$-DM1 to NH$_2$ Groups of Azide-Containing Peptide 2

The synthesized azide-containing peptide 2 (Chinapeptide Inc., Shanghai, China) was dissolved in dissolved in 100% DMSO at a final concentration of 10 mM. The CO$_2$H-PEG$_6$-DM1 was prepared in an earlier Example.

Azide-containing peptide 2 and organic base DMAP were mixed at 1/15 molar ratio in 100% CH$_2$Cl$_2$. Prior to conjugation of CO$_2$H-PEG$_6$-DM1 to azide-containing peptide 2, ethyl(dimethylaminopropyl)carbodiimide (EDC) was added to CO$_2$H-PEG$_6$-DM1 solution at a molar ratio of 1/2 (CO$_2$H-PEG$_6$-DM1:EDC) in 100% CH$_2$Cl$_2$ and then incubated for activating CO$_2$H group of CO$_2$H-PEG$_6$-DM1 molecule. Subsequently, EDC-activated CO$_2$H-PEG$_6$-DM1 was added to the azide-containing peptide 2 solution at a final molar ratio of 1/6 (azide-containing peptide 2: CO$_2$H-PEG$_6$-DM1) in 100% CH$_2$Cl$_2$. The reaction mixture was further incubated for overnight at room temperature.

The azide-containing peptide 2 was purified by reversed-phase HPLC on a Supelco C18 column (250 mm×10 mm; 5 µm), using a mobile phase of acetonitrile and 0.1% trifluoroacetic acid, a linear gradient of 0% to 100% acetonitrile over 30 minutes, at a flow rate of 3.0 ml/min and a column temperature of 25° C.

Figure 20A:
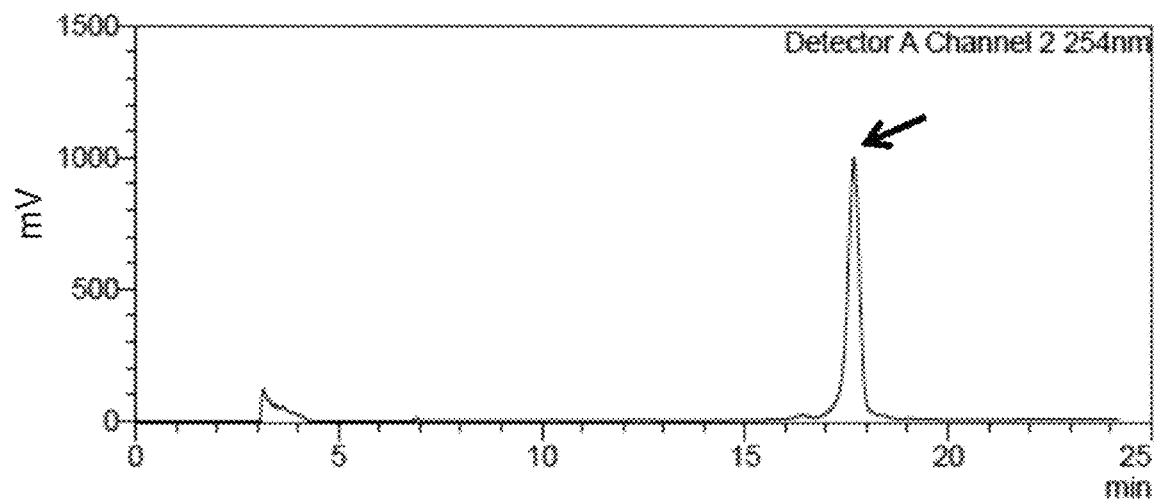
FIGS. 20A and 20B respectively show the result of reversed-phase HPLC and mass spectrometry MALDI-TOF analysis of the linker unit comprising five cytotoxic drugs according to Example 15 of the present disclosure.
Figure 20B:
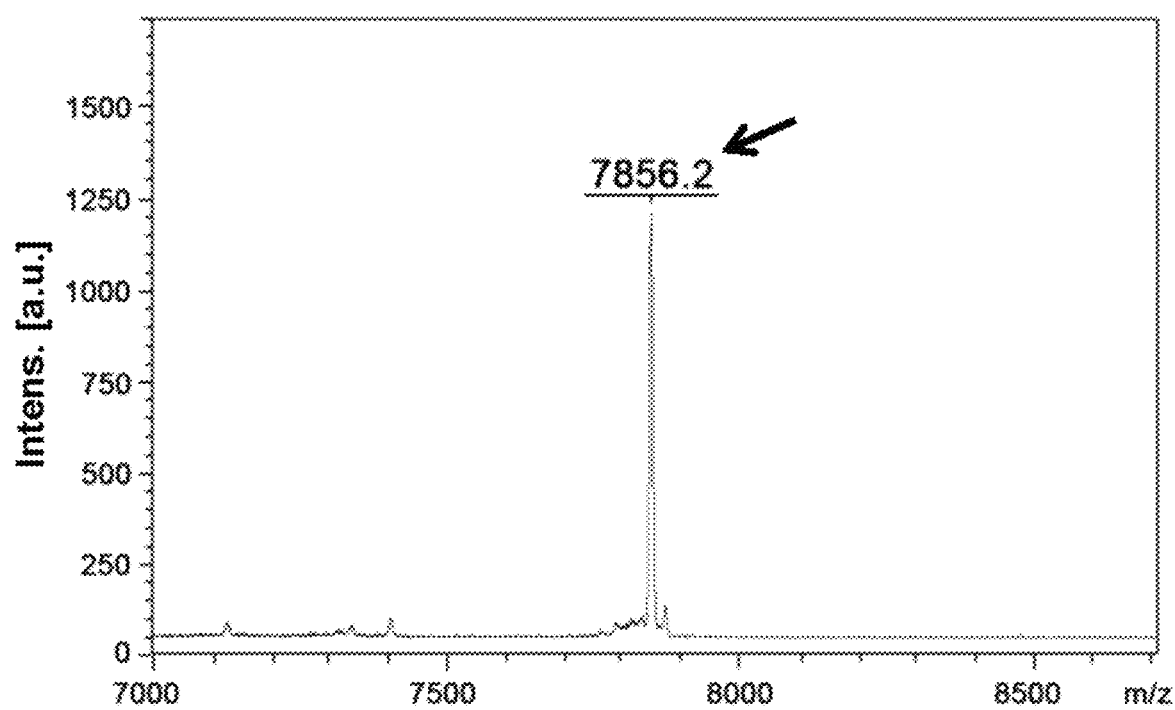

FIG. 20A shows the reversed-phase HPLC elution profile of azide-containing peptide 2 conjugated with five DM1 molecules, which had a peak with a retention time of 17.8 minutes. FIG. 20B shows the mass spectroscopic analysis of the thus-synthesized azide-containing peptide 2 conjugated with five DM1 molecules (illustrated below), which indicated that this molecular construct had a m.w. of 7856.2 daltons.

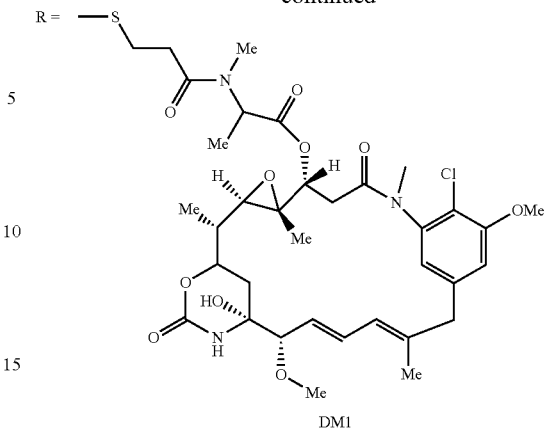

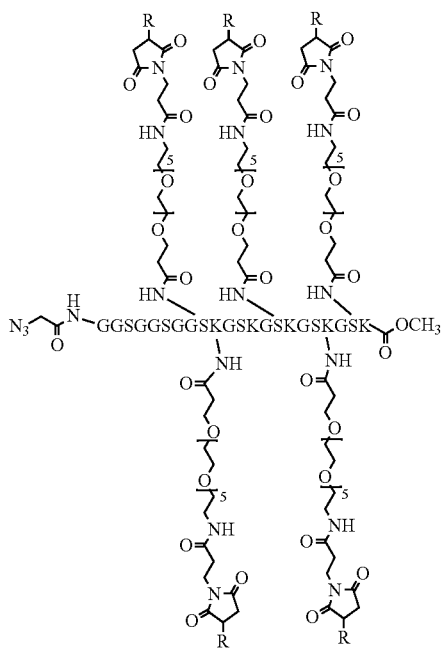

Example 16: Direct Synthesis of CCK8-Containing Targeting Bundle with Azide-Containing Peptide 15 (SEQ ID NO: 15) as a Peptide Core and EGGGGSDYMGWMDF (SEQ ID NO: 16) as Targeting Element-Linked Arms with CCK8 Peptides In this example, the CCK8-containing targeting bundle was synthesized. The drug bundle (as illustrated below) contained the azide-containing peptide 15 (as a peptide core) and a four branched arms having the sequence of EGGGGSDYMGWMDF (SEQ ID NO: 16). Said branched arm consists of a linking arm sequence (EGGGGS; SEQ ID NO: 17) and a CCK octapeptide (DYMGWMDF; SEQ ID NO: 18), with a primary amide modification at the free-terminus thereof. The CCK8-containing targeting bundle was synthesized using standard Fmoc chemistry by manual synthesis. The inventors designed the CCK8-targeting bundle and outsourced the production of the packed linker unit to Shanghai ChinaPeptide Co., Ltd. (Shanghai, China).

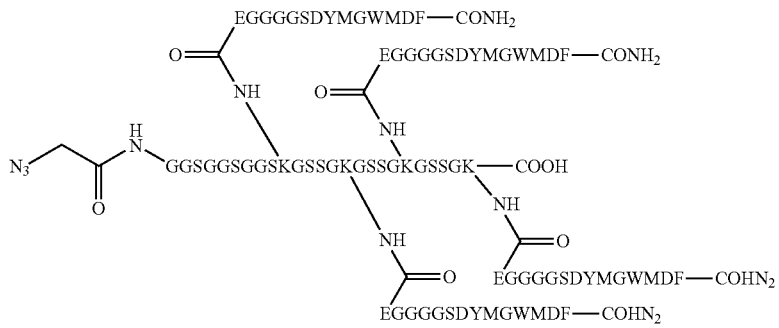

Figure 21:
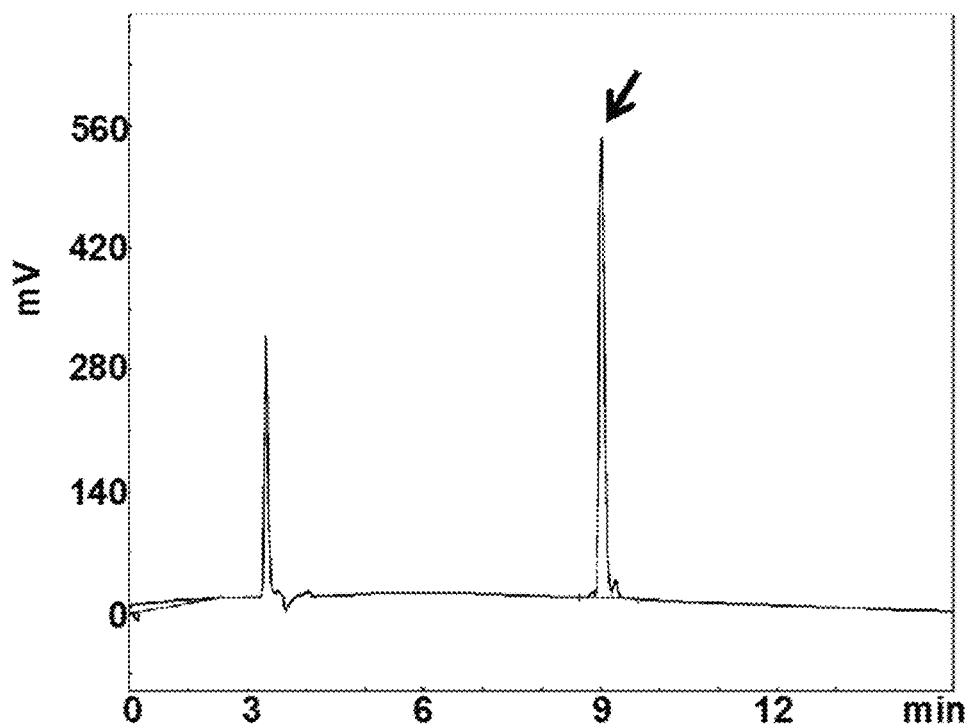
FIG. 21 shows the result of reversed-phase HPLC of the linker unit comprising CCK8 as the targeting element according to Example 16 of the present disclosure.

The purified sample of this CCK8-containing targeting bundle was analyzed by reversed-phase analytical HPLC on a kromasil 100-5 C18 column (250 mm×4.6 mm; 5 μm), using a mobile phase of acetonitrile and 0.1% trifluoroacetic acid, a linear gradient of 35% to 84% acetonitrile over 15 minutes, at a flow rate of 1.0 ml/min and a column temperature of 35° C. The reversed-phase HPLC profile in FIG. 21 showed that the eluting peak of the CCK8-targeting bundle has a retention time of 8.988 minutes; UV absorbance measurements were taken at 254 nm. The CCK8-containing targeting bundle had a purity of 95.25%.

Figure 22:
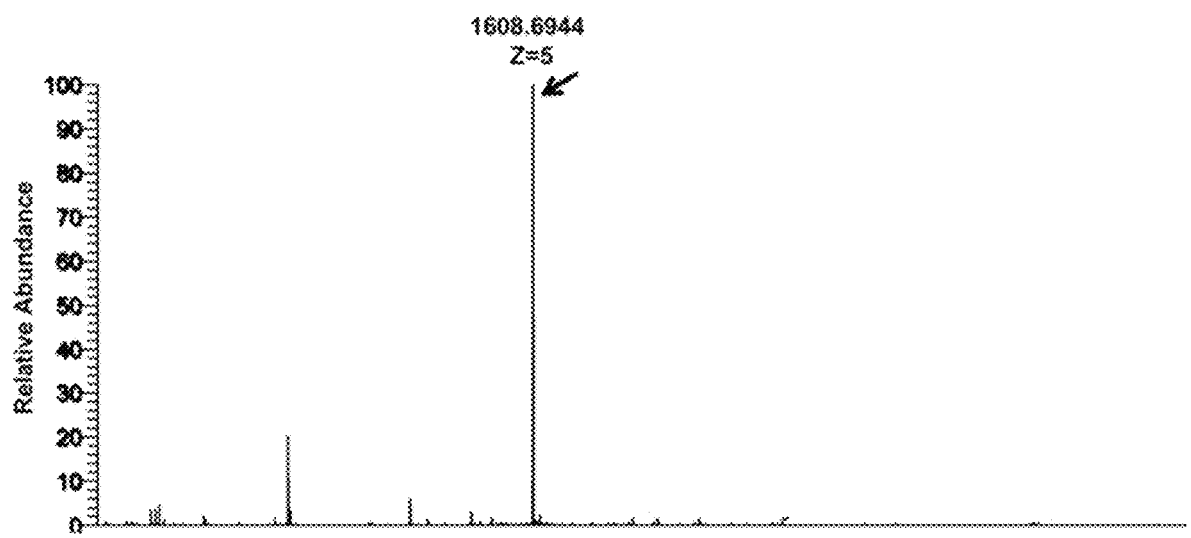
FIG. 22 shows the result of mass spectrometry ESI-TOF analysis of the linker unit comprising CCK8 as the targeting element according to Example 16 of the present disclosure.

The identification of this CCK8-containing targeting bundle was carried out by mass spectrometry ESI-TOF. FIG. 22 shows the result of mass spectrometry ESI-TOF, which indicated that the present molecular construct had a m.w. of 1608.6944 daltons (ESI-TOF) m/z (z=5): $[M+5H]^{5+}$.

Example 17: Production of the scFv Specific for Human CD3 by Expi293F Overexpression System To produce the scFv of a mutated teplizumab, we used the $V_H$ and $V_L$ DNA sequences of the humanized antibodies without further codon optimization. DNA sequences encoding $V_H$-GSTSGSGKPGSGEGSTKG (SEQ ID NO: 19)-$V_L$-(GGGGS)$_2$ (SEQ ID NO: 20)-C were synthesized. The mutated teplizumab antibody molecule contains a cysteine residue in CDR3 of $V_H$, which, as explained above, interferes with SH-maleimide conjugation. We therefore prepared a mutated teplizumab by substituting the cysteine residue with a serine residue. The amino acid sequences of the scFv specific for human CD3 prepared for the experiments of the invention are set forth in SEQ ID NO: 21.

For preparing recombinant proteins using a mammalian expression system, we used the overexpression system based on Expi293F™ cell line. The system employed ExpiFectamine™ 293 transfection kit (Life Technologies, Carlsbad, USA) consisting of the Expi293F™ cell line, the cationic lipid-based ExpiFectamine™ 293 Reagent and ExpiFectamine™ 293 transfection Enhancers 1 and 2, and the medium, which was part of the expression system (Gibco, N.Y., USA).

The gene-encoding sequences were placed in the pcDNA3 expression cassette. Expi293F cells were seeded at a density of 2.0×10$^6$ viable cells/ml in Expi293F expression medium and maintained for 18 to 24 hours prior to transfection to ensure that the cells were actively dividing at the time of transfection. At the time of transfection, 7.5×10$^8$ cells in 255-ml medium in a 2-liter Erlenmeyer shaker flask were transfected by ExpiFectamine™ 293 transfection reagent. The transfected cells were incubated at 37° C. for 16 to 18 hours post-transfection in an orbital shaker (125 rpm) and the cells were added ExpiFectamine™ 293 transfection enhancer 1 and enhancer 2 to the shaker flask, and incubated for 5 to 6 days. Culture supernatants were harvested and the expressed scFv recombinant proteins in the media were purified using Protein L affinity chromatography.

Figure 23A:
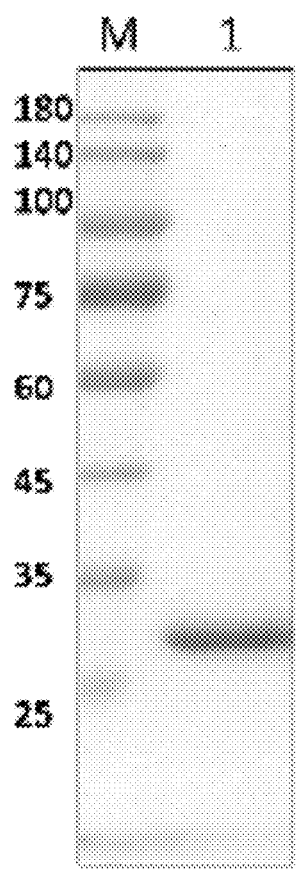
FIG. 23A to FIG. 23C respectively show the purity of specific scFv and its binding affinity to T cells according to Examples 17-19 of the present disclosure.

MALDI-TOF mass spectrometric analysis showed that the scFv had a m. w. of 27643 daltons. The purity of the mutated teplizumab scFvs specific for CD3 was identified through Coomassie staining of 12% SDS-PAGE. FIG. 23A shows SDS-PAGE analyses of purified scFv of the mutated teplizumab.

Example 18: Staining Analysis to Examine the Binding of the Mutated Teplizumab scFv to Human CD3 on the Jurkat T Cell Line The ability of the mutated teplizumab to bind to human T lymphocytes, which express CD3 was studied with Jurkat T cell line. The mutated teplizumab was analyzed for their ability to bind to human CD3 molecules on Jurkat T cell line. Jurkat cells are immortalized line of human T lymphocyte cell which express the T cell receptor (TcR)/CD3 complexes on the cell surface.

Figure 23B:
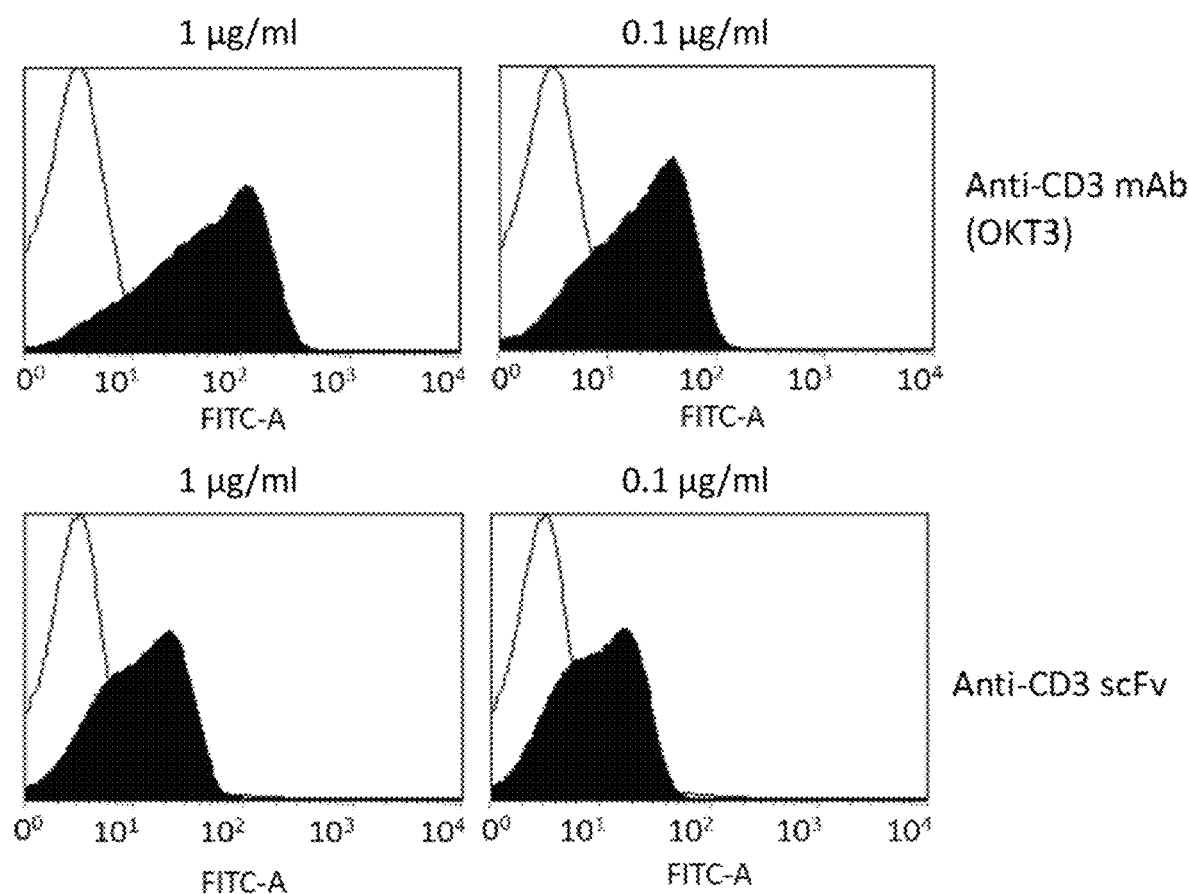

The assay was performed by incubating 2×10$^6$ Jurkat T cells with 0.1 and 1 μg/ml of the scFv in PBS with 1 FBS and 0.1% sodium azide on ice for 30 minutes. Cells were washed and incubated with FITC-conjugated Protein L (ACROBiosystems Inc., Newark, USA), diluted 1:200 in PBS/FBS, at 4° C. for 30 minutes in the dark. Protein L-FITC and FITC-conjugated rabbit anti-mouse IgG.Fc (AbD Serotec) were used as secondary antibodies. The staining of secondary antibodies alone were as negative controls. OKT3, a mouse monoclonal antibody specific for human CD3, was used as the positive control. The staining of cells was analyzed by FACS (FACSCanto II; BD Biosciences). The x-axis of histogram is the fluorescence intensity. FIG. 23B shows that the mutated teplizumab bound to T cells.

Example 19: Preparation of DBCO-scFv Specific for CD3

The DNA sequence encoding SEQ ID NO: 12 was synthesized and expressed as in the above Examples. The sequences of $V_H$ and $V_L$ of scFv specific for CD3 were those of $V_H$ and $V_L$ of mutated Teplizumab. For the conjugation with Mal-PEG$_5$-DBCO (Conju-probe, Inc.), the cysteine residue at the C-terminal end of the purified scFv of the mutated teplizumab was reduced by tris(2-carboxyethyl) phosphine (TCEP) at a molar ratio of 1:1 ([TCEP]:[scFv]) at room temperature for 3 hours with gentle shaking. The buffer of reduced anti-CD3 scFv was exchanged to HEPES buffer (100 mM HEPES, pH7.0, 100 mM NaCl, 10% glycerol and 5 mM EDTA) by using NAP-10 Sephadex G-25 column at 4° C. After the reduction reaction and buffer exchange, conjugation was conducted for 1 hour at room temperature in a reaction molar ratio of 1:1 ([Mal-PEG$_5$-DBCO:[scFv]]. The excess crosslinker was removed by a desalting column and the DBCO-conjugated scFv product was analyzed.

Figure 23C:
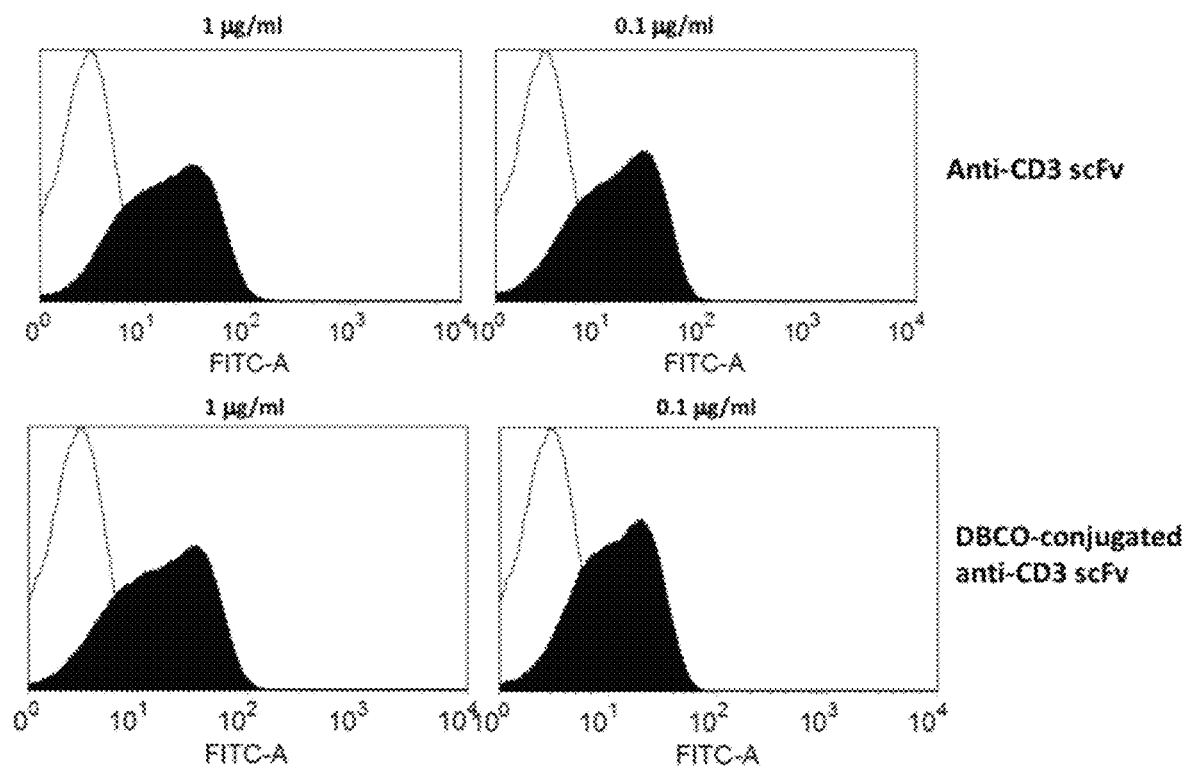

The results of mass spectroscopy MALDI-TOF analysis indicated that the sample of DBCO-conjugated scFv specific for CD3 had a m.w. of 28148 daltons. The purity of DBCO-conjugated scFvs specific for CD3 was identified through Coomassie staining of 12% SDS-PAGE (data not shown). FIG. 23C shows the results of the flow cytometric analysis of DBCO-conjugated scFv specific for CD3 and anti-CD3 scFv (positive control). The results demonstrated that, like the unconjugated scFv, the present DBCO-conjugated scFv specific for CD3 bound to T cells as well.

Example 20: Staining Analysis Showing Binding of CCK8 Peptide Molecule to CCK-Type B Receptor-Expressing Tumor Cell Line The CCK8 peptide molecule was analyzed for its ability to bind to human CCK8-type B receptor molecules on Panc-1 tumor cell line. Panc-1 was established from a pancreatic carcinoma, which was extracted via pancreaticoduodenectomy specimen from a 56-year-old Caucasian individual. Malignancy of this cell line was verified via in vitro and in vivo assays.

Figure 24:
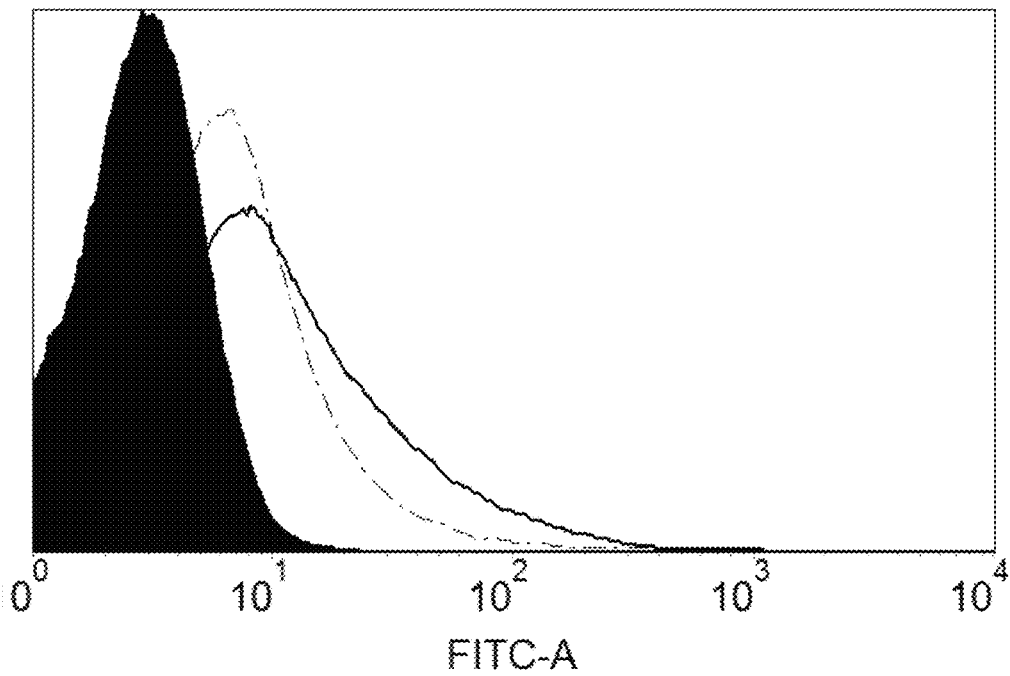
FIG. 24 is the data of flow cytometric analysis of the DBCO-conjugated anti-CD3 scFv according to Example 20 of the present disclosure.

Prior to staining, the Cys-containing CCK8 peptide was conjugated with maleimide-FITC to produce a FITC-labeled CCK8 peptide as a detective CCK8 molecule with FITC. The assay was then performed by incubating 2×10$^6$ Panc-1 cells with 150 μg/ml of the reaction mixture of CCK8-FITC molecule in PBS, with 1 FBS and 1% sodium azide on ice for 30 minutes in the dark. The staining of maleimide-FITC alone was used a negative control. The staining of cells was analyzed by FACS (FACSCanto II; BD Biosciences). The x-axis of histogram is the fluorescence intensity. In FIG. 24, the dark area represents the background of fluorescence distribution of Panc-1 cells, the dashed line is the fluorescence distribution of Panc-1 cells stained maleimide-FITC and the dark line is the fluorescence distribution of Panc-1 cells stained CCK8-FITC. The result of the staining analysis shows that the FITC-labeled CCK8 peptide molecule bound to Panc-1 cells.

Example 21: Preparation of Molecular Construct with Four-Arm CCK8-Containing Targeting Bundle and One scFv Specific for CD3 as Effector Element In this example, the CCK8-containing targeting linker unit of the preceding examples and an effector element of DBCO-scFv specific for CD3 were coupled via the SPAAC reaction. As discussed above, the targeting linker unit had branched arms having the sequence of SEQ ID NO: 16 and one free azide group.

The process for the SPAAC reaction was performed per the manufacturer's instructions (Conju-Probe Inc.). Briefly, 113 μl of the targeting linker unit (12.4 mg/ml) was added to the solution containing the effector element at a molar ratio of 1:1 ([azide]:[DBCO]). The reaction mixture was incubated for 3 hours at room temperature.

The product, as illustrated below, was a single linker unit molecular construct with four arms containing the CCK8 and one scFv specific for CD3 as an effector element. The result of the SDS-PAGE analysis of the reaction mixture after the conjugation indicated that the size of the present molecular construct was consistent with the expected size.

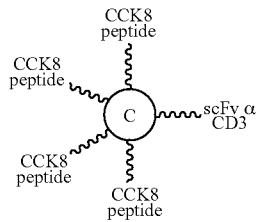

Example 22: Preparation of Joint-Linker Molecular Construct Composed of Targeting Linker Unit with Three CCK8 Peptide Molecules and Effector Linker Unit with 5 DM1 Molecules The process for carrying out the SPAAC reaction was performed as described in the previous Example.

Figure 25:
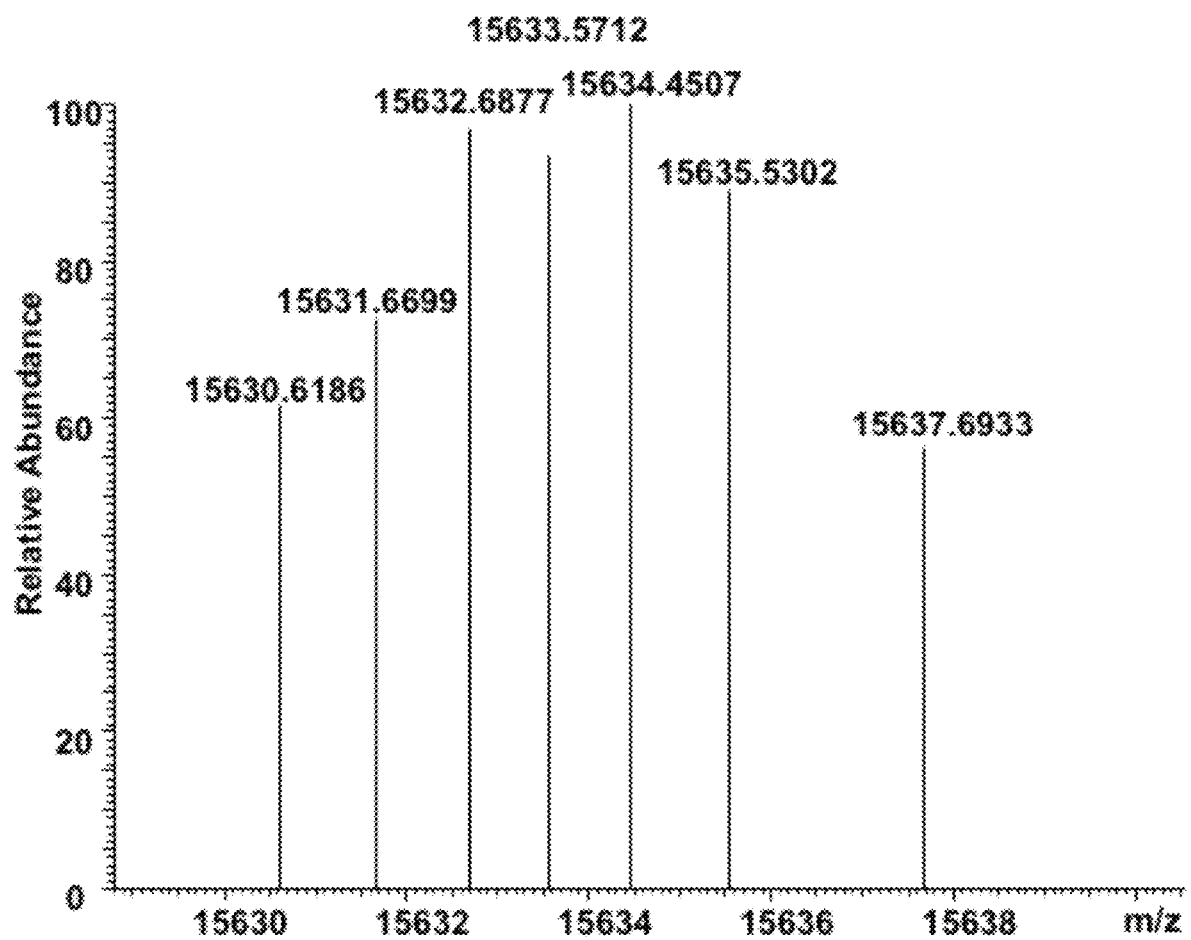
FIG. 25 shows the result of mass spectrometric analysis of the linking unit and molecular construct according to Example 22 of the present disclosure.

In this example, a targeting linker unit with three CCK peptide molecules and one free DBCO group and an effector linker unit (a drug bundle) with five DM1 molecules and one free azide group were coupled via a SPAAC reaction as set forth in the preceding Example. Illustrated below was the resultant joint-linker molecular construct that had three CCK8 peptides and one drug bundle having five DM1 molecules. The data show (ESI-TOF) m/z: [M+H]⁺—calculated for $C_{686}H_{993}N_{129}O_{246}S_{14}C_{15}Na_1$ 15632.07; found 15630.6186. The six isotopic peaks were also visible in the MS spectrum at 15631.6699, 15632.6877, 15633.5712, 15634.4507, 15635.5302 and 15637.6933, corresponding to [M+H+1]⁺, [M+H+2]⁺, [M+H+3]⁺, [M+H+4]⁺, [M+H+5]⁺ and [M+H+6]⁺ (FIG. 25).

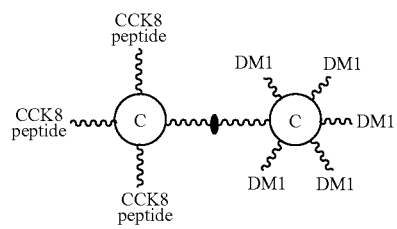

Example 23: Analysis of Thiol-Exchange Adducts of the Synthesized DBCO-PEG$_3$-Maleimide Conjugated Peptide 16 (SEQ ID NO: 22) and Methyltetrazine-PEG$_4$-Maleimide Conjugated Peptide 16 (SEQ ID NO: 22) Under Existence of Glutathione by MALTI-TOF Mass Spectrometry The maleimide group can react specifically with sulfhydryl-containing molecules when the pH of the reaction mixture is between 6.5 and 7.5. The Michael-addition of a thiol to a maleimide has been commonly used for various bioconjugation to form thiol-maleimide adducts. However, the thiol-maleimide adduct could undergo disruptive cleavage by thiol exchange under physiological condition. The so-called retro-thiol-Michael reaction may lead to degradation of the thiol-maleimide adduct and reduce the stability of the adduct.

In this example, both DBCO-PEG$_3$-maleimide conjugated peptide 16 and methyltetrazine-PEG$_4$-maleimide conjugated peptide 16 were investigated for the thiol-maleimide exchange of the synthesized thiol-maleimide peptide cores with coupling groups under existence of thiol-containing glutathione molecules in the aqueous solution by MALDI-TOF analysis. A DBCO-PEG$_3$-maleimide conjugated peptide 16 was prepared as follows: the peptide 16 was synthesized by a standard solid-phase method (the inventors outsourced the production of peptide 16 to Shanghai ChinaPeptide Co., Ltd.). The peptide 16 (Acetyl-CGGSGGSGGSKGSGSKGSK; SEQ ID NO: 22) had a purity of 95%, in which the N-terminus of the peptide 16 was modified by an acetyl group. The hetero-bifunctional crosslinker, DBCO-PEG$_3$-maleimide, was purchased from Conju-probe Inc. The thiol-maleimide conjugation of the crosslinker, DBCO-PEG$_3$-maleimide, to the peptide 16 was the same as that described in preceding Examples. The thus-synthesized DBCO-peptide 16 had a m.w. of 2227 dalton (illustrated below).

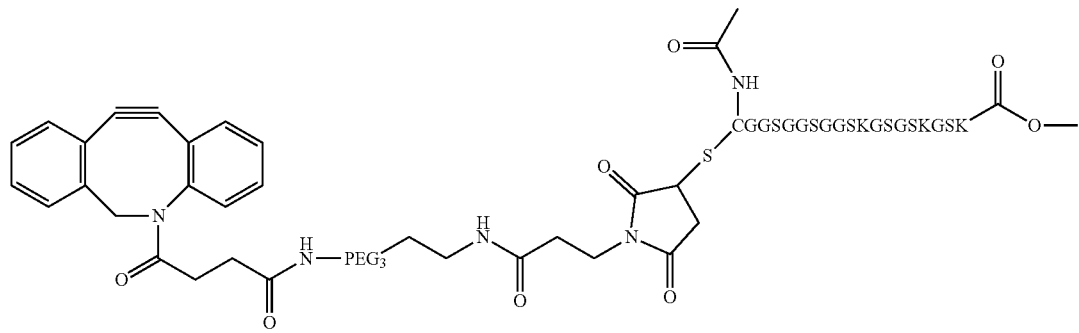

Figure 26A:
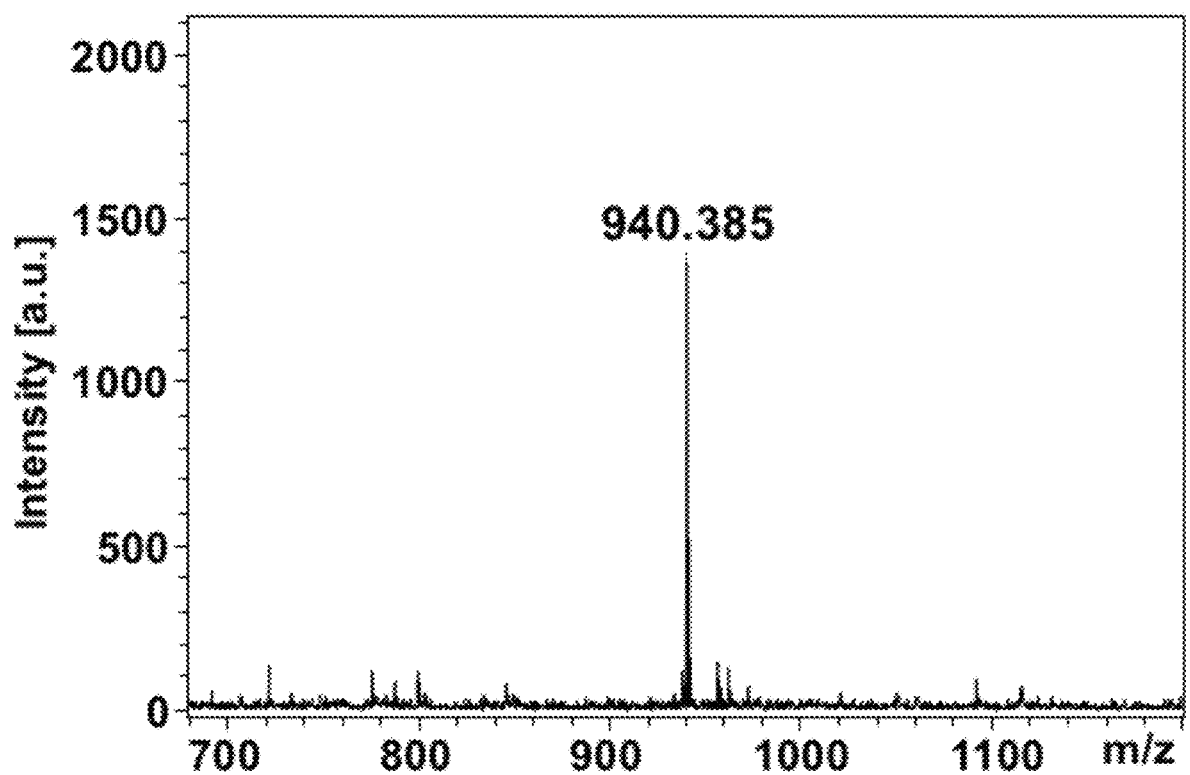
FIGS. 26A and 26B show the result of mass spectrometry MALDI-TOF analysis of the linker unit according to Example 23 of the present disclosure.

The thus-synthesized DBCO-PEG$_3$-maleimide peptide 16 was then incubated with glutathione at a molar ratio of 1:10 ([peptide]:[glutathione]) for 24, 48 and 72 hours at 37° C. in 100 mM HEPES buffer, pH 7.0, and 100 mM NaCl. The resultant reaction mixture was further analyzed using MALDI-TOF, and the result showed that DBCO-PEG$_3$-maleimide glutathione adduct (illustrated below) resulted from thiol-maleimide exchange after 72-hour incubation had a molecular weight of 940.385 daltons (FIG. 26A).

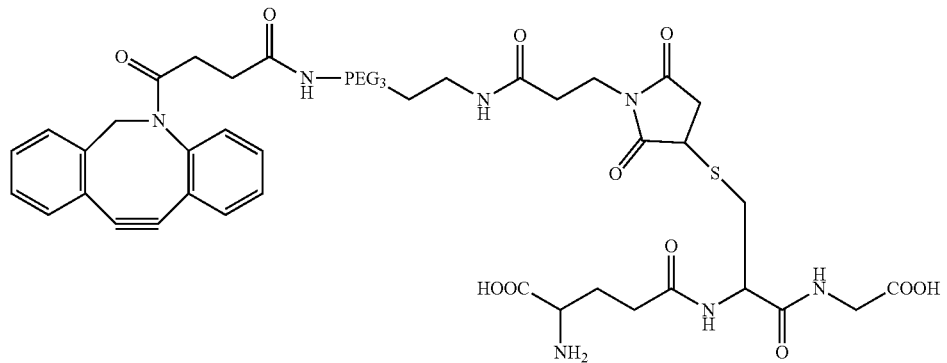

A methyltetrazine-PEG$_4$-maleimide conjugated peptide 16 was prepared and analyzed in the same way as described in the preparation of DBCO-PEG$_3$-maleimide conjugated peptide 16. The thus-synthesized methyltetrazine-PEG$_4$-maleimide peptide 16 had a m.w. of 2111.2 dalton (illustrated below).

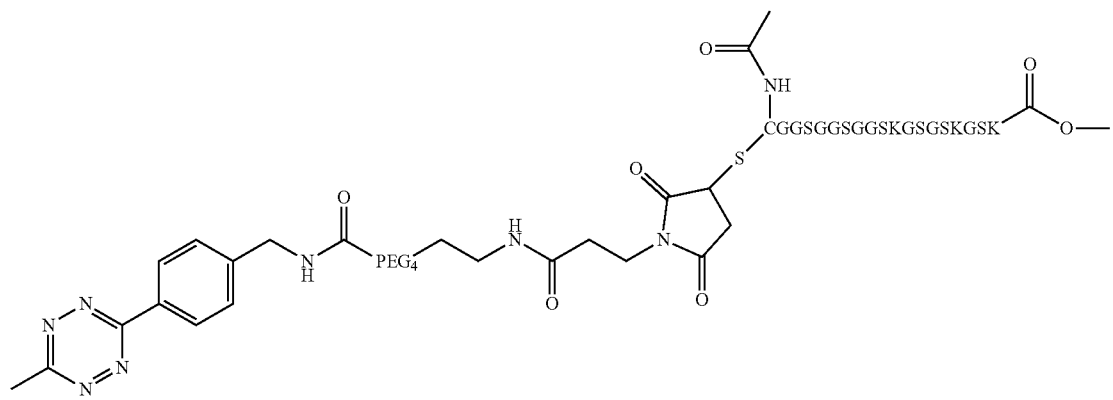

Figure 26B:
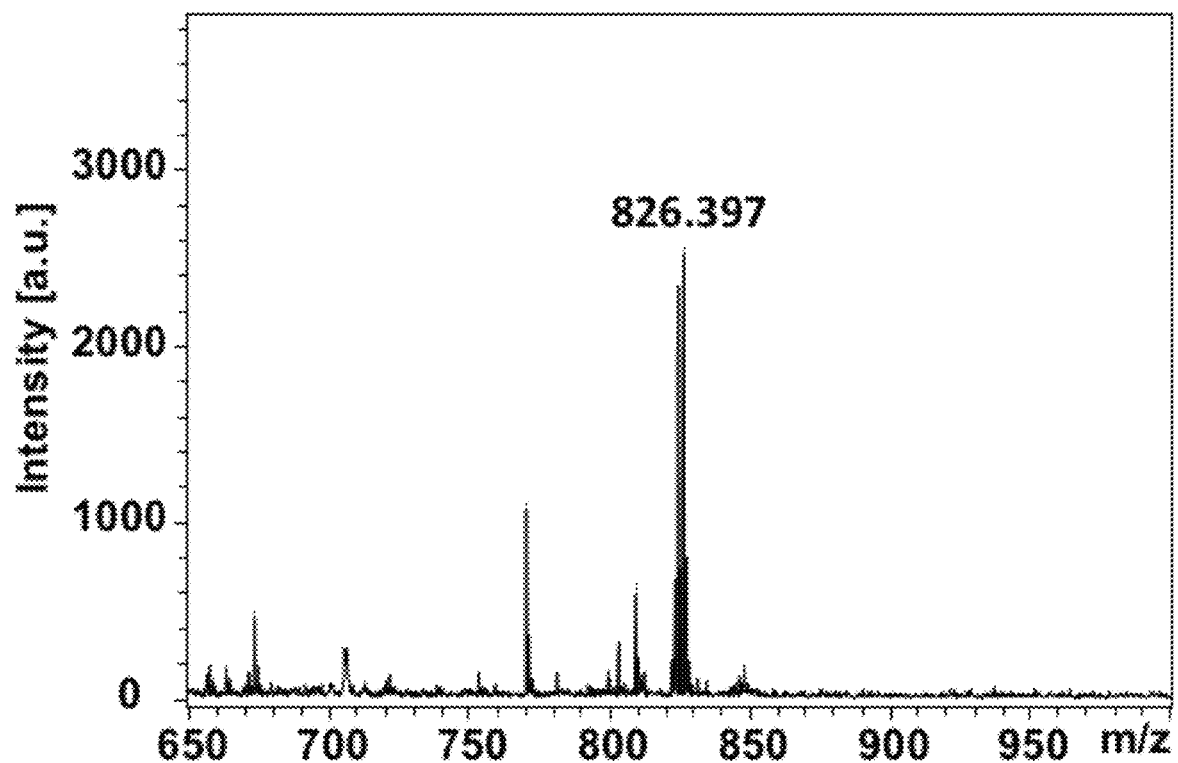

The reaction of the thus-synthesized methyltetrazine-PEG₄-maleimide peptide 16 with glutathione was the same as described in the condition of DBCO-PEG₃-maleimide peptide 16 reacted with glutathione. The resultant reaction mixture was further analyzed by MALDI-TOF. The result of mass spectrometric analysis showed that methyltetrazine-PEG₄-maleimide glutathione adduct (illustrated below) was observed by MALDI-TOF after 72 hours of incubation (FIG. 26B), and the adduct had a molecular weight of 826.397 daltons.

targeting moiety with four CCK8 peptides and an effector moiety with one anti-CD3 scFv molecule was prepared in an earlier Example.

For the cytotoxic effects, the isolated human T lymphocytes from donor were selected to examine the T-cell mediated cytotoxicity. Panc-1 cells were incubated with 10 μg/mL of the molecular construct composed of a targeting moiety with four CCK8 peptides and an effector moiety with one anti-CD3 scFv molecule at 37° C. for 1 hour, and then mixed with human T lymphocytes at different E:T ratios of,

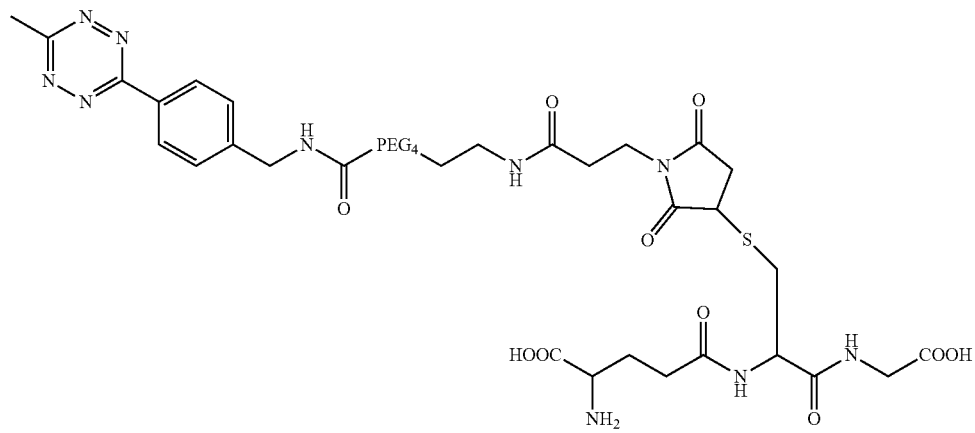

Example 24: T Cell-Mediated Cytotoxicity Assay of the Molecular Construct Composed of Targeting Linker Unit with Four CCK8 Peptide Molecules and Effector Moiety with One Anti-CD3 scFv Molecule on Panc-1 Tumor Cell Lines Human peripheral blood T cells were used as the source of T cells. Peripheral blood mononuclear cells (PBMCs) were isolated from buffy coats from healthy donors (Taiwan Blood Service Foundation) by centrifugation over a Ficoll-Paque PLUS (GE Healthcare) density gradient and cryopreserved in 90% FBS/10% DMSO. Human T cells were prepared from PBMCs by depletion of non-T cells (negative selection) using the human Pan T cell Isolation kit (Miltenyl Biotech, Auburn, Calif., USA). T cells were cultured in the presence of 10 μ/ml of recombinant human IL-2 (PeproTech, Rocky Hill, USA). Anti-DNP AN02 mAb was used as an isotype-matched control.

Aliquots of 5,000 Panc-1 target cells in 100 μl complete RPMI medium were cultured with the molecular construct composed of a targeting moiety with four CCK8 peptides and an effector moiety with one anti-CD3 scFv molecule, or the targeting moiety with four CCK8 peptides alone as a negative control for 30 minutes at 37° C. in a 5% CO₂ atmosphere, and then combined with human T cells at different E:T ratios of 20, 10 or 5. After 24 hours of incubation, the cytotoxicity was assayed by a luminescent method using the aCella-Tox kit (Cell Technology, Mountain View, Calif.) according to the manufacturer's instructions. The plate was read by a luminometer (multi-detection microplate reader, DS Pharma, Osaka, Japan).

T cell-mediated cytolysis of CCK8-type B receptor-expressing tumor cells by the molecular construct composed of a targeting moiety with four CCK8 peptides and an effector moiety with one anti-CD3 scFv molecule was studied using Panc-1 tumor cells. The molecular construct composed of a targeting moiety with four CCK8 peptides and an effector moiety with one anti-CD3 scFv molecule was prepared in an earlier Example.

20, 10 or 5, and incubated for 24 hours. The targeting moiety with four CCK8 peptides alone (without effector moiety) and the effector moiety with one anti-CD3 scFv (without targeting moiety) alone were used as negative controls. Cytolysis was analyzed by using an aCella-Tox kit.

Example 25: Cytotoxic Assay of Joint-Linker Molecular Construct Composed of Targeting Linker Unit with Three CCK8 Peptide Molecules and Effector Linker Unit with 5 DM1 Molecules on Panc-1 Tumor Cell Lines The joint-linker molecular construct composed of targeting linker unit with three CCK8 peptide and effector linker unit with 5 DM1 molecule was prepared in an earlier Example.

Panc-1 cells (2×10⁴/well) were seeded into wells of 96-well plates in DMEM medium containing 10% fecal bovine serum. After 18 hours, cells were treated with different concentrations (10-fold dilutions from 1 μM) of a linker unit with three CCK-8 peptides (without a drug bundle), a linker unit with five DM1 molecules (a drug bundle), and a molecular construct with three CCK-8 peptides as a targeting moiety and five DM1 molecules as an effector moiety. After being incubated for 6 hours, the culture medium was replaced by a fresh medium, and the cells were further incubated for another 48 hours. Cell viability was then determined by alamarBlue cell viability reagent kit (Invitrogen) in accordance with the manufacturer's instruction.

Figure 27:
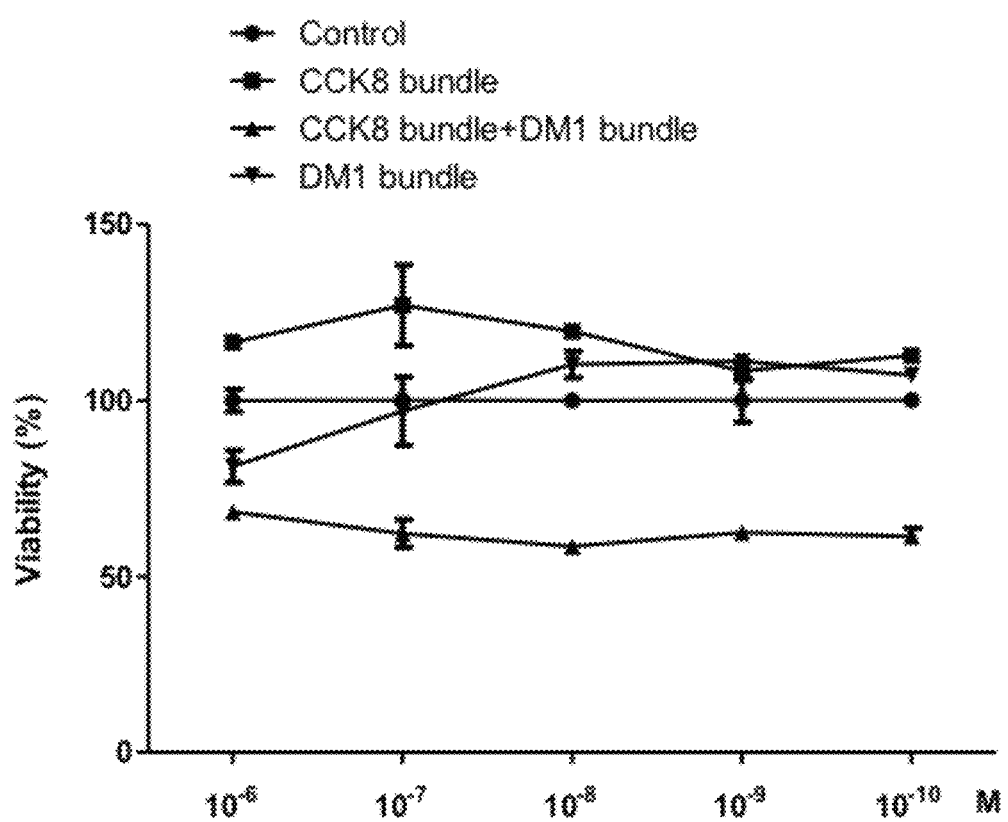
FIG. 27 shows the result of the cytotoxic effect of the linker unit comprising five cytotoxic drugs on tumor cells according to Example 25 of the present disclosure.

FIG. 27 shows the results of the viability of Panc-1 cells of the three treatments groups. The molecular construct with a targeting linker unit of three CCK-8 peptides and a drug bundle of five DM1 molecules caused approximately 35% of cytolysis of Panc-1 cells.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A linker unit comprising,
a core, which comprises, a plurality of lysine (K) residues, one or more spacers, and a first conjugating moiety, wherein,
any two of the K residues are adjacent to each other or are separated by one of the spacers,
each of the spacers comprises, independently, (1) one or more non-K amino acid residues, or (2) a PEGylated amino acid having 2 to 12 repeats of ethylene glycol (EG) unit,
at least one of the spacers is linked to the N-terminus of the first K residue starting from the N-terminus or the C-terminus of the last K residue starting from the N-terminus, and
the first conjugating moiety has either a carboxyl group or an amine group, and a conjugating group selected from the group consisting of, azide, alkyne, tetrazine, cyclooctene and cyclooctyne groups, wherein,
when the spacer is linked to the N-terminus of the first K residue, the first conjugating moiety has the carboxyl group and is bonded to the spacer via forming an amide bond with the alpha-amine group of the spacer; or
when the spacer is linked to the C-terminus of the last K residue, the first conjugating moiety has the amine group and is bonded to the spacer via forming an amide bond with the carboxyl group of the spacer; and
a plurality of linking arms, wherein,
each of the linking arms has a reactive group at one terminus thereof and a functional group at the other terminus thereof, and is linked to the K residues of the core via forming an amide bond between the reactive group of the linking arm and the amine group of the K reside of the core, and
the functional group is selected from the group consisting of amine, carboxyl, hydroxyl, tert-Butyldimethylsilyl (TBDMS), N-hydroxysuccinimidyl (NHS), maleimide, vinyl sulfone, mono-sulfone, methylsulfonyl benzothiazole, iodo, iodoacetamide, azide, alkyne, cyclooctyne, tetrazine, and cyclooctene groups, with the proviso that when the conjugating group is the azide, alkyne, or cyclooctyne group, then the functional group is the tetrazine or cyclooctene group, and when the conjugating group is the tetrazine or the cyclooctene group, then the functional group is the azide, alkyne, or cyclooctyne group.

2. The linker unit of claim 1, wherein the core comprises 2-20 K residues.

3. The linker unit of claim 1, wherein the spacer comprises one or more glycine (G) and/or serine (S) residues.

4. The linker unit of claim 1, wherein the reactive group is a succinimidyl ester (SE), tetrafluorophenyl (TFP) ester, or carboxyl group.

5. The linker unit of claim 1, wherein the core comprises two spacers respectively linked to the N-terminus of the first K residue and the C-terminus of the last K residue.

6. The linker unit of claim 5, wherein the core further comprises a second conjugating moiety, which has either a carboxyl group or an amine group, and a conjugating group selected from the group consisting of, azide, alkyne, tetrazine, cyclooctene and cyclooctyne groups, wherein,
one of the first and second conjugating moieties is bonded to the N-terminus of the spacer linked to the N-terminus of the first K residue, and
the other of the first and second conjugating moieties is bonded to the C-terminus of the spacer linked to the C-terminus of the last K residue.

7. The linker unit of claim 6, wherein,
the functional group is the maleimide, vinyl sulfone, mono-sulfone, iodo or iodoacetamide group;
the conjugating group of one of the first and second conjugating moieties is the azide, alkyne, or cyclooctyne group; and
the conjugating group of the other of the first and second conjugating moieties is the tetrazine or cyclooctene group.

8. The linker unit of claim 1, wherein each of the linking arms is a peptide comprising 2-12 non-K amino acid residues; or a polyethylene glycol (PEG) chain having 2-24 repeats of EG units.

9. The linker unit of claim 8, wherein the peptide of the linking arm comprises 5-10 amino acid residues that are independently selected from the group consisting of, G, S, glutamic acid (E) and arginine (R) residues.

10. The linker unit of claim 1, wherein,
the cyclooctene group is norbornene or trans-cyclooctene (TCO);
the cyclooctyne group is dibenzocyclooctyne (DIBO), difluorinated cyclooctyne (DIFO), bicyclononyne (BCN), or dibenzoazacyclooctyne (DIBAC); or
the tetrazine group is 1,2,3,4-tetrazine, 1,2,3,5-tetrazine or 1,2,4,5-tetrazine, or derivatives thereof.

11. The linker unit of claim 1, wherein the core further comprises a plurality of first elements respectively linked to the plurality of linking arms via forming an amide bond or an ester bond therebetween, or via thiol-maleimide reaction, SN2 reaction, copper catalyzed azide-alkyne cycloaddition (CuAAC) reaction, strained-promoted azide-alkyne click chemistry (SPAAC) reaction, or inverse electron demand Diels-Alder (iEDDA) reaction.

12. The linker unit of claim 11, wherein the core further comprises a second element linked to the conjugating group via CuAAC reaction, SPAAC reaction or iEDDA reaction.

13. The linker unit of claim 12, wherein,
each of the first element is a first antibody fragment specific for a first cell surface antigen; and
the second element is a cytotoxic drug or a second antibody fragment specific for a second cell surface antigen.

14. The linker unit of claim 13, wherein,
the first cell surface antigen is selected from the group consisting of, CD5, CD19, CD20, CD22, CD23, CD27, CD30, CD33, CD34, CD37, CD38, CD43, CD72a, CD78, CD79a, CD79b, CD86, CD134, CD137, CD138, and CD319; or
the second cell surface antigen is CD3 or CD16a.

15. The linker unit of claim 12, wherein,
each of the first elements is a peptide hormone, a first growth factor, or a first antibody fragment specific for a tumor-associated antigen; and
the second element is a cytotoxic drug, a toll-like receptor agonist, a chelator complexed with a radioactive nuclide, a cytokine, or a second antibody fragment specific for a second growth factor, a cell surface antigen, a hapten, or the cytokine.

16. The linker unit of claim 15, wherein,
the first growth factor is selected from the group consisting of epidermal growth factor (EGF), mutant EGF, epiregulin, heparin-binding epidermal growth factor (HB-EGF), vascular endothelial growth factor A (VEGF-A), basic fibroblast growth factor (bFGF), and hepatocyte growth factor (HGF);

the second growth factor is selected from the group consisting of, EGF, mutant EGF, VEGF-A, bFGF, and HGF;

the peptide hormone is selected from the group consisting of, secretin, cholecystokinin (CCK), somatostatin, octreotide, and thyroid-stimulating hormone (TSH);

the tumor-associated antigen is selected from the group consisting of, epidermal growth factor receptor (HER1), HER2, HER3, HER4, carbohydrate antigen 19-9 (CA 19-9), CA 125, carcinoembryonic antigen (CEA), mucin 1 (MUC 1), ganglioside GD2, melanoma-associated antigen (MAGE), prostate-specific membrane antigen (PSMA), prostate stem cell antigen (PSCA), mesothelin, mucine-related Tn, Sialyl Tn, Globo H, stage-specific embryonic antigen-4 (SSEA-4), and epithelial cell adhesion molecule (EpCAM); or the cell surface antigen is selected from the group consisting of CD3, CD16a, CD28, CD134, cytotoxic T-lymphocyte-associated protein 4 (CTLA-4), programmed cell death 1 (PD-1), and programmed cell death 1 ligand 1 (PD-L1).

17. The linker unit of claim 7, wherein the core further comprises, a plurality of first elements that are respectively linked to the plurality of linking arms via forming an amide bond or an ester bond therebetween, or via thiol-maleimide reaction or SN2 reaction; and a second element and a third element, respectively linked to the conjugating groups of the first and second conjugating moieties, wherein one of the second and third elements is linked to one conjugating group via iEDDA reaction, and the other of the second and third elements is linked to the other conjugating group via SPAAC or CuAAC reaction.

18. A molecular construct, comprising a first linker unit and a second linker unit, independently according to any of claim 1, wherein the first and the second linker units are coupled by the reaction occurred between the conjugating groups of the first and the second linker units via CuAAC reaction, SPAAC reaction or iEDDA reaction.

19. The molecular construct of claim 18, further comprising a plurality of first elements and a plurality of second elements, respectively linked to the plurality of linking arms of the first linker unit and the second linker unit via forming an amide bond or an ester bond therebetween, or via thiol-maleimide reaction, SN2 reaction, CuAAC reaction, SPAAC reaction, or iEDDA reaction.

20. The molecular construct of claim 19, wherein, each of the first element is a first antibody fragment specific for a first cell surface antigen; and each of the second element is a cytotoxic drug or a second antibody fragment specific for a second cell surface antigen.

21. The molecular construct of claim 20, wherein, the first cell surface antigen is selected from the group consisting of, CD5, CD19, CD20, CD22, CD23, CD27, CD30, CD33, CD34, CD37, CD38, CD43, CD72a, CD78, CD79a, CD79b, CD86, CD134, CD137, CD138, and CD319; or the second cell surface antigen is CD3 or CD16a.

22. The molecular construct of claim 19, wherein, each of the first elements is a peptide hormone, a first growth factor, or a first antibody fragment specific for a tumor-associated antigen; and each of the second elements is a cytotoxic drug, a toll-like receptor agonist, a chelator complexed with a radioactive nuclide, a cytokine, or a second antibody fragment specific for a second growth factor, a cell surface antigen, a hapten, or the cytokine.

23. The molecular construct of claim 22, wherein, the first growth factor is selected from the group consisting of EGF, mutant EGF, epiregulin, HB-EGF, VEGF-A, bFGF, and HGF;

the second growth factor is selected from the group consisting of, EGF, mutant EGF, VEGF-A, bFGF, and HGF;

the peptide hormone is selected from the group consisting of, secretin, CCK, somatostatin, octreotide, and TSH;

the tumor-associated antigen is selected from the group consisting of, HER1, HER2, HER3, HER4, CA 19-9, CA 125CEA, MUC 1, ganglioside GD2, MAGE, PSMA, PSCA, mesothelin, mucine-related Tn, Sialyl Tn, Globo H, SSEA-4, and EpCAM; or the cell surface antigen is selected from the group consisting of CD3, CD16a, CD28, CD134, CTLA-4, PD-1, and PD-L1.

* * * * *